US011725246B2

(12) United States Patent
Ghosh et al.

(10) Patent No.: US 11,725,246 B2
(45) Date of Patent: Aug. 15, 2023

(54) METHODS OF TREATING OPHTHALMIC DISORDERS

(71) Applicant: NOVARTIS AG, Basel (CH)

(72) Inventors: Joy Ghosh, Boston, MA (US); Yunsheng He, Waltham, MA (US)

(73) Assignee: NOVARTIS AG, Basel (CH)

( * ) Notice: Subject to any disclaimer, the term of this patent is extended or adjusted under 35 U.S.C. 154(b) by 5 days.

(21) Appl. No.: 16/998,830

(22) Filed: Aug. 20, 2020

(65) Prior Publication Data

US 2021/0047692 A1 Feb. 18, 2021

Related U.S. Application Data

(63) Continuation-in-part of application No. 15/751,787, filed as application No. PCT/IB2016/054851 on Aug. 11, 2016, now abandoned.

(60) Provisional application No. 62/204,115, filed on Aug. 12, 2015.

(51) Int. Cl.
*C12Q 1/6883* (2018.01)
*A61P 27/02* (2006.01)
*C07K 16/22* (2006.01)

(52) U.S. Cl.
CPC ............ *C12Q 1/6883* (2013.01); *A61P 27/02* (2018.01); *C07K 16/22* (2013.01); *C07K 2317/24* (2013.01); *C07K 2317/55* (2013.01); *C07K 2317/565* (2013.01); *C07K 2317/76* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 4,703,008 | A | 10/1987 | Lin |
| 5,712,370 | A | 1/1998 | Fibi et al. |
| 7,396,913 | B2 | 7/2008 | Devries et al. |
| 9,062,105 | B1 | 6/2015 | Clube |
| 9,365,646 | B2 | 6/2016 | Ghosh et al. |
| 2002/0045582 | A1 | 4/2002 | Margolin et al. |
| 2003/0049683 | A1 | 3/2003 | Bowdish et al. |
| 2003/0050269 | A1 | 3/2003 | Escary |
| 2004/0091961 | A1 | 5/2004 | Evans et al. |
| 2005/0255112 | A1 | 11/2005 | Lee et al. |

(Continued)

FOREIGN PATENT DOCUMENTS

| CN | 102 872 464 A2 | 1/2013 |
| CN | 104744593 A | 7/2015 |

(Continued)

OTHER PUBLICATIONS

Clinical Trials.gov NCT00436553, available vial URL: <clinicaltrials.gov/ct2/show/results/NCT00436553>, 33 pages, Apr. 19, 2011 (Year: 2011).*

(Continued)

*Primary Examiner* — Carla J Myers

(57) ABSTRACT

The invention features methods of identifying patients as being likely to respond to anti-VEGF therapy. Furthermore, in those patients identified as failing to include one or more of the above ophthalmic response markers, the invention features treatment with an EPO antagonist (e.g., alone, or in combination with a VEGF antagonist).

6 Claims, 6 Drawing Sheets

Specification includes a Sequence Listing.

Effect of EPO genotype on BCVA response in DME patients treated with Lucentis

(56) References Cited

U.S. PATENT DOCUMENTS

| | | |
|---|---|---|
| 2007/0224201 A1 | 9/2007 | Wu et al. |
| 2009/0004202 A1 | 1/2009 | Brines et al. |
| 2009/0238789 A1 | 9/2009 | Guyon et al. |
| 2009/0252746 A1 | 10/2009 | Devries et al. |
| 2011/0053787 A1 | 3/2011 | Brulliard et al. |
| 2011/0091463 A1 | 4/2011 | Ghayur et al. |
| 2011/0091474 A1 | 4/2011 | Zhang |
| 2011/0143372 A1 | 6/2011 | Jarsch et al. |
| 2012/0014958 A1 | 1/2012 | Borras et al. |
| 2012/0082681 A1 | 4/2012 | Carballido Herrera et al. |
| 2012/0195900 A1 | 8/2012 | Ghayur et al. |
| 2012/0201746 A1 | 8/2012 | Liu et al. |
| 2012/0207743 A1 | 8/2012 | Jacky et al. |
| 2013/0064836 A1 | 3/2013 | Diefenbach-Streiber et al. |
| 2013/0295562 A1 | 11/2013 | Ma et al. |
| 2014/0186350 A1 | 7/2014 | Ghosh et al. |
| 2014/0199306 A1 | 7/2014 | Ghosh et al. |

FOREIGN PATENT DOCUMENTS

| | | |
|---|---|---|
| EP | 1611879 A1 | 1/2006 |
| EP | 1736481 A1 | 12/2006 |
| EP | 1699826 B1 | 3/2009 |
| EP | 2062917 A2 | 5/2009 |
| EP | 1732950 A1 | 5/2011 |
| EP | 2120998 B1 | 8/2013 |
| WO | 90/08822 A1 | 8/1990 |
| WO | 2004060270 A2 | 7/2004 |
| WO | 2004089282 A2 | 10/2004 |
| WO | 2007060213 A2 | 5/2007 |
| WO | 2007120766 A2 | 10/2007 |
| WO | 2008079877 A2 | 7/2008 |
| WO | 2008/112703 A2 | 9/2008 |
| WO | 2009015345 A1 | 1/2009 |
| WO | 2009080816 A1 | 7/2009 |
| WO | 2009094551 A1 | 7/2009 |
| WO | 2010015608 A1 | 2/2010 |
| WO | 2010/056893 A1 | 5/2010 |
| WO | 2010054007 A1 | 5/2010 |
| WO | 2010081679 A1 | 7/2010 |
| WO | 2012/103060 A1 | 8/2012 |
| WO | 2012171996 A1 | 12/2012 |
| WO | 2013106489 A1 | 7/2013 |
| WO | 2013/169734 A1 | 11/2013 |
| WO | 2014035693 A2 | 3/2014 |

OTHER PUBLICATIONS

ClinicalTrials.gov NCT00687804, available vial URL: <clinicaltrials.gov/ct2/show/results/NCT00687804>, 52 pages, Apr. 1, 2013 (Year: 2013).*

Yannuzzi, N. et al.: "Brolucizumab: evidence to date in the treatment of neovascular age-related macular degeneration", Clinical Ophthalmology, (2019), vol. 13, pp. 1323-1329.

Hirschhorn et al., Genetics in Medicine, vol. 4, No. 2, pp. 45-61, Mar. 2002.

Lucentini et al., The Scientist, (2004), vol. 18, p. 20.

Hattersley et al., The Lancet, (2005), vol. 366, pp. 1315-1323.

Hautamaki et al., Retina, Oct. 2013, vol. 33, No. 9, pp. 1815-1817.

Simo et al., Diabetes Care, Apr. 2014, vol. 37, pp. 893-899.

Elliott et al., Fine-structure epitope mapping of antierythropoietin monoclonal antibodies reveals a model of recombinant human erythropoietin structure. Blood. Apr. 1, 1996;87(7):2702-13.

Elliott et al., Isolation and characterization of conformation sensitive antierythropoietin monoclonal antibodies: effect of disulfide bonds and carbohydrate on recombinant human erythropoietin structure. Blood. Apr. 1, 1996;87(7):2714-22.

Javey et al., Emerging pharmacotherapies for diabetic macular edema. Exp Diabetes Res. 2012;2012:548732. Epub Feb. 26, 2012.

Watanabe et al., Erythropoietin as a retinal angiogenic factor in proliferative diabetic retinopathy. N Engl J Med. Aug. 25, 2005;353(8):782-92.

Yanagihara et al., Production of novel anti-recombinant human erythropoietin monoclonal antibodies and development of a sensitive enzyme-linked immunosorbent assay for detection of bioactive human erythropoietin, J Immunoassay Immunochem. 2008;29(2):181-96.

Paul, "Fv Structure and Diversity in Three Dimensions" Fundamental Immunology, 3rd Edition, pp. 292-295 (1993).

Rudikoff et al., "Single amino acid substitution altering antigen-binding specificity," Proc Natl Acad Sci U S A. Mar. 1982;79(6):1979-83.

Amadeo et al., "A single monoclonal antibody as probe to detect the entire set of native and partially unfolded rhEPO glycoforms," J Immunol Methods. Oct. 2004;293(1-2):191-205.

D'Andrea et al., "Inhibition of receptor binding and neutralization of bioactivity by anti-erythropoietin monoclonal antibodies," Blood. Feb. 15, 1990;75(4):874-80.

Goto et al., "Characterization and use of monoclonal antibodies directed against human erythropoietin that recognize different antigenic determinants," Blood. Sep. 1989;74(4):1415-23.

Sytkowski et al., "Site-specific antibodies to human erythropoietin directed toward the NH2-terminal region," Proc Natl Acad Sci U S A. Jun. 1983;80(12):3651-5.

Sytkowski et al., "Isolation and characterization of an anti-peptide monoclonal antibody to human erythropoietin," J Biol Chem. Nov. 25, 1985;260(27):14727-31.

Fibi et al., "Human erythropoietin-specific sites of monoclonal antibody-mediated neutralization," Blood. Feb. 1, 1993;81(3):670-5.

Elliott et al., "Mapping of the active site of recombinant human erythropoietin," Blood. Jan. 15, 1997;89(2):493-502.

Ascaso et al. The role of inflammation in the pathogenesis of macular edema secondary to retinal vascular diseases. Mediators of Inflammation, vol. 2014, pp. 1-6 (2014).

Kent et al. Macular oedema: the role of soluble mediators. British Journal of Ophthalmology vol. 84/No. 5:542-545 (2000).

Bainbridge et al. Inhibition of retinal neovascularization by gene transfer of soluble VEGF receptor sFitl-1. Gene therapy, vol. 9:320-326 (2002).

Yoshida et al. Suppression of retinal neovascularization by the NF-kB inhibitor pyrrolidine dithiocarbamate in mice. IOVS, vol. 40/No. 7, pp. 1624-1629 (1999).

Du et al. "Molecular Basis of Recognition of Human Osteopontin by 23C3, a Potential Therapeutic Antibody for Treatment of Rheumatoid Arthritis" J. Mol. Biol. (2008), vol. 382, pp. 835-842.

Caldas et al. "Humanization of the anti-CD18 antibody 6.7: an unexpected effect of a framework residue in binding to antigen" Molecular Immunology (2003), vol. 39, pp. 941-952.

Garcia-Ramirez et al. "Erythropoietin protects retinal pigment epithelial cells against the increase of permeability induced by diabetic conditions: Essential role of JAK2/ PI3K signaling" Cellular Signalling (2011), vol. 23, pp. 1596-1602.

Zhang et al. "Intravitreal Injection of Erythropoietin Protects both Retinal Vascular and Neuronal Cells in Early Diabetes" Investigative Ophthalmology & Visual Science (2008), vol. 49, No. 2, pp. 732-742.

Li et al. "Effects of Intravitreal Erthropoietin Therapy for Patients with Chronic and Progressive Diabetic Macular Edema" Ophthalmic Surgery, Lasers and Imaging Retina, Abstract (2010), vol. 41, No. 1, (3 pages).

Tong Z et al "Promoter polymorphism of the erythropoietin gene in severe diabetic eye and kidney complications", Proceedings of the National Academy of Sciences, National Academy of Sciences, vol. 105, No. 19, (2008), pp. 6998-7003.

Abhary S et al "Association Between Erythropoietin Gene Polymorphisms and Diabetic Retinopathy", Archives of Ophthalmology, (2010), pp. 102-106.

Hermann M M et al "Polymorphismsin Vascular Endothelial Growth Factor Receptor 2 Are Associated with Better Response Rates to Ranibizumab Treatment in Age-related Macular Degeneration", Ophthalmology, (2014), vol. 121, No. 4, pp. 905-910.

(56) References Cited

OTHER PUBLICATIONS

Balasubbu S et al "Association analysis of nine candidate gene polymorphisms in Indian patients with type 2 diabetic retinopathy", BMC Medical Genetics, Biomed Central, vol. 11, No. I, (2010), p. 158.

Fan Y et al "Gene interaction of erythropoietin gene polymorphisms and diabetic retinopathy in Chinese Han", Experimental Biology and Medicine, (2016), vol. 241, No. 14, pp. 1524-1530.

Boltz A et al "Role of Vascular Endothelial Growth Factor Polymorphisms in the Treatment Success in Patients with Wet Age-related Macular Degeneration", Ophthalmology, (2012) vol. 119, No. 8, pp. 1615-1620.

Hagstrom S A et al "VEGFA and VEGFR2 Gene Polymorphisms and Response to Anti-Vascular Endothelial Growth Factor Therapy" JAMA Ophthalmology, (2014), vol. 132, No. 5, p. 521.

Tsuchihashi T et al "Complement Factor H and High-Temperature Requirement A-1 Genotypes and Treatment Response of Age-related Macular Degeneration" Ophthalmology, (2011), vol. 118, No. I, pp. 93-100.

Boekhoorn S S et al "Polymorphisms in the Vascular Endothelial Growth Factor Gene and Risk of Age-related Macular Degeneration", Ophthamology, (2008), vol. 115, No. 11, pp. 1899-1903.

Lin T H et al "Functional vascular endothelial growth factor gene polymorphisms and diabetes: Effect on coronary collaterals in patients with significant coronary artery disease" Clinica Chimica Acta, (2010), vol. 411, No. 21-22, pp. 1688-1693.

Gora-Tybor J et al "Clinical relevance of vascular endothelial growth factor type A (VEGFA) and VEGF receptor type 2 (VEGFR2) gene polymorphism in chronic lymphocytic leukemia" Blood Cells, Molecules and Diseases, (2014), vol. 54, No. 2, pp. 139-143.

Kim Y H et al "VEGF polymorphisms in early cervical cancer susceptibility, angiogenesis, and survival" Gynecologiconcology, (2010), vol. 119, No. 2,, pp. 232-236.

Watson C J et al "Identification of polymorphisms within the vascular endothelial growth factor (VEGF) gene: correlation with variation in VEGF protein production" Cytokine, Academic Press Ltd, (2000), vol. 12, No. 8, pp. 1232-1235.

Agosta E et al "Pharmacogenetics of antiangiogenic and antineovascular therapies of age-related macular degeneration" Pharmacogenomics, (2012), vol. 13, No. 9, pp. 1037-1053.

International Search Report from PCT/IB2016/054851 dated Feb. 5, 2017, 32 pages.

U.S. Appl. No. 15/751,787.

* cited by examiner

Figure 1   Effect of EPO genotype on BCVA response in DME patients treated with Lucentis
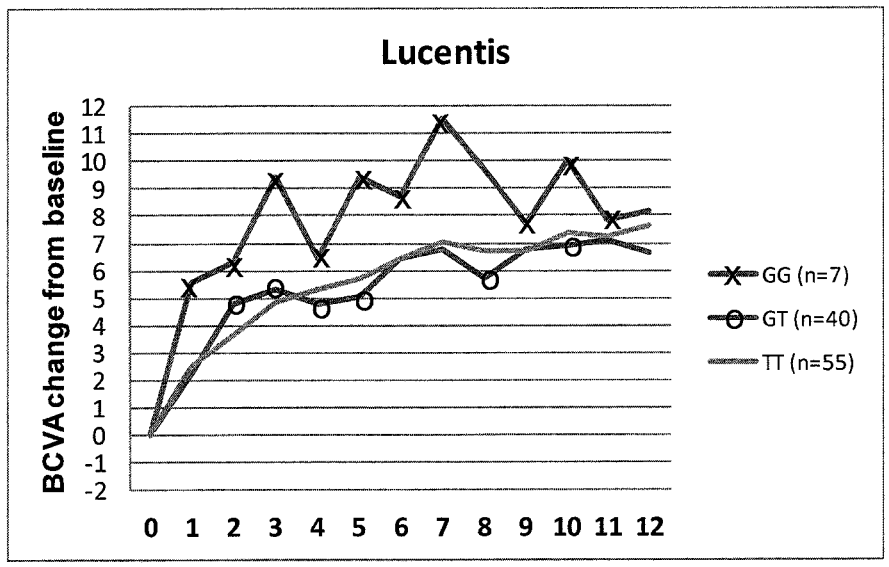
Figure 2   Effect of EPO genotype on BCVA response in DME patients treated with Lucentis and laser
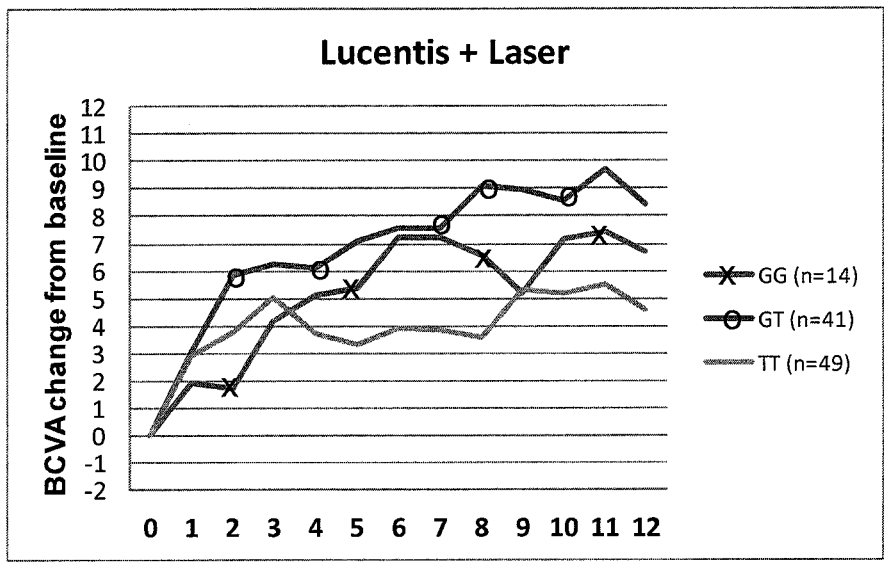

Figure 3      Effect of EPO genotype on BCVA response in DME patients treated with laser
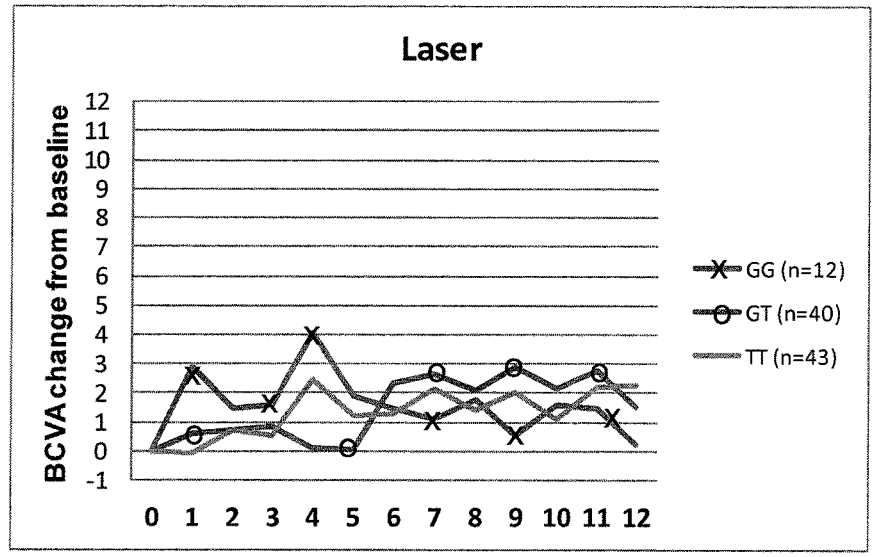
Figure 4      Effect of EPO genotype on BCVA response in AMD patients treated with Lucentis
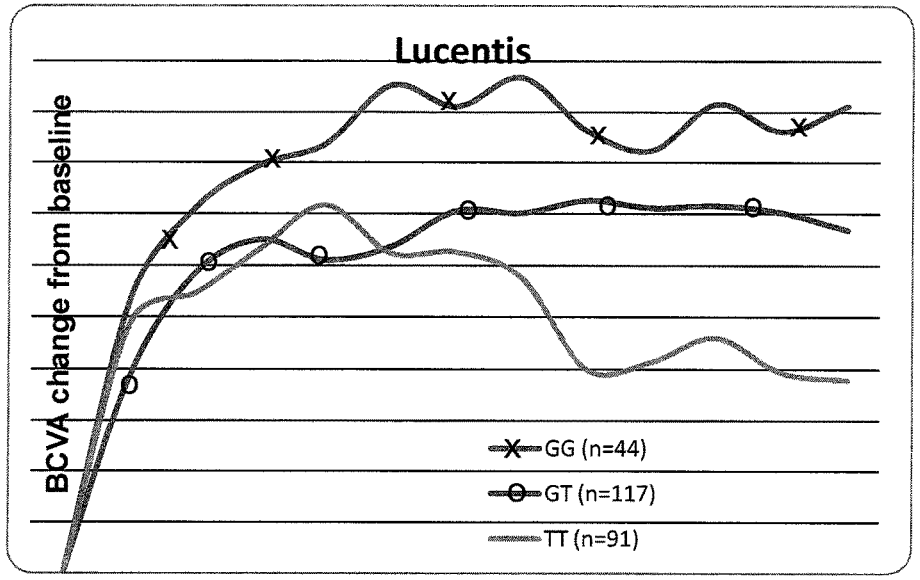
by pyrosequencing. Buccal cells may reflect the neuronal condition more accurately than blood, because lymphocytes originated from the mesoderm and both neurons and skin develop Figure 5   Effect of EPO genotype on BCVA response in AMD patients treated with Lucentis and laser
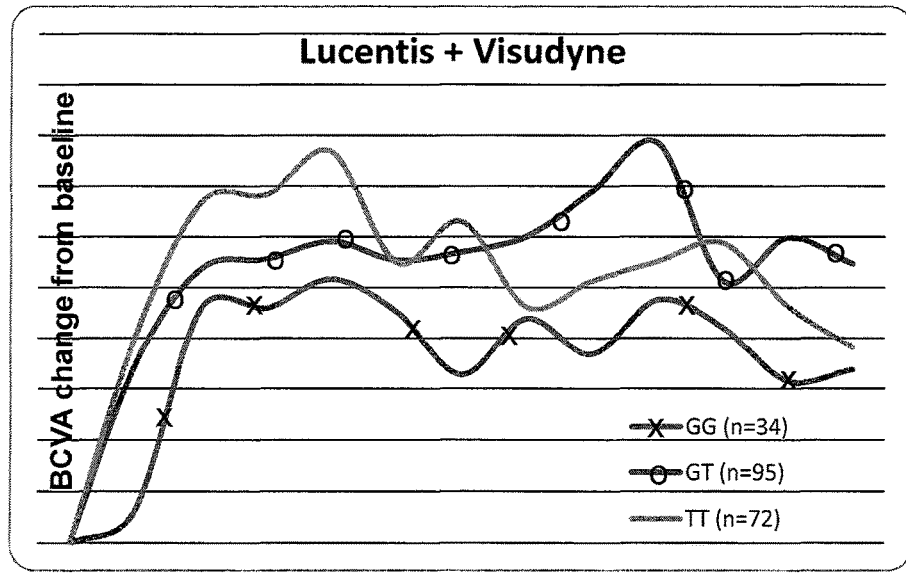
Figure 6   Effect of VEGF genotype on BCVA response in DME patients treated with Lucentis®
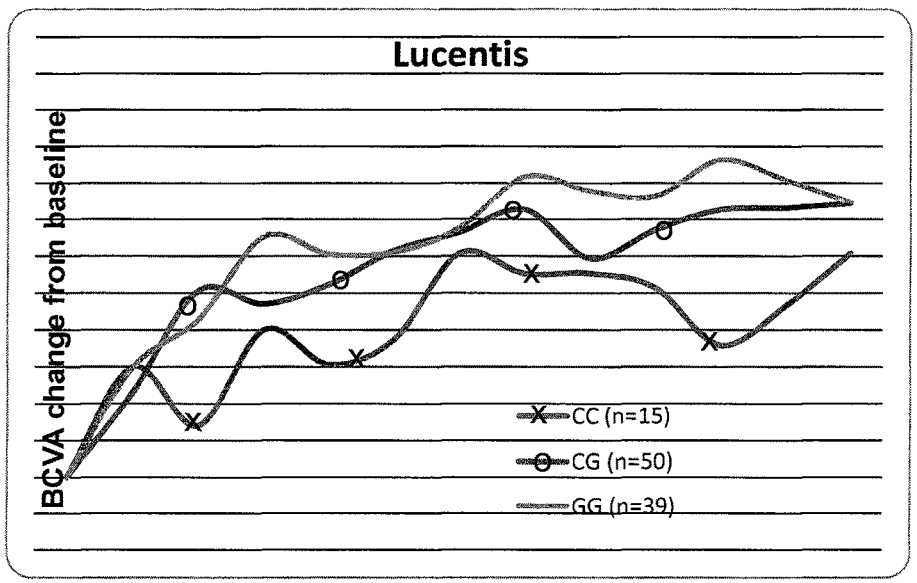

Figure 7    Effect of VEGF genotype on BCVA response in DME patients treated with Lucentis® and laser
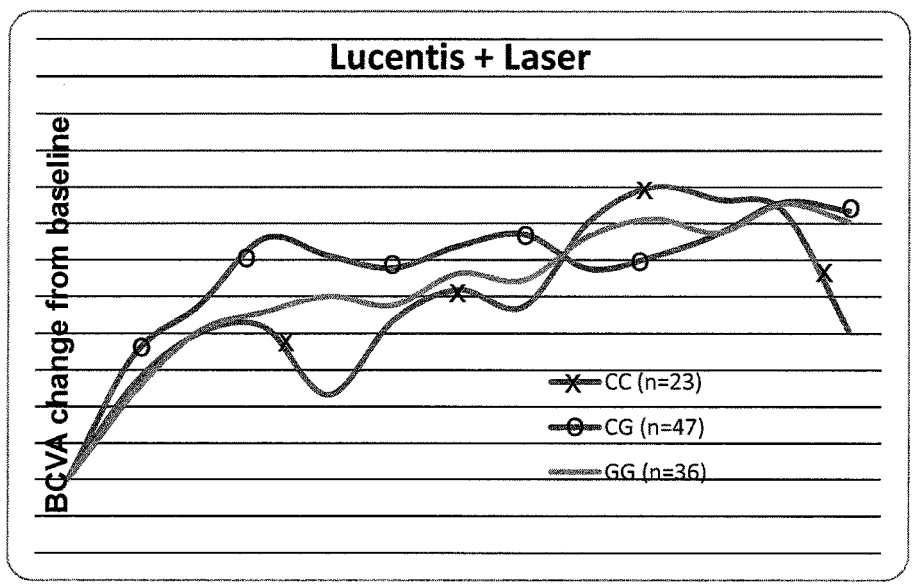
Figure 8    Effect of VEGF genotype on BCVA response in DME patients treated with laser
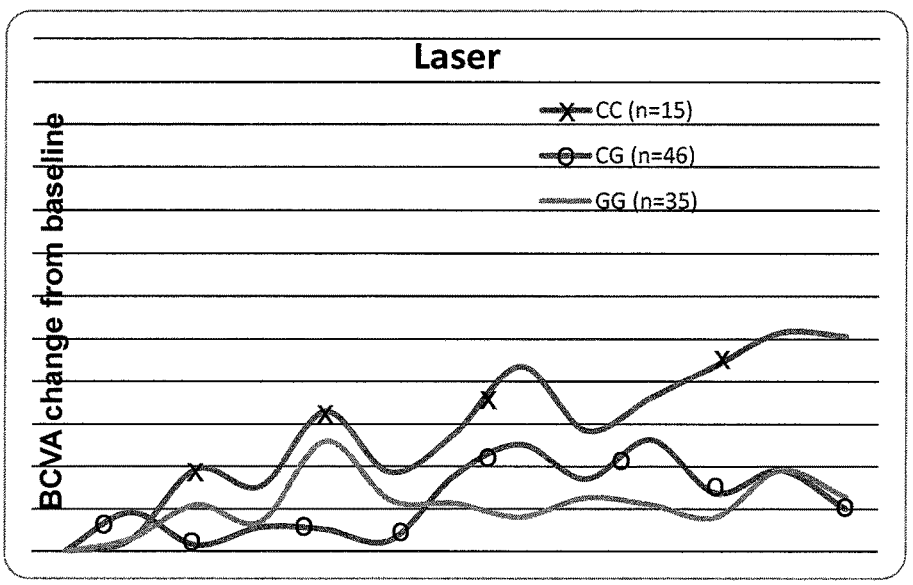

Figure 9    Effect of VEGF genotype on BCVA response in AMD patients treated with Lucentis®
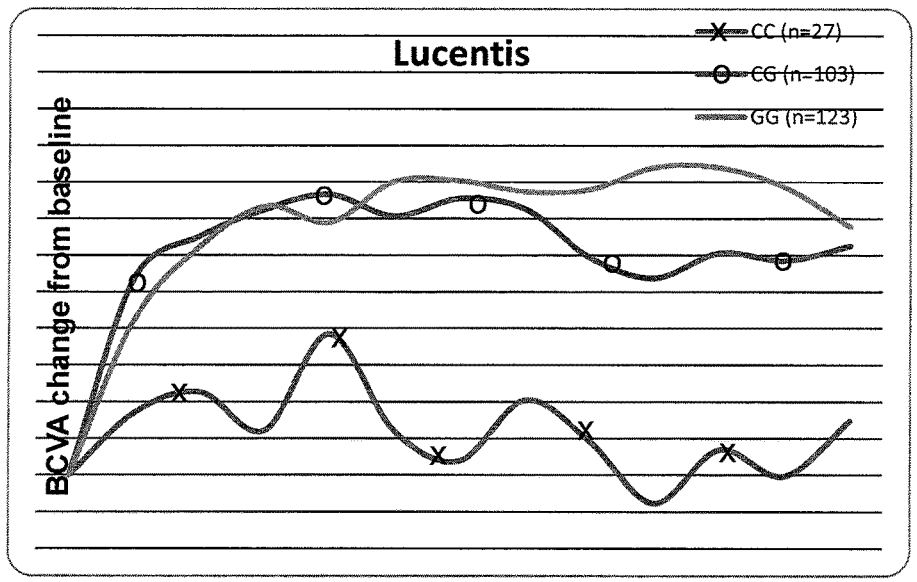
Figure 10   Effect of VEGF genotype on BCVA response in AMD patients treated with Lucentis® and laser
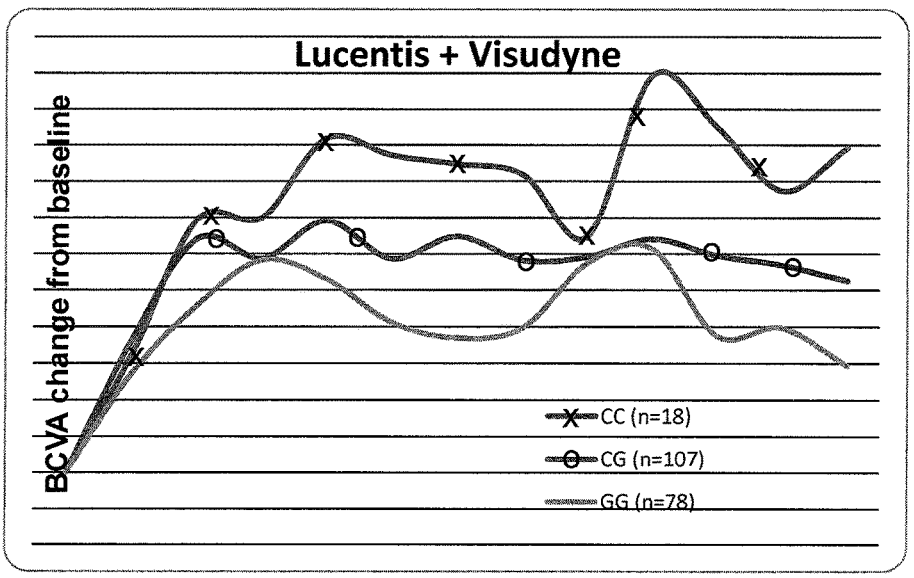

Figure 11     Additive effect of EPO and VEGF on BCVA response in AMD patients treated with Lucentis®
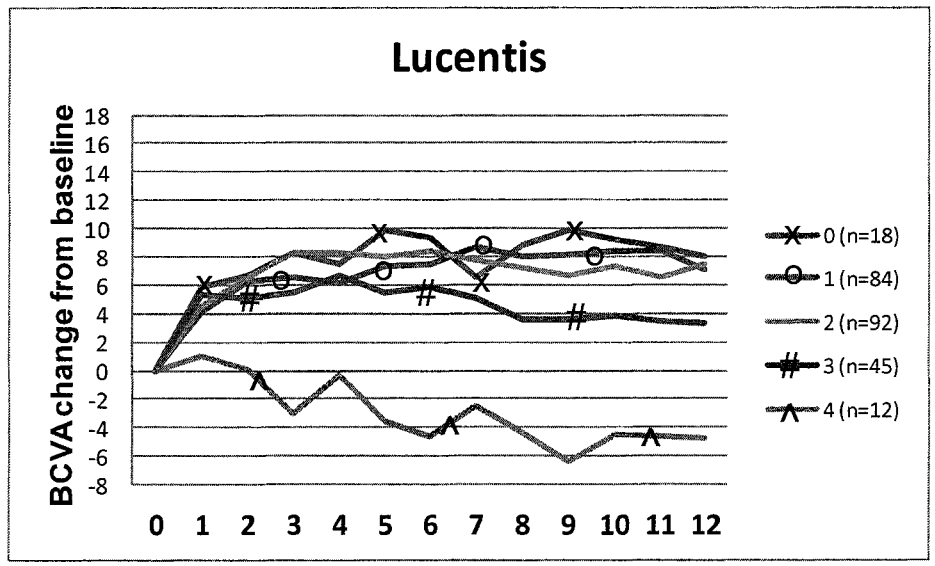
Figure 12     Additive effect of EPO and VEGF on BCVA response in AMD patients treated with Lucentis® and laser
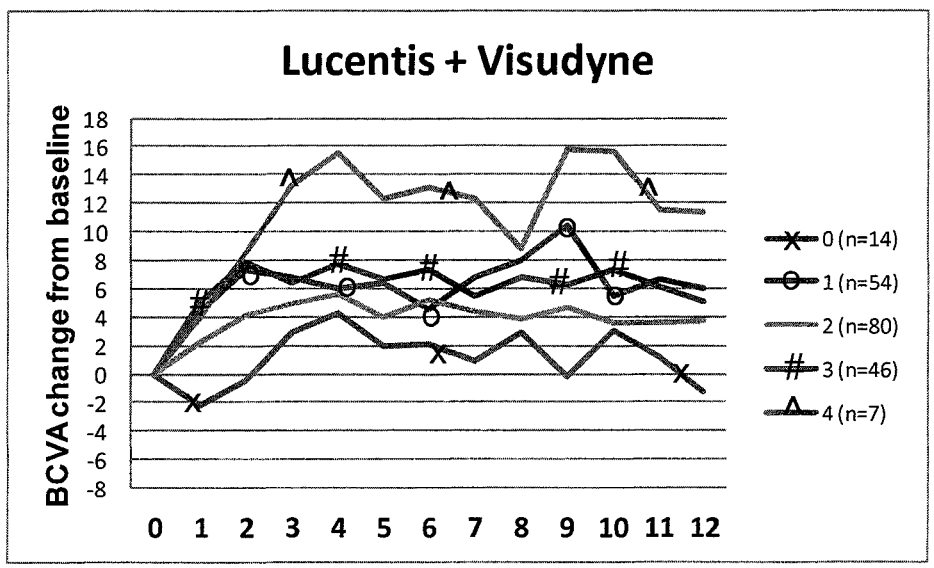

METHODS OF TREATING OPHTHALMIC DISORDERS

CROSS REFERENCE TO RELATED APPLICATION

This application claims priority to and is a continuation in-part of U.S. application Ser. No. 15/751,787, filed Feb. 9, 2018, which is a U.S. national phase application under 35 U.S.C. § 371 of International Application PCT/IB2016/054851, filed on Aug. 11, 2016, which claims benefit of U.S. Provisional Application No. 62/204,115, filed Aug. 12, 2015, the contents of which are hereby incorporated by reference in their entirety.

SEQUENCE LISTING

A sequence listing contained in the file named PAT056911-US-CNT SQL_ST25.txt which is 57,806 bytes in size and was created on Aug. 20, 2020, is filed electronically herewith and is hereby incorporated by reference in its entirety.

TECHNICAL FIELD

The disclosure is directed to predictive methods, personalized therapies, kits, transmittable forms of information and methods for treating patients having an ophthalmic disorder.

BACKGROUND OF THE INVENTION

Diabetic retinopathy (DR) is a microvascular complication of diabetes with a complex multifactorial pathogenesis. Accumulating evidence suggests a significant implication of genetic factors in the susceptibility to DR independent of glycemic control and the duration of diabetes. The most characterized genetic factor that is associated with the risk of DR is the functional polymorphism in the Erythropoietin (EPO) gene (rs1617640). This polymorphism is located in the EPO promoter region and the T allele was significantly associated with proliferative DR (PDR) in three European-American cohorts. The luciferase promoter assays showed that the T allele accounted for a 25-fold enhancement of the reporter expression as compared with the G allele. In addition, the EPO concentration in human vitreous body was 7.5-fold higher in normal subjects with homozygous TT genotype than in those with the GG genotype.

EPO is a potent angiogenic factor observed in the diabetic human and mouse eye. The EPO mRNA concentration is increased in the mouse model of ischemia-induced retinal neovascularization, and this neovascularization is suppressed by inhibition of EPO. EPO receptor immunoreactivity was strongly detected in neovascular tissues of PDR eyes.

BRIEF SUMMARY OF THE INVENTION

In one aspect, the invention features a method of selectively treating a patient having an ophthalmic disorder, including selectively administering a therapeutically effective amount of a VEGF antagonist to the patient on the basis of the patient having one or more ophthalmic response markers selected from the group including: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963.

In another aspect, the invention features a method of selectively treating a patient having an ophthalmic disorder, including selectively administering a therapeutically effective amount of an EPO antagonist or the combination of a VEGF antagonist and EPO antagonist to the patient on the basis of the patient having at least one allele having a thymine at the locus rs1617640 (e.g., two alleles having a thymine at the locus rs1617640).

In another aspect, the invention features a method of selectively treating a patient having an ophthalmic disorder with a VEGF antagonist, including:

a) selecting the patient for treatment with the VEGF antagonist on the basis of a the patient having one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963; and b) thereafter, administering a therapeutically effective amount of the VEGF antagonist to the patient.

In yet another aspect, the invention features a method of selectively treating a patient having an an ophthalmic disorder with an EPO antagonist or the combination of a VEGF antagonist and an EPO antagonist, including:

a) selecting the patient for treatment with the VEGF and EPO antagonist on the basis of a the patient having at least one allele (e.g., two alleles) having a thymine at the locus rs1617640; and b) thereafter, administering a therapeutically effective amount of the VEGF antagonist and/or EPO antagonist to the patient.

In a further aspect, the invention features a method of selectively treating a patient having an ophthalmic disorder with a VEGF antagonist, including:

a) assaying a biological sample from the patient for one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963; and b) thereafter, selectively administering to the patient the VEGF antagonist.

In another aspect, the invention features a method of selectively treating a patient having an ophthalmic disorder with an EPO antagonist or the combination of a VEGF antagonist and an EPO antagonist, including:

a) assaying a biological sample from the patient for at least one allele (e.g., two alleles) having a thymine at the locus rs1617640; and b) thereafter, selectively administering to the patient the VEGF antagonist and/or EPO antagonist.

In another aspect, the invention features a method of selectively treating a patient having an ophthalmic disorder with a VEGF antagonist, including:

a) assaying a biological sample from the patient for one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963;

b) thereafter, selecting the patient for treatment with the VEGF antagonist on the basis of the biological sample from the patient having one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963; and c) thereafter, administering a therapeutically effective amount of the VEGF antagonist.

In another aspect, the invention features a method of selectively treating a patient having an ophthalmic disorder with an EPO antagonist or the combination of a VEGF antagonist and an EPO antagonist:

a) assaying a biological sample from the patient for at least one allele (e.g., two alleles) having a thymine at the locus rs161764;

b) thereafter, selecting the patient for treatment with the combination of a VEGF antagonist and an EPO antagonist on the basis of the biological sample from the patient having at least one allele having a thymine at the locus rs161764; and c) thereafter, administering a therapeutically effective amount of the VEGF antagonist and/or EPO antagonist.

In another aspect, the invention features a VEGF antagonist for use in treating a patient having an ophthalmic disorder, characterized in that a therapeutically effective amount of the VEGF antagonist is to be administered to the patient on the basis of the patient having one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963.

In a related aspect, the invention features an EPO antagonist for use in treating a patient having an ophthalmic disorder, characterized in that a therapeutically effective amount of the EPO antagonist is to be administered to the patient on the basis of the patient having at least one allele (e.g., two alleles) having a thymine at the locus rs1617640.

In another aspect, the invention features a method of predicting the likelihood that a patient having an ophthalmic disorder will respond to treatment with a VEGF antagonist, including assaying a biological sample from the patient for the presence or absence one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963.

In another aspect, the invention features a method of predicting the likelihood that a patient having an ophthalmic disorder will respond to treatment with a combination of an EPO antagonist or the combination of a VEGF antagonist and EPO antagonist, including assaying a biological sample from the patient for the presence or absence of at least one allele (e.g., two alleles) having a thymine at the locus rs1617640.

In yet another aspect, the invention features a method for producing a transmittable form of information for predicting the responsiveness of a patient having an ophthalmic disorder to treatment with a VEGF antagonist, including determining an increased likelihood of the patient responding to treatment with VEGF antagonist based on the presence of one or more ophthalmic response markers selected from the group including of: a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963 and recording the result of the determining step on a tangible or intangible media form for use in transmission.

In yet another aspect, the invention features a method for producing a transmittable form of information for predicting the responsiveness of a patient having an ophthalmic disorder to treatment with an EPO antagonist or the combination of a VEGF antagonist and an EPO antagonist, including determining an increased likelihood of the patient responding to treatment with an EPO antagonist or combination of a VEGF antagonist and an EPO antagonist based on the presence of at least one allele (e.g., two alleles) having a thymine at the locus rs1617640 and recording the result of the determining step on a tangible or intangible media form for use in transmission.

In yet another embodiment, the invention features a method of determining the responsiveness of an individual with a retinal disorder to treatment with a VEGF antagonist, the method including:

(i) isolating a sample from an individual having a retinal disorder;

(ii) performing an assay that detects the presence of one or more ophthalmic response markers selected from a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963;

(iii) assigning the individual as a VEGF antagonist responder if one or more of the ophthalmic response markers are present in the sample.

Also, the invention features a method of determining the responsiveness of an individual with a retinal disorder to treatment with a EPO antagonist, the method including:

(i) isolating a sample from an individual having a retinal disorder;

(ii) performing an assay that detects the presence of at least one allele having a thymine at the locus rs1617640;

(iii) assigning the individual as a EPO antagonist responder if the ophthalmic response markers are present in the sample.

Furthermore, certain aspects of the invention features a method for determining whether a subject with a retinal disorder should be treated with a VEGF antagonist, the method including:

(i) isolating a sample from the subject;

(ii) performing an assay that detects the presence of at least one allele having a thymine at the locus rs1617640;

(iii) determining that the subject should be treated with a VEGF antagonist.

In another aspect, the invention features a method for determining whether a subject with a retinal disorder should be treated with a VEGF antagonist, the method including:

(i) isolating a sample from the subject;

(ii) performing an assay that detects the presence of one or more ophthalmic response markers selected from a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963;

(iii) determining that the subject should be treated with a VEGF antagonist.

Also, the invention features, in certain aspects, a kit for predicting the response to a VEGF antagonist, the kit including reagents necessary for detecting the presence of one or more ophthalmic response markers selected from a single allele having a nucleotide other than a thymine at the locus rs1617640, two alleles having a nucleotide other than a thymine at the locus rs1617640, a single allele having a guanine at the locus rs2010963, and two alleles having a guanine at the locus rs2010963.

Finally, in certain aspects, the invention features a kit for predicting the response to a VEGF antagonist, the kit including reagents necessary for detecting the presence of at least one allele (e.g., two alleles) having a thymine at the locus rs1617640.

The above methods can, optionally, further include the step of obtaining the biological sample from the patient, wherein the step of obtaining is performed prior to the step of detecting. Any of the foregoing assaying steps can preferably include assaying the biological sample for a genomic sequence including the locus rs161764 and/or the locus rs2010963. Such assaying can be, e.g., polymerase chain reaction (PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, SNPLEX® (SNP detecting system available from Applied Biosystems), capillary electrophoresis, Southern Blot, flow cytometry, HPLC, and mass spectrometry Biological samples can include, e.g., synovial fluid, blood, serum, feces, plasma, urine, tear, saliva, cerebrospinal fluid, a leukocyte sample and a tissue sample.

In any of the foregoing methods the ophthalmic disorder is macular degeneration (e.g., age-related macular degeneration), diabetic macular edema, or diabetic retinopathy. Also, in any of the foregoing methods, the VEGF antagonist is a VEGF binding molecule or VEGF (e.g., VEGFA) receptor binding molecule. VEGF (e.g., VEGFA) binding molecules can be, e.g., an anti-VEGFA antibody or antigen-binding portion or derivative thereof (e.g., bevacizumab or ranibizumab, an antibody or antigen-binding portion or derivative thereof selected from the group including of: NVS4, NVS80, NVS81, NVS82, NVS83, NVS84 and NVS85 as described in U.S. Patent Application Publication 20120014958 or the VEGFA antibody or antigen-binding portion or derivative thereof described in U.S. Patent Application Publication 20140186350.

Furthermore, the anti-EPO antagonist of the foregoing methods can be, e.g., an antibody or antigen-binding portion or derivative thereof, e.g., an antibody or antigen-binding portion or derivative thereof having the CDR sequences of Fabs NVS1, NVS2, NVS3, or NVS4 (including antibodies or derivatives thereof including the Fabs NVS1-4) as disclosed in U.S. Patent Application Publication No. 2014/0199306.

BRIEF DESCRIPTION OF THE DRAWINGS

FIG. 1 is a graph showing the effect of EPO genotype on BCVA response in DME patients treated with LUCENTIS® (ranibizumab).

FIG. 2 is a graph showing the effect of EPO genotype on BCVA response in DME patients treated with LUCENTIS® (ranibizumab) and laser.

FIG. 3 is a graph showing the effect of EPO genotype on BCVA response in DME patients treated with laser.

FIG. 4 is a graph showing the effect of EPO genotype on BCVA response in AMD patients treated with LUCENTIS® (ranibizumab).

FIG. 5 is a graph showing the effect of EPO genotype on BCVA response in AMD patients treated with LUCENTIS® (ranibizumab) and laser.

FIG. 6 is a graph showing the effect of VEGF genotype on BCVA response in DME patients treated with LUCENTIS® (ranibizumab).

FIG. 7 is a graph showing the effect of VEGF genotype on BCVA response in DME patients treated with LUCENTIS® (ranibizumab) and laser.

FIG. 8 is a graph showing the effect of VEGF genotype on BCVA response in DME patients treated with laser.

FIG. 9 is a graph showing the effect of VEGF genotype on BCVA response in AMD patients treated with LUCENTIS® (ranibizumab).

FIG. 10 is a graph showing the effect of VEGF genotype on BCVA response in AMD patients treated with LUCENTIS® (ranibizumab) and laser.

FIG. 11 is a graph showing the additive effect of EPO and VEGF genotypes on BCVA response in AMD patients treated with LUCENTIS® (ranibizumab).

FIG. 12 is a graph showing the additive effect of EPO and VEGF genotypes on BCVA response in AMD patients treated with LUCENTIS® (ranibizumab) and laser.

DETAILED DESCRIPTION OF THE INVENTION

The present invention is based, in part, on the discovery that certain genomic markers (herein referred to as "ophthalmic response markers") are predictive with respect to the outcome of anti-VEGF therapy in the treatment of ophthalmic disorders (e.g., LUCENTIS® (ranibizumab)). In particular, the present inventors have discovered that a polymorphism in the promoter for human erythropoietin is predictive for the efficacy of anti-VEGF therapy. Furthermore, the inventors have discovered that the presence of a particular polymorphism in the 5' UTR of VEGF alone, or in combination with the EPO polymorphism, provide additional information regarding the predicted response to anti-VEGF therapy. Thus, the invention features methods of identifying patients as being likely to respond to anti-VEGF therapy. Furthermore, in those patients identified as failing to include one or more of the above ophthalmic response markers, the invention features treatment with an EPO antagonist (e.g., alone, or in combination with a VEGF antagonist).

Specifically, the invention is based in part on the observation that treatment (e.g., in a subject with age-related macular degeneration) with a VEGF antagonist alone is more efficacious in patients having at least one allele having a nucleotide other than a thymine at the locus rs1617640. Furthermore, treatment with a VEGF antagonist in such patients is even more effective where the patient has two alleles having a nucleotide other than a thymine at the locus rs1617640. The invention is also based on part on the observation that a polymorphism in the VEGF [5' UTR] is a further predictor of the efficacy of anti-VEGF monotherapy. In such cases the presence of a single allele having a guanine at the locus rs2010963 suggests an increased efficacy of VEGF monotherapy treatment while two alleles having this guanine suggests an even greater efficacy. Finally, the invention is based on the observation that, collectively, the presence of the above polymorphisms at the locuses rs1617640 and rs2010963 (in, e.g., 2, 3, or all 4 alleles) represents a greater likelihood of efficacy of anti-VEGF monotherapy when compared to individuals without a combination of both polymorphisms.

Additionally, the invention features the prediction that the presence of a thymine in one or more alleles at the locus rs1617640 of a patient is suggestive of the efficacy of treatment with an EPO antagonist. Here, the invention features treating such patients (e.g., those with age-related macular degeneration) with either an EPO antagonist alone, or with an EPO antagonist in combination with a VEGF antagonist.

The term "about" in relation to a numerical value x means+/−10% unless the context dictates otherwise.

As used herein, the terms "subject" and "patient" include any human.

The term "assaying" is used to refer to the act of identifying, screening, probing, testing measuring or determining, which act may be performed by any conventional means. For example, a sample may be assayed for the presence of a particular genetic marker by using an ELISA assay, a Northern blot, imaging, gene sequencing, phenotyping, haplotyping, mass spectrometry, etc. The term "detecting" (and the like) means the act of extracting particular information from a given source, which may be direct or indirect. In some embodiments of the predictive methods disclosed herein, the presence of a given thing (e.g., allele, etc.) is detected in a biological sample indirectly, e.g., by querying a database. The terms "assaying" and "determining" contemplate a transformation of matter, e.g., a transformation of a biological sample, e.g., a blood sample or other tissue sample, from one state to another by means of subjecting that sample to physical testing.

The term "obtaining" means to procure, e.g., to acquire possession of in any way, e.g., by physical intervention (e.g., biopsy, blood draw) or non-physical intervention (e.g, transmittal of information via a server), etc.

The phrase "assaying a biological sample . . . " and the like, is used to mean that a sample may be tested (either directly or indirectly) for either the presence or absence of a given ophthalmic response marker. It will be understood that, in a situation where the presence of a substance denotes one probability and the absence of a substance denotes a different probability, then either the presence or the absence of such substance may be used to guide a therapeutic decision. For example, one may determine if a patient has ophthalmic response marker by determining the actual existence of particular response allele in the patient or by determining the absence of the particular response allele in the patient. In both such cases, one has determined whether the patient has the presence of the ophthalmic response marker.

The term "VEGF" refers to human VEGF-A, and includes polymorphic variants of VEGF-A, and functional equivalents of VEGF-A. Functional equivalents of VEGF-A according to the present disclosure preferably have at least about 85%, 95%, 96%, 97%, 98%, or even 99% overall sequence identity with a wild-type VEGFA.

"VEGF antagonist" as used herein refers to a molecule capable of antagonizing (e.g., reducing, inhibiting, decreasing, delaying) VEGF function, expression and/or signalling (e.g., by blocking the binding of VEGF to the VEGF receptor). Non-limiting examples of VEGF antagonists include VEGF binding molecules and VEGF receptor binding molecules. In some embodiments of the disclosed methods, regimens, kits, processes, uses and compositions, a VEGF antagonist is employed.

By "VEGF binding molecule" is meant any molecule capable of binding to the human VEGF antigen either alone or associated with other molecules. The binding reaction may be shown by standard methods (qualitative assays) including, for example, a binding assay, competition assay or a bioassay for determining the inhibition of VEGF binding to its receptor or any kind of binding assays, with reference to a negative control test in which an antibody of unrelated specificity, but ideally of the same isotype. Non-limiting examples of VEGF binding molecules include small molecules, VEGF receptor decoys, and antibodies that bind to VEGF as produced by B-cells or hybridomas and chimeric, CDR-grafted or human antibodies or any fragment thereof, e.g., F(ab')2 and Fab fragments, as well as single chain or single domain antibodies. Preferably the VEGF binding molecule antagonizes (e.g., reduces, inhibits, decreases, delays) VEGF function, expression and/or signalling. In some embodiments of the disclosed methods, regimens, kits, processes, uses and compositions, an VEGF binding molecule is employed.

By "VEGF receptor binding molecule" is meant any molecule capable of binding to the human VEGF receptor either alone or associated with other molecules. The binding reaction may be shown by standard methods (qualitative assays) including, for example, a binding assay, competition assay or a bioassay for determining the inhibition of VEGF receptor binding to VEGF or any kind of binding assays, with reference to a negative control test in which an antibody of unrelated specificity, but ideally of the same isotype is used. Non-limiting examples of VEGF receptor binding molecules include small molecules, VEGF decoys, and antibodies to the VEGF receptor as produced by B-cells or hybridomas and chimeric, CDR-grafted or human antibodies or any fragment thereof, e.g., F(ab')2 and Fab fragments, as well as single chain or single domain antibodies. Preferably the VEGF receptor binding molecule antagonizes (e.g., reduces, inhibits, decreases, delays) VEGF function, expression and/or signalling. In some embodiments of the disclosed methods, regimens, kits, processes, uses and compositions, a VEGF receptor binding molecule is employed.

The terms "Epo protein" or "Epo antigen" or "EPO" or "Epo" are used interchangeably, and refer to the erythropoietin protein in different species. The protein sequences for human, cynomolgus, mouse, rat, and rabbit Epo are publicly available. Human EPO can also be hyperglycosylated.

The terms "Epo Receptor" or "EPOR" are used interchangeably, and refer to the erythropoietin receptor protein, and refer to the erythropoietin receptor protein in different species. EPOR has been described by Winkelmann J. C., Penny L. A., Deaven L. L., Forget B. G., Jenkins R. B. Blood 76:24-30 (1990).

"EPO antagonist" as used herein refers to a molecule capable of antagonizing (e.g., reducing, inhibiting, decreasing, delaying) EPO function, expression and/or signalling (e.g., by blocking the binding of EPO to the EPO receptor). Non-limiting examples of EPO antagonists include EPO binding molecules and EPO receptor binding molecules. In some embodiments of the disclosed methods, regimens, kits, processes, uses and compositions, a EPO antagonist is employed.

By "EPO binding molecule" is meant any molecule capable of binding to the human EPO antigen either alone or associated with other molecules. The binding reaction may be shown by standard methods (qualitative assays) including, for example, a binding assay, competition assay or a bioassay for determining the inhibition of EPO binding to its receptor or any kind of binding assays, with reference to a negative control test in which an antibody of unrelated specificity, but ideally of the same isotype. Non-limiting examples of VEGF binding molecules include small molecules, VEGF receptor decoys, and antibodies that bind to VEGF as produced by B-cells or hybridomas and chimeric, CDR-grafted or human antibodies or any fragment thereof, e.g., F(ab')2 and Fab fragments, as well as single chain or single domain antibodies. Preferably the VEGF binding molecule antagonizes (e.g., reduces, inhibits, decreases, delays) VEGF function, expression and/or signalling. In some embodiments of the disclosed methods, regimens, kits, processes, uses and compositions, a VEGF binding molecule is employed.

The term "antibody" as referred to herein includes whole antibodies and any antigen-binding portion or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some embodiments of the disclosed methods, regimens, kits, processes, uses and compositions, an antibody to VEGF, EPO, VEGF receptor or EPO receptor is employed, preferably an antibody to VEGF or EPO.

The term "antigen-binding portion" of an antibody as used herein, refers to fragments of an antibody that retain the ability to specifically bind to an antigen (e.g., VEGF or EPO). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art. In some embodiments of the disclosed methods, regimens, kits, processes, uses and compositions, a single chain antibody or an antigen-binding portion of an antibody against VEGF or EPO is employed.

An "isolated antibody", as used herein, refers to an antibody that is substantially free of other antibodies having different antigenic specificities. The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo).

Please replace the paragraph on page 15 with the following amended paragraph:

The term "$K_D$" is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a BIACORE® (biomolecular interaction measurement) system.

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward VEGF or EPO of various species are known in the art, including for example, ELISAs, western blots and RIAs. The binding kinetics (e.g., binding affinity) of the antibodies also can be assessed by standard assays known in the art, such as by Biacore analysis.

An antibody that "inhibits" one or more of these VEGF or EPO functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits VEGF or EPO activity affects a statistically significant decrease, e.g., by at least about 10% of the measured parameter, by at least 50%, 80% or 90%, and in certain embodiments of the disclosed methods, uses, processes, kits and compositions, the VEGF or EPO antibody used may inhibit greater than 95%, 98% or 99% of VEGF or EPO functional activity.

The term "derivative", unless otherwise indicated, is used to define amino acid sequence variants, and covalent modifications (e.g., pegylation, deamidation, hydroxylation, phosphorylation, methylation, etc.) of an VEGF or EPO antagonist. A "functional derivative" includes a molecule having a qualitative biological activity in common with the disclosed VEGF or EPO antagonists. A functional derivative includes fragments and peptide analogs of a VEGF or EPO antagonist as disclosed herein. Fragments comprise regions within the sequence of a polypeptide according to the present disclosure, e.g., of a specified sequence. Functional derivatives of the VEGF and EPO antagonists disclosed herein preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the VEGF or EPO binding molecules disclosed herein, and substantially retain the ability to bind human VEGF or EPO.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions (e.g., conservative substitutions, such as swapping a serine for a threonine, or substitutions at positions not involved in antibody activity, structural integrity, complement fixation, etc.) in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this disclosure. In some embodiments, the sequence identity of a derivative VEGF or EPO antibody can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "pharmaceutically acceptable" means a non-toxic material that does not interfere with the effectiveness of the biological activity of the active ingredient(s).

The term "administering" in relation to a compound, e.g., a VEGF or EPO binding molecule or another agent, is used to refer to delivery of that compound to a patient by any route.

As used herein, a "therapeutically effective amount" refers to an amount of a VEGF or EPO antagonist that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient administered alone, the term refers to that ingredient alone. When applied to a combination, the term refers to combined amounts of the active ingredients that result in the therapeutic effect, whether administered in combination, serially or simultaneously.

As used herein, the term "treating" or "treatment" of any conditions or disorders associated with retinal vascular disease, conditions or disorders associated with diabetic retinopathy, and/or conditions or disorders associated with macular edema refers in one aspect, to ameliorating the disease or disorder (i.e., slowing or arresting or reducing the development of the disease or at least one of the clinical symptoms thereof). In another aspect "treating" or "treatment" refers to alleviating or ameliorating at least one physical parameter including those which may not be discernible by the patient. In yet another aspect, "treating" or "treatment" refers to modulating the disease or disorder, either physically, (e.g., stabilization of a discernible symptom), physiologically, (e.g., stabilization of a physical parameter), or both. In yet another aspect, "treating" or "treatment" refers to preventing or delaying the onset or development or progression of the disease or disorder. "Prevention" as it relates to indications described herein, including, conditions or disorders associated with retinal vascular disease, conditions or disorders associated with diabetic retinopathy, and/or conditions or disorders associated with macular edema, means any action that prevents or slows a worsening in visual function, retinal anatomy, retinal vascular disease parameter, diabetic retinopathy disease parameter, and/or macular edema disease parameter, as described below, in a patient at risk for said worsening. More specifically, "treatment" of conditions or disorders associated with retinal vascular disease, conditions or disorders associated with diabetic retinopathy, and/or conditions or disorders associated with macular edema means any action that results in, or is contemplated to result in, the improvement or preservation of visual function and/or retinal anatomy. Methods for assessing treatment and/or prevention of disease are known in the art and described herein below.

The phrase "respond to treatment" is used to mean that a patient, upon being delivered a particular treatment shows a clinically meaningful benefit from said treatment. The phrase "respond to treatment" is meant to be construed comparatively, rather than as an absolute response. For example, an ophthalmic patient having an ophthalmic response marker is predicted to have more benefit from treatment with a VEGF antagonist than an ophthalmic patient who does not have the ophthalmic response marker. These carriers of ophthalmic response markers respond more favorably to treatment with the VEGF antagonist, and may simply be said to "respond to treatment" with a VEGF antagonist.

The phrase "receiving data" is used to mean obtaining possession of information by any available means, e.g., orally, electronically (e.g., by electronic mail, encoded on diskette or other media), written, etc.

As used herein, "selecting" and "selected" in reference to a patient is used to mean that a particular patient is specifically chosen from a larger group of patients on the basis of (due to) the particular patient having a predetermined criteria, e.g., the patient has an ophthalmic response marker. Similarly, "selectively treating" refers to providing treatment to a patient having a particular disease, where that patient is specifically chosen from a larger group of patients on the basis of the particular patient having a predetermined criteria. Similarly, "selectively administering" refers to administering a drug to a patient that is specifically chosen from a larger group of patients on the basis of (due to) the particular patient having a predetermined criteria, e.g., a particular genetic or other biological marker. By selecting, selectively treating and selectively administering, it is meant that a patient is delivered a personalized therapy based on the patient's particular biology, rather than being delivered a standard treatment regimen based solely on the patient having a particular disease. Selecting, in reference to a method of treatment as used herein, does not refer to fortuitous treatment of a patient that has, e.g., an ophthalmic response marker, but rather refers to the deliberate choice to administer a VEGF antagonist to a patient based on the patient having an ophthalmic response marker. Thus, selective treatment differs from standard treatment, which delivers a particular drug to all patients, regardless of their allelic status.

As used herein, "predicting" indicates that the methods described herein provide information to enable a health care provider to determine the likelihood that an individual having an ophthalmic disease selected from retinal vascular disease, macular edema, diabetic retinopathy, diabetic macular edema, proliferative diabetic retinopathy, and VEGF-mediated disorders will respond to or will respond more favorably to treatment with a VEGF and/or EPO binding molecule. It does not refer to the ability to predict response with 100% accuracy. Instead, the skilled artisan will understand that it refers to an increased probability.

As used herein, "likelihood" and "likely" is a measurement of how probable an event is to occur. It may be used interchangably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued, or treatment proceed with a dosage increase) with the VEGF and/or EPO binding molecules or the patient may not be treated (or treatment discontinued, or treatment proceed with a lowered dose) with the VEGF and/or EPO binding molecules.

The phrase "increased likelihood" refers to an increase in the probability that an event will occur. For example, some methods herein allow prediction of whether a patient will display an increased likelihood of responding to treatment with a VEGF and/or EPO binding molecule or an increased likelihood of responding better to treatment with a VEGF and/or EPO binding molecule in comparison to a patient having an ophthalmic disease selected from retinal vascular disease, macular edema, diabetic retinopathy, diabetic macular edema, proliferative diabetic retinopathy, and VEGF-mediated disorders who does not have a particular genotype (e.g., an ophthalmic response marker).

As used herein "SNP" refers to "single nucleotide polymorphism". A single nucleotide polymorphism is a DNA sequence variation occurring when a single nucleotide in the genome (or other shared sequence) differs between members of a biological species or paired chromosomes in an individual. Most SNPs have only two alleles, and one is usually more common in the population. A SNP may be present in an exon or an intron of a gene, an upstream or downstream untranslated region of a gene, or in a purely genomic location (i.e., non-transcribed). When a SNP occurs in the coding region of a gene, the SNP may be silent (i.e., a synonymous polymorphism) due to the redundancy of the genetic code, or the SNP may result in a change in the sequence of the encoded polypeptide (i.e., a non-synonymous polymorphism). In the instant disclosure, SNPs are identified by their Single Nucleotide Polymorphism Database (dbSNP) rs number, e.g., "rs1617640" or "rs2010963". The dbSNP is a free public archive for genetic variation within and across different species developed and hosted by the National Center for Biotechnology Information (NCBI) in collaboration with the National Human Genome Research Institute (NHGRI).

A polymorphic site, such as a SNP, is usually preceded by and followed by conserved sequences in the genome of the population of interest and thus the location of a polymorphic site can often be made in reference to a consensus nucleic acid sequence (e.g., of thirty to sixty nucleotides) that bracket the polymorphic site, which in the case of a SNP is commonly referred to as the "SNP context sequence". Context sequences for the SNPs disclosed herein may be found in the NCBI SNP database available at: www.ncbi.nlm.nih.gov/snp. Alternatively, the location of the polymorphic site may be identified by its location in a reference sequence (e.g., GeneBank deposit) relative to the start of the gene, mRNA transcript, BAC clone or even relative to the initiation codon (ATG) for protein translation. The skilled artisan understands that the location of a particular polymorphic site may not occur at precisely the same position in a reference or context sequence in each individual in a population of interest due to the presence of one or more insertions or deletions in that individual's genome as compared to the consensus or reference sequence. It is routine for the skilled artisan to design robust, specific and accurate assays for detecting the alternative alleles at a polymorphic site in any given individual, when the skilled artisan is provided with the identity of the alternative alleles at the polymorphic site to be detected and one or both of a reference sequence or context sequence in which the polymorphic site occurs. Thus, the skilled artisan will understand that specifying the location of any polymorphic site described herein by reference to a particular position in a reference or context sequence (or with respect to an initiation codon in such a sequence) is merely for convenience and that any specifically enumerated nucleotide position literally includes whatever nucleotide position the same polymorphic site is actually located at in the same locus in any individual being tested for the genetic marker of the invention using any of the genotyping methods described herein or other genotyping methods known in the art.

In addition to SNPs, genetic polymorphisms include translocations, insertions, substitutions, deletions, etc., that occur in gene enhancers, exons, introns, promoters, 5' UTR, 3'UTR, etc.

As used herein "rs1617640" refers to an SNP located within the promoter of the human EPO gene. The rs1617640 polymorphic site is located at chromosomal position [chr7:100719675] (build [107]; assembly [GRCh38.p2]), which is position [38212896] of Contig NT_007933.16].

As used herein "rs2010963" refers to an SNP located within the [5' UTR] of the human VEGFA gene. The rs2010963 polymorphic site is located at chromosomal position [chr6:43770613] (build [107]; assembly [GRCh38.p2]), which is position [43710613] of Contig [NT_007592.16].

As recognized by the skilled artisan, nucleic acid samples containing a particular SNP may be complementary double stranded molecules and thus reference to a particular site on the sense strand refers as well to the corresponding site on the complementary antisense strand. Similarly, reference to a particular genotype obtained for a SNP on both copies of one strand of a chromosome is equivalent to the complementary genotype obtained for the same SNP on both copies of the other strand.

As used herein, "genomic sequence" refers to a DNA sequence present in a genome, and includes a region within an allele, an allele itself, or a larger DNA sequence of a chromosome containing an allele of interest.

The term "probe" refers to any composition of matter that is useful for specifically detecting another substance. A probe can be an oligonucleotide (including a conjugated oligonucleotide) that specifically hybridizes to a genomic sequence of an ophthalmic response marker, or a nucleic acid product of an ophthalmic response marker. A conjugated oligonucleotide refers to an oligonucleotide covalently bound to chromophore or molecules containing a ligand (e.g., an antigen), which is highly specific to a receptor molecule (e.g., an antibody specific to the antigen). The probe can also be a PCR primer, e.g., together with another primer, for amplifying a particular region within an ophthalmic response marker. Further, the probe can be an antibody that specifically binds to polypeptide products of these alleles. In preferred embodiments, the probe specifically hybridizes to a nucleic acid sequence (preferably genomic DNA) or specifically binds to a polypeptide sequence of an allele of interest.

The phrase "specifically hybridizes" is used to refer to hybridization under stringent hybridization conditions. Stringent conditions are known to those skilled in the art and can be found in Current Protocols in Molecular Biology, John Wiley & Sons, N.Y. (1989), 6.3.1-6.3.6. Aqueous and non-aqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5 M sodium phosphate, 7% SDS at 65° C., followed by at least one wash at 0.2×SSC, 1% SDS at 65° C.

The phrase "a region of a nucleic acid" is used to indicate a smaller sequence within a larger sequence of nucleic acids. For example, a gene is a region of a chromosome, an exon is a region of a gene, etc.

The term "specifically binds" in the context of polypeptides is used to mean that a compound binds a given polypeptide target (e.g., VEGF or EPO) rather than randomly binding undesireable polypeptides. However, "specifically binds" does not exclude some cross reactivity with undesireable polypeptides, as long as that cross reactivity does not interfere with the capability of the probe to provide a useful measure of the presence of the given polypeptide target.

The term "capable" is used to mean that ability to achieve a given result, e.g., a probe that is capable of detecting the presence of a particular substance means that the probe may be used to detect the particular substance.

An "oliogonucelotide" refers to a short sequence of nucleotides, e.g., 2-100 bases.

The term "biological sample" as used herein refers to a sample from a patient, which may be used for the purpose of identification, diagnosis, prediction, or monitoring. Preferred samples include synovial fluid, blood, blood-derived product (such as buffy coat, serum, and plasma), lymph, urine, tear, saliva, hair bulb cells, cerebrospinal fluid, buccal swabs, feces, synovial fluid, synovial cells, sputum, or tissue samples (e.g., cartilage samples). In addition, one of skill in the art would realize that some samples would be more readily analyzed following a fractionation or purification procedure, for example, isolation of DNA from whole blood.

VEGF Antagonists

The various disclosed pharmaceutical compositions, regimens, processes, uses, methods and kits utilize a VEGF antagonist, e.g., VEGF binding molecule (e.g., VEGF antibody or antigen-binding portion thereof, e.g., ranibizumab (LUCENTIS®)) or VEGF receptor binding molecule (e.g., VEGF receptor antibody or antigen-binding portion thereof). VEGF antagonists include ranibizumab (Ferrara N et al., Retina. 2006 October; 26(8): 859-70), bevacizumab (Ferrara N et al, Nat Rev Drug Discov. 2004 May; 3(5): 391-400.), aflibercept (Stewart M W et al, Nat Rev Drug Discov. 2012 Mar. 30; 11(4):269-70.), KH902 (Zhang M et al, Mol. Vis. 2008 Jan. 10; 14:37-49.), MP0112 (Campochiaro P A et al. Am J. Ophthalmol. 2013 April; 155(4):697-704), pegaptanib (Gragoudas E S et al, N Engl J. Med. 2004 Dec. 30; 351(27):2805-16.), CT-322 (Dineen S P et al, BMC Cancer. 2008 Nov. 27; 8:352. doi: 10.1186/1471-2407-8-352.), the anti-VEGF antibodies and fragments described in U.S. Patent Application Publication 20140186350 (which is incorporated by reference in its entirety), including NVS4, NVS80, NVS81, NVS82, NVS83, NVS84 and NVS85, and anti-VEGF antibodies and fragments as described in US20120014958 which are specifically incorporated by reference in their entirety. Also included within the term VEGF antagonists are derivatives of any of the above molecules.

EPO Antagonists

The various disclosed pharmaceutical compositions, regimens, processes, uses, methods and kits utilize an EPO antagonist, e.g., EPO binding molecule (e.g., EPO antibody or antigen-binding portion thereof, or EPO receptor binding molecule (e.g., EPO receptor antibody or antigen-binding portion thereof). Examples of EPO antagonists include antibodies or derivatives thereof having the CDR sequences, heavy, light chains, or combination of heavy and light chains of Fabs NVS1, NVS2, NVS3, or NVS4 (including antibodies or derivatives thereof comprising the Fabs NVS1-4) as disclosed in the Table below and in U.S. Patent Application Publication No. 2014/0199306, which is incorporated by reference in its entirety.

EPO Antagonist Sequence Table

| Amino acid sequence or polynucleotide (PN) | Sequence Identifier (SEQ. I. D. NO:) and sequence |
|---|---|
| NVS1 | |
| CDRH1 Kabat | 1 SYAIS |
| CDRH2 Kabat | 2 GIDPISGFADYAQKFQG |
| CDRH3 Kabat | 3 ELYYPGTWMAVMAY |
| CDRL1 Kabat | 4 SGDNIPEYYVH |
| CDRL2 Kabat | 5 RDNERPS |
| CDRL3 Kabat | 6 QVFDESSWHWV |
| CDRH1 Chothia | 7 GGTFRSY |
| CDRH2 Chothia | 8 DPISGF |
| CDRH3 Chothia | 9 ELYYPGTWMAVMAY |
| CDRL1 Chothia | 10 DNIPEYY |
| CDRL2 Chothia | 11 RDN |
| CDRL3 Chothia | 12 FDESSWHW |
| VH | 13 QVQLVQSGAEVKKPGSSVKVSCKASGGIFRSYAISWVRQAPGQGLEWMGGID PISGFADYAQKFQGRVTITADESTSTAYMELSSLRSEDTAVYYCARELYYPG TWMAVMAYWGRGTLVTVSS |
| VL | 14 SYVLTQPPSVSVAPGKTARITCSGDNIPEYYVHWYQQKPGQAPVLVIYRDNE RPSGIPERFSGSNSGNTATLTISRVEAGDEADYYCQVFDESSWHWVFGGGTK LTVL |
| Heavy chain | 15 QVQLVQSGAEVKKPGSSVKVSCKASGGTFRSYAISWVRQAPGQGLEWMGGID PISGFADYAQKFQGRVTITADESTSTAYMELSSLRSEDTAVYYCARELYYPG TWMAVMAYWGRGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKRVEPKSC |
| Light chain | 16 SYVLTQPPSVSVAPGKTARITCSGDNIPEYYVHWYQQKPGQAPVLVIYRDNE RPSGIPERFSGSNSGNTATLTISRVEAGDEADYYCQVFDESSWHWVFGGGTK LTVLGQPKAAPSVTLFPPSSEELQANKATLVCLISDFYPGAVTVAWKADSSP VKAGVETTTPSKQSNNKYAASSYLSLTPEQWKSHRSYSCQVTHEGSTVEKTV APTECS |
| PN encoding SEQ. I. D. NO: 13 | 17 caggtgcagctggtgcagtcaggcgccgaagtgaagaaacccggctctagcg tgaaggtgtcctgtaaagctagtggcggcacctttagatcctacgctattag ctgggtgcgacaggctccaggccagggcctcgaatggatgggcggcatcgac cctattagcggcttcgccgactacgctcagaaatttcagggcagagtgacta tcaccgccgacgagtctactagcaccgcctacatggaactgtctagcctgag atcagaggacaccgccgtgtactactgcgctagagagctgtactaccccggc acctggatggccgtgatggcctattggggcagaggcaccctggtgacagtgt cttct |
| PN encoding SEQ. I. D. NO: 14 | 18 agctacgtgctgacccagccccctagcgtgtcagtggcccctggcaagaccg ctagaatcacctgtagcggcgataacatccccgagtactacgtgcactggta tcagcagaagcccggccaggccccccgtgctggtgatctatagagataacgag cggcctagcggcatccccgagcggttttccggctctaatagcggcaacaccg ctaccctgactatttcaagagtggaagccggcgacgaggccgactactactg tcaggtgttcgacgagtcttcatggcactgggtgttcggcggaggcaccaag ctgaccgtgctg |
| PN encoding SEQ. I. D. NO: 15 | 19 caggtgcagctggtgcagtcaggcgccgaagtgaagaaacccggctctagcg tgaaggtgtcctgtaaagctagtggcggcacctttagatcctacgctattag ctgggtgcgacaggctccaggccagggcctcgaatggatgggcggcatcgac cctattagcggcttcgccgactacgctcagaaatttcagggcagagtgacta tcaccgccgacgagtctactagcaccgcctacatggaactgtctagcctgag atcagaggacaccgccgtgtactactgcgctagagagctgtactaccccggc acctggatggccgtgatggcctattggggcagaggcaccctggtgacagtgt cttctgctagcactaagggccccctccgtgttccctctggcccttccagcaa gtctacctctggcggcaccgctgctctgggctgcctggtgaaggactacttc cctgagcctgtgacagtgtcctggaactctggcgccctgacctccggcgtgc acaccttcctgccgtgctgcagtcctccggcctgtactccctgtcctccgt ggtgacagtgccttcctccagcctgggcacccagacctatatctgcaacgtg aaccacaagccttccaacaccaaggtggacaagcgggtggagcctaagtcat gc |
| PN encoding SEQ. I. D. NO: 16 | 20 agctacgtgctgacccagccccctagcgtgtcagtggcccctggcaagaccg ctagaatcacctgtagcggcgataacatccccgagtactacgtgcactggta tcagcagaagcccggccaggccccccgtgctggtgatctatagagataacgag cggcctagcggcatccccgagcggttttccggctctaatagcggcaacaccg ctaccctgactatttcaagagtggaagccggcgacgaggccgactactactg tcaggtgttcgacgagtcttcatggcactgggtgttcggcggaggcaccaag ctgaccgtgctgggccagcctaaggctgcccccagcgtgaccctgttccccc ccagcagcgaggagctgcaggccaacaaggccaccctggtgtgcctgatcag cgacttctacccaggcgccgtgaccgtggcctggaaggccgacagcagcccc gtgaaggccggcgtggagaccaccacccccagcaagcagagcaacaacaagt |

EPO Antagonist Sequence Table

| Amino acid sequence or polynucleotide (PN) | Sequence Identifier (SEQ. I. D. NO:) and sequence |
|---|---|
| | acgccgccagcagctacctgagcctgacccccgagcagtggaagagccacag<br>gtcctacagctgccaggtgacccacgagggcagcaccgtggaaaagaccgtg<br>gcccccaaccgagtgcagc |

NVS2

| | | |
|---|---|---|
| CDRH1_Kabat | 21 | SYWIG |
| CDRH2_Kabat | 22 | WIDPYRSEIRYSPSFQG |
| CDRH3_Kabat | 23 | VSSEPFDS |
| CDRL1_Kabat | 24 | SGDKLGDHYAY |
| CDRL2_Kabat | 25 | DDSKRPS |
| CDRL3_Kabat | 26 | ATWTFEGDYV |
| CDRH1 Chothia | 27 | GYSFTSY |
| CDRH2 Chothia | 28 | DPYRSE |
| CDRH3 Chothia | 29 | VSSEPFDS |
| CDRL1 Chothia | 30 | DKLGDHY |
| CDRL2 Chothia | 31 | DDS |
| CDRL3 Chothia | 32 | WTFEGDY |
| VH | 33 | EVQLVQSGAEVKKPGESLKISCKGSGYSFTSYWIGWVRQMPGKGLEWMGWID<br>PYRSEIRYSPSFQGQVTISADKSISTAYLQWSSLKASDTAMYYCARVSSEPF<br>DSWGQGTLVTVSS |
| VL | 34 | SYVLTQPPSVSVAPGKTARITCSGDKLGDHYAYWYQQKPGQAPVLVIYDDSK<br>RPSGIPERFSGSNSGNTATLTISRVEAGDEADYYCATWTFEGDYVFGGGTKL<br>TVL |
| Heavy chain | 35 | EVQLVQSGAEVKKPGESLKISCKGSGYSFTSYWIGWVRQMPGKGLEWMGWID<br>PYRSEIRYSPSFQGQVTISADKSISTAYLQWSSLKASDTAMYYCARVSSEPF<br>DSWGQGTLVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSN<br>TKVDKRVEPKSC |
| Light chain | 36 | SYVLTQPPSVSVAPGKTARITCSGDKLGDHYAYWYQQKPGQAPVLVIYDDSK<br>RPSGIPERFSGSNSGNTATLTISRVEAGDEADYYCATWTFEGDYVFGGGTKL<br>TVLGQPKAAPSVTLFPPSSEELQANKATLVCLISDFYPGAVTVAWKADSSPV<br>KAGVETTTPSKQSNNKYAASSYLSLTPEQWKSHRSYSCQVTHEGSTVEKTVA<br>PTECS |
| PN encoding SEQ. I. D. NO: 33 | 37 | Gaggtgcagctggtgcagtcaggcgccgaagtgaagaagcccggcgagtcac<br>tgaagattagctgtaaaggctcaggctatagcttcactagctactggatcgg<br>ctgggtgcgacagatgcccggcaagggcctggaatggatgggctggatcgac<br>ccctatagatcagagattaggtatagccctagctttcagggccaggtgacaa<br>ttagcgccgataagtctattagcaccgcctacctgcagtggtctagcctgaa<br>ggctagtgacaccgctatgtactactgcgctagagtgtctagcgagcccttc<br>gatagctggggccagggcaccctggtgacagtgtcttca |
| PN encoding SEQ. I. D. NO: 34 | 38 | agctacgtgctgacccagccccctagcgtgtcagtggcccctggcaagaccg<br>ctagaatcacctgtagcggcgataagctgggcgatcactacgcctactggta<br>tcagcagaagcccggccaggcccccgtgctggtgatctacgacgactctaag<br>cggcctagcggcatccccgagcggtttagcggctctaatagcggcaacaccg<br>ctaccctgactatttcaagagtggaagccggcgacgaggccgactactactg<br>cgctacctggaccttcgagggcgactacgtgttcggcggaggcactaagctg<br>accgtgctg |
| PN encoding SEQ. I. D. NO: 35 | 39 | gaggtgcagctggtgcagtcaggcgccgaagtgaagaagcccggcgagtcac<br>tgaagattagctgtaaaggctcaggctatagcttcactagctactggatcgg<br>ctgggtgcgacagatgcccggcaagggcctggaatggatgggctggatcgac<br>ccctatagatcagagattaggtatagccctagctttcagggccaggtgacaa<br>ttagcgccgataagtctattagcaccgcctacctgcagtggtctagcctgaa<br>ggctagtgacaccgctatgtactactgcgctagagtgtctagcgagcccttc<br>gatagctggggccagggcaccctggtgacagtgtcttcagctagcactaagg<br>gcccctccgtgttccctctggccccttccagcaagtctacctctggcggcac<br>cgctgctctgggctgcctggtgaaggactacttccctgagcctgtgacagtg<br>tcctggaactctggcgccctgacctccggcgtgcacaccttccctgccgtgc<br>tgcagtcctccggcctgtactccctgtcctccgtggtgacagtgccttcctc<br>cagcctgggcacccagacctatatctgcaacgtgaaccacaagccttccaac<br>accaaggtggacaagcgggtggagcctaagtcatgc |
| PN encoding SEQ. I. D. NO: 36 | 40 | agctacgtgctgacccagccccctagcgtgtcagtggcccctggcaagaccg<br>ctagaatcacctgtagcggcgataagctgggcgatcactacgcctactggta<br>tcagcagaagcccggccaggcccccgtgctggtgatctacgacgactctaag<br>cggcctagcggcatccccgagcggtttagcggctctaatagcggcaacaccg<br>ctaccctgactatttcaagagtggaagccggcgacgaggccgactactactg<br>cgctacctggaccttcgagggcgactacgtgttcggcggaggcactaagctg<br>accgtgctgggccagcctaaggctgcccccagcgtgaccctgttccccccca<br>gcagcgaggagctgcaggccaacaaggccaccctggtgtgcctgatcagcga<br>cttctacccaggcgccgtgaccgtggcctggaaggccgacagcagcccgtg<br>aaggccggcgtggagaccaccacccccagcaagcagagcaacaacaagtacg<br>ccgccagcagctacctgagcctgacccccgagcagtggaagagccacaggtc |

-continued

| EPO Antagonist Sequence Table | |
|---|---|
| Amino acid sequence or polynucleotide (PN) | Sequence Identifier (SEQ. I. D. NO:) and sequence |
| | ctacagctgccaggtgacccacgagggcagcaccgtggaaaagaccgtggcc<br>ccaaccgagtgcagc |

NVS3

| | | |
|---|---|---|
| CDRH1_Kabat | 41 | SNTAAWN |
| CDRH2_Kabat | 42 | VIYYRSKWYNDYAVSVKS |
| CDRH3_Kabat | 43 | SVPGGDPGLEHAFAY |
| CDRL1_Kabat | 44 | SGDNLGTYYVE |
| CDRL2_Kabat | 45 | DDSDRPS |
| CDRL3_Kabat | 46 | ASFASWSDSV |
| CDRH1_Chothia | 47 | GDSVSSNTA |
| CDRH2_Chothia | 48 | YYRSKWY |
| CDRH3_Chothia | 49 | SVPGGDPGLEHAFAY |
| CDRL1_Chothia | 50 | DNLGTYY |
| CDRL2_Chothia | 51 | DDS |
| CDRL3_Chothia | 52 | FASWSDS |
| VH | 53 | QVQLQQSGPGLVKPSQTLSLTCAISGDSVSSNTAAWNWIRQSPSRGLEWLGV<br>IYYRSKWYNDYAVSVKSRITINPDTSKNQFSLQLNSVTPEDTAVYYCARSVP<br>GGDPGLEHAFAYWGRGTLVTVSS |
| VL | 54 | SYVLTQPPSVSVAPGKTARITCSGDNLGTYYVEWYQQKPGQAPVLVIYDDSD<br>RPSGIPERFSGSNSGNTATLTISRVEAGDEADYYCASFASWSDSVFGGGTKL<br>TVL |
| Heavy chain | 55 | QVQLQQSGPGLVKPSQTLSLTCAISGDSVSSNTAAWNWIRQSPSRGLEWLGV<br>IYYRSKWYNDYAVSVKSRITINPDTSKNQFSLQLNSVTPEDTAVYYCARSVP<br>GGDPGLEHAFAYWGRGTLVTVSSASTKGPSVFPLAPSSKSTSGGTAALGCLV<br>KDYFPEPVTVSWNSGALTSGVHTFPAVLQSSGLYSLSSVVTVPSSSLGTQTY<br>ICNVNHKPSNTKVDKRVEPKSC |
| Light chain | 56 | SYVLTQPPSVSVAPGKTARITCSGDNLGTYYVEWYQQKPGQAPVLVIYDDSD<br>RPSGIPERFSGSNSGNTATLTISRVEAGDEADYYCASFASWSDSVFGGGTKL<br>TVLGQPKAAPSVTLFPPSSEELQANKATLVCLISDFYPGAVTVAWKADSSPV<br>KAGVETTTPSKQSNNKYAASSYLSLTPEQWKSHRSYSCQVTHEGSTVEKTVA<br>PTECS |
| PN encoding<br>SEQ. I. D. NO: 53 | 57 | Caggtgcagctgcagcagtcaggccctggcctggtgaaacctagtcagaccc<br>tgagcctgacctgcgctattagcggcgatagcgtgtcatctaacaccgccgc<br>ctggaactggattagacagtcacctagtagaggcctggaatggctgggcgtg<br>atctactataggtctaagtggtacaacgactacgccgtgtcagtgaagtcta<br>ggatcactattaaccccgacacctctaagaatcagttcagcctgcagctgaa<br>tagcgtgaccccgaggacaccgccgtgtactactgcgctagatcagtgcct<br>ggcggcgaccccggcctggaacacgcctttgcctactggggcagaggcaccc<br>tggtgacagtgtcttct |
| PN encoding<br>SEQ. I. D. NO: 54 | 58 | agctacgtgctgacccagccccctagcgtgtcagtggcccctggcaagaccg<br>ctagaatcacctgtagcggcgataacctgggcacctactacgtggaatggta<br>tcagcagaagcccggccaggcccccgtgctggtgatctacgacgatagcgat<br>agacctagcggcatccccgagcggtttagcggctctaatagcggcaacaccg<br>ctaccctgactattagtagagtggaagccggcgacgaggccgactactactg<br>cgctagtttcgctagttggagcgattcagtgttcggcggaggcactaagctg<br>accgtgctg |
| PN encoding<br>SEQ. I. D. NO: 55 | 59 | caggtgcagctgcagcagtcaggccctggcctggtgaaacctagtcagaccc<br>tgagcctgacctgcgctattagcggcgatagcgtgtcatctaacaccgccgc<br>ctggaactggattagacagtcacctagtagaggcctggaatggctgggcgtg<br>atctactataggtctaagtggtacaacgactacgccgtgtcagtgaagtcta<br>ggatcactattaaccccgacacctctaagaatcagttcagcctgcagctgaa<br>tagcgtgaccccgaggacaccgccgtgtactactgcgctagatcagtgcct<br>ggcggcgaccccggcctggaacacgcctttgcctactggggcagaggcaccc<br>tggtgacagtgtcttctgctagcactaagggccctccgtgttccctctggc<br>ccttccagcaagtctacctctggcggcaccgctgtctctggggctcctggtg<br>aaggactacttccctgagcctgtgacagtgtcctggaactctggcgccctga<br>cctccggcgtgcacaccttccctgccgtgctgcagtcctccgggcctgtactc<br>cctgtcctccgtggtgacagtgccttcctccagcctgggcacccagacctat<br>atctgcaacgtgaaccacaagccttccaacaccaaggtggacaagcgggtgg<br>agcctaagtcatgc |
| PN encoding<br>SEQ. I. D. NO: 56 | 60 | agctacgtgctgacccagccccctagcgtgtcagtggcccctggcaagaccg<br>ctagaatcacctgtagcggcgataacctgggcacctactacgtggaatggta<br>tcagcagaagcccggccaggcccccgtgctggtgatctacgacgatagcgat<br>agacctagcggcatccccgagcggtttagcggctctaatagcggcaacaccg<br>ctaccctgactattagtagagtggaagccggcgacgaggccgactactactg<br>cgctagtttcgctagttggagcgattcagtgttcggcggaggcactaagctg<br>accgtgctgggccagcctaaggctgcccccagcgtgaccctgttccccccca<br>gcagcgaggagctgcaggccaacaaggccaccctggtgtgcctgatcagcga<br>cttctacccaggcgccgtgaccgtggcctggaaggccgacagcagccccgtg<br>aaggcggcgtggagaccaccacccccagcaagcagagcaacaacaagtacg |

EPO Antagonist Sequence Table

| Amino acid sequence or polynucleotide (PN) | Sequence Identifier (SEQ. I. D. NO:) and sequence |
|---|---|
| | ccgccagcagctacctgagcctgacccccgagcagtggaagagccacaggtc<br>ctacagctgccaggtgacccacgagggcagcaccgtggaaaagaccgtggcc<br>ccaaccgagtgcagc |

NVS4

| | | |
|---|---|---|
| CDRH1_Kabat | 61 | SYYMS |
| CDRH2_Kabat | 62 | WINPLKGNTNYAQKFQG |
| CDRH3_Kabat | 63 | EGMYFDI |
| CDRL1_Kabat | 64 | SGDSIGDKYVY |
| CDRL2_Kabat | 65 | DTNKRPS |
| CDRL3_Kabat | 66 | QSWDLDFNTYV |
| CDRH1 Chothia | 67 | GYTFTSY |
| CDRH2 Chothia | 68 | NPLKGN |
| CDRH3 Chothia | 69 | EGMYFDI |
| CDRL1 Chothia | 70 | DSIGDKY |
| CDRL2 Chothia | 71 | DTN |
| CDRL3 Chothia | 72 | WDLDFNTY |
| VH | 73 | QVQLVQSGAEVKKPGASVKVSCKASGYTFTSYYMSWVRQAPGQGLEWMGWIN<br>PLKGNTNYAQKFQGRVTMTRDTSISTAYMELSRLRSEDTAVYYCAREGMYFD<br>IWGQGTLVTVSS |
| VL | 74 | SYELTQPLSVSVALGQTARITCSGDSIGDKYVYWYQQKPGQAPVLVIYDTNK<br>RPSGIPERFSGSNSGNTATLTISRAQAGDEADYYCQSWDLDFNTYVFGGGTK<br>LTVL |
| Heavy chain | 75 | gvglvgsgaevkkpgasvkvsckasgytftsyymswvrqapgqglewmgwin<br>plkgntnyaqkfqgrvtmtrdtsistaymelsrlrsedtavyycaregmyfd<br>iwgqgtlvtvssastkgpsvflplapsskstsggtaalgclvkdyfpepvtvs<br>wnsgaltsgvhtfpavlgssglyslssvvtvpssslgtqtyicnvnhkpsnt<br>kvdkrvepksc |
| Light chain | 76 | SYELTQPLSVSVALGQTARITCSGDSIGDKYVYWYQQKPGQAPVLVIYDTNK<br>RPSGIPERFSGSNSGNTATLTISRAQAGDEADYYCQSWDLDFNTYVFGGGTK<br>LTVLGQPKAAPSVTLFPPSSEELQANKATLVCLISDFYPGAVTVAWKADSSP<br>VKAGVETTTPSKQSNNKYAASSYLSLTPEQWKSHRSYSCQVTHEGSTVEKTV<br>APTECS |
| PN encoding<br>SEQ. I. D. NO: 73 | 77 | caggtgcagctggtgcagtcaggcgccgaagtgaagaaacccggcgctagtg<br>tgaaggtgtcctgtaaagctagtggctacaccttcactagctactacatgag<br>ctgggtgcgacaggcccctggacagggcctggaatggatgggctggattaac<br>cccctgaagggcaacactaactacgcccagaaattccagggccgagtgacta<br>tgactagggacactagcattagcaccgcctacatggaactgtctaggctgag<br>atcagaggacaccgccgtgtactactgcgctagagaaggcatgtacttcgac<br>atctggggccagggcaccctggtgacagtgtcttct |
| PN encoding<br>SEQ. I. D. NO: 74 | 78 | agctacgagctgactcagcccctgagcgtgtcagtggccctgggacagaccg<br>ctagaatcacctgtagcggcgactctatcggcgacaaatacgtgtactggta<br>tcagcagaagcccggccaggcccccgtgctggtgatctacgacactaacaag<br>cggcctagcggcatccccgagcggtttagcggctctaatagcggcaacaccg<br>ctaccctgactattagtagggctcaggccggcgacgaggccgactactactg<br>tcagtcatgggacctggacttcaacacctacgtgttcggcggaggcactaag<br>ctgaccgtgctg |
| PN encoding<br>SEQ. I. D. NO: 75 | 79 | caggtgcagctggtgcagtcaggcgccgaagtgaagaaacccggcgctagtg<br>tgaaggtgtcctgtaaagctagtggctacaccttcactagctactacatgag<br>ctgggtgcgacaggcccctggacagggcctggaatggatgggctggattaac<br>cccctgaagggcaacactaactacgcccagaaattccagggccgagtgacta<br>tgactagggacactagcattagcaccgcctacatggaactgtctaggctgag<br>atcagaggacaccgccgtgtactactgcgctagagaaggcatgtacttcgac<br>atctggggccagggcaccctggtgacagtgtcttctgctagcactaagggcc<br>cctccgtgttccctctggcccccttccagcaagtctacctctggcggcaccgc<br>tgctctgggctgcctggtgaaggactacttccctgagcctgtgacagtgtcc<br>tggaactctggcgccctgacctccggcgtgcacaccttccctgccgtgctgc<br>agtcctccggcctgtactccctgtcctccgtggtgacagtgccttcctccag<br>cctgggcacccagacctatatctgcaacgtgaaccacaagccttccaacacc<br>aaggtggacaagcgggtggagcctaagtcatgc |
| PN encoding<br>SEQ. I. D. NO: 76 | 80 | agctacgagctgactcagcccctgagcgtgtcagtggccctgggacagaccg<br>ctagaatcacctgtagcggcgactctatcggcgacaaatacgtgtactggta<br>tcagcagaagcccggccaggcccccgtgctggtgatctacgacactaacaag<br>cggcctagcggcatccccgagcggtttagcggctctaatagcggcaacaccg<br>ctaccctgactattagtagggctcaggccggcgacgaggccgactactactg<br>tcagtcatgggacctggacttcaacacctacgtgttcggcggaggcactaag<br>ctgaccgtgctgggccagcctaaggctgccccagcgtgaccctgttccccc<br>ccagcagcgaggagctgcaggccaacaaggccaccctggtgtgcctgatcag<br>cgacttctacccaggcgccgtgaccgtggcctggaaggccgacagcagcccc<br>gtgaaggccggcgtggagaccaccacccccagcaagcagagcaacaacaagt<br>acgccgccagcagctacctgagcctgacccccgagcagtggaagagccacag |

-continued

EPO Antagonist Sequence Table

| Amino acid sequence or polynucleotide (PN) | Sequence Identifier (SEQ. I. D. NO:) and sequence |
|---|---|
| | gtcctacagctgccaggtgacccacgagggcagcaccgtggaaaagaccgtg gccccaaccgagtgcagc |
| Human Epo NP_000790.2 | 81 apprlicdsrvlerylleakeaenittgcaehcslnenitvpdtkvnfyawk rmevgqqavevwqglallseavlrgqallvnssqpweplqlhvdkavsglrs lttllralgagkeaisppdaasaaplrtitadtfrklfrvysnflrgklkly tgeacrtgdr |
| Cynomolgus Epo Uniprot: P07865 | 82 apprlicdsrvlerylleakeaenvtmgcsescslnenitvpdtkvnfyawk rmevgggavevwqglallseavlrggavlanssgpfeplglhmdkaisglrs ittllralgageaislpdaasaaplrtitadtfcklfrvysnflrgklklyt geacrrgdr |
| Mouse Epo NP_031968.1 | 83 apprlicdsrvleryileakeaenvtmgcaegprlsenitvpdtkvnfyawk rmevgqqavevwqglallseavlrgqallvnssqpweplqlhvdkavsglrs ltsllrvlgagkelmsppdttppaplrtltvdtfcklfrvyanflrgklkly tgevcrrgdr |
| Rat Epo NP_058697.1 | 84 apprlicdsrvleryileakeaenvtmgcaegprlsenitvpdtkvnfyawk rmevgqqavevwqglallseavlrgqallvnssqpweplqlhvdkavsglrs ltsllrvlgagkelmsppdatgaaplrtltadtfcklfrvysnflrgklkly tgeacrrgdr |
| Rabbit Epo NP_001075559.1 | 85 Klatmgvrgrlallplallollvlalglpvlgaparlicdsrvleryileak eaenvtmgcaegcslgenitvpdtkvnfhhwkkseagrhavevwqglallse amlrsgallanssglpetlgvhvdkaysglrsltsllralgvgkeaysppea assaaplrtvaadticklfriysnflrgklklytgeacrrgdr |
| Epo Helix A, amino acids 4-26 of SEQ ID NO: 81 | 86 rlicdsrvlerylleakeaenit |
| Epo Helix B, amino acids 56-83 of SEQ ID NO: 81 | 87 vgggavevwgglallseavlrggallvn |
| Epo Helix D, amino acids 138-162 of SEQ ID NO: 81 | 88 frklfrvysnflrgklklytgeacr |
| Epo Loop A-B, amino acids 27-55 of SEQ ID NO: 81 | 89 tgcaehcslnenitvpdtkvnfawkrme |

Ophthalmic Diseases

The disclosed methods are useful for the diagnosis, treatment, prevention, and/or amelioration of ophthalmic diseases, including conditions or disorders associated with retinal vascular disease, i.e., conditions, disorders or diseases in which the retina degenerates or becomes dysfunctional. This includes conditions or disorders associated with diabetic retinopathy (DR), conditions or disorders associated with diabetic macular edema (DME), proliferative diabetic retinopathy (PDR), non-proliferative diabetic retinopathy (NPDR), age-related macular degeneration (AMD), retinal vein occlusion (RVO), multifocal choroiditis, myopic choroidal neovascularization, or retinopathy of prematurity. Anatomic characteristics of retinal vascular disease that may be treated by EPO and/or VEGF inhibition include macular edema, venous dilation, vessel tortuosity, vascular leakage as measured by fluorescein angiography, retinal hemorrhage, and microvascular anomalies (e.g. microaneurysm, cotton-wool spots, IRMA), capillary dropout, leukocyte adhesion, retinal ischemia, neovascularization of the optic disk, neovascularization of the posterior pole, iris neovascularization, intraretinal hemorrhage, vitreous hemorrhage, macular scar, subretinal fibrosis, and retinal fibrosis.

The term "condition or disorder associated with diabetic retinopathy" refers to conditions in which the retina degenerates or becomes dysfunctional, as a consequence of effects of diabetes mellitus (Type 1 or Type 2) on retinal vasculature, retinal metabolism, retinal pigment epithelium, the blood-retinal barrier, or ocular levels of advanced glycation end products (AGEs), aldose reductase activity, glycosylated hemoglobin, and protein kinase C. Visual loss in patients with diabetic retinopathy can be a result of retinal ischemia, macular edema, vascular leakage, vitreous hemorrhage, or direct effects of elevated glucose levels on retinal neurons. Anatomic characteristics of diabetic retinopathy that may be treated by Epo inhibition include microaneurysm, cotton wool spots, venous dilation, macular edema, intra-retinal microvascular abnormalities (IRMA), intra-retinal hemorrhage, vascular proliferation, neovascularization of the disk, rubeosis, and retinal ischemia. "Diabetic macular edema" occurs in a subject with diabetic retinopathy and can occur at any stage of the disease.

The term "condition or disorder associated with macular edema", refers to conditions or disorders in which swelling or thickening of the macula occurs as a result of retinal blood vessels leaking fluid, "macular edema". Macular edema occurs in, and is often a complication of, retinal vascular disease. Specific conditions or disorders associated with macular edema include, diabetic retinopathy, diabetic macular edema, proliferative diabetic retinopathy, non-proliferative diabetic retinopathy, age-related macular degeneration, retinal vein occlusion, multifocal choroiditis, myopic choroidal neovascularization, or retinopathy of prematurity. Treatment of macular edema by the inhibition of Epo can be determined by funduscopic examination, optical coherence tomography, and improved visual acuity.

Techniques for Assaying, Diagnostic Methods and Methods of Producing a Transmittable Form of Information The disclosed methods are useful for the treatment, prevention, or amelioration of ophthalmic diseases, as well as predicting the likelihood of an ophthalmic disease patient's response to treatment with a VEGF and/or EPO antagonist. These methods employ, inter alia, determining whether a patient has an ophthalmic response marker in a sample from the patient.

A biological sample from the patient may be assayed for the presence of an ophthalmic response marker by any applicable conventional means. Numerous biological samples may be used to identify the presence of alleles or proteins, the level of expression of genes or proteins, and the activity of a protein, e.g., blood, synovial fluid, buffy coat, serum, plasma, lymph, feces, urine, tear, saliva, cerebrospinal fluid, buccal swabs, sputum, or tissue. Various sources within a biological sample may be used in the disclosed methods, e.g., one may assay genomic DNA obtained from a biological sample to detect an ophthalmic response marker, or one may assay products of a an ophthalmic response marker, e.g., nucleic acid products (e.g., DNA, pre-mRNA, mRNA, micro RNAs, etc.) and polypeptide products (e.g., expressed proteins) obtained from a biological sample.

As described in the Examples, we have discovered that the presence of a thymine at the locus rs1617640 (e.g., a thymine in both alleles at the locus rs1617640) results in decreased sensitivity to ranibizumab when compared to other alleles. Based in part on this discovery, the invention features the selective treatment of subjects not having (one or more) thymines at the locus rs1617640.

Also, as described in the Examples, we have discovered that the presence of a cytosine at the locus rs2010963 (e.g., a cytosine in both alleles at the locus rs2010963) results in decreased sensitivity to ranibizumab when compared to other alleles. Based in part on this discovery, the invention features the selective treatment of subjects not having (one or more) cytosines at the locus rs2010963.

DNA (genomic and cDNA) for SNP detection can be prepared from a biological sample by methods well known in the art, e.g., phenol/chloroform extraction, PUREGENE DNA® purification system from GentAS Systems (Qiagen, CA). Detection of a DNA sequence may include examining the nucleotide(s) located at either the sense or the anti-sense strand within that region. The presence of polymorphisms in a patient may be detected from DNA (genomic or cDNA) obtained from PCR using sequence-specific probes, e.g., hydrolysis probes from Taqman, Beacons, Scorpions; or hybridization probes that detect the marker or polymorphism. For the detection of the polymorphism, sequence specific probes may be designed such that they specifically hybridize to the genomic DNA for the alleles of interest or, in some cases, an RNA of interest. Primers and probes for polymorphic sites (e.g., SNP) may be designed based on context sequences found in the NCBI SNP database available at: www.ncbi.nlm.nih.gov/snp. These probes may be labeled for direct detection or contacted by a second, detectable molecule that specifically binds to the probe. The PCR products also can be detected by DNA-binding agents. Said PCR products can then be subsequently sequenced by any DNA sequencing method available in the art. Alternatively the presence of allele can be detected by sequencing using any sequencing methods such as, but not limited to, Sanger-based sequencing, pyrosequencing or next generation sequencing (Shendure J. and Ji, H., Nature Biotechnology (1998), Vol. 26, Nr 10, pages 1135-1145). Optimised allelic discrimination assays for SNPs may be purchased from Applied Biosystems (Foster City, Calif., USA).

Various techniques can be applied to interrogate a particular polymorphism (e.g., SNP), including, e.g., hybridization-based methods, such as dynamic allele-specific hybridization (DASH) genotyping, polymorphic site (e.g., SNP) detection through molecular beacons (Abravaya K., et al. (2003) Clin Chem Lab Med. 41:468-474), LUMINEX XMAP® technology (bead-based multiplexed immunoassay system in a microplate format), Illumina GOLDENGATE® (genotyping assay) technology and commercially available high-density oligonucleotide SNP arrays (e.g., the Affymetrix Human SNP 5.0 GENECHIP® (microarray platform) performs a genome-wide assay that can genotype over 500,000 human SNPs), BEADCHIP® (microarray technology) kits from Illumina, e.g, Human660W-Quad and Human 1.2M-Duo); enzyme-based methods, such as restriction fragment length polymorphism (RFLP), PCR-based methods (e.g., Tetra-primer ARMS-PCR), Invader assays (Olivier M. (2005) Mutat Res. 573(1-2):103-10), various primer extension assays (incorporated into detection formats, e.g., MALDI-TOF Mass spectrometry, electrophoresis, blotting, and ELISA-like methods), TAQMAN® (SNP genotyping assay from Applied Biosystems) assays, and oligonucleotide ligase assays; and other post-amplification methods, e.g., analysis of single strand conformation polymorphism (Costabile et al. (2006) Hum. Mutat. 27(12):1163-73), temperature gradient gel electrophoresis (TGGE), denaturing high performance liquid chromatography, high-resolution melting analysis, DNA mismatch-binding protein assays (e.g., MutS protein from *Thermus aquaticus* binds different single nucleotide mismatches with different affinities and can be used in capillary electrophoresis to differentiate all six sets of mismatches), SNPLEX® (proprietary SNP detecting system available from Applied Biosystems), capillary electrophoresis, mass spectrometry, and various sequencing methods, e.g., pyrosequencing and next generation sequencing, etc. Commercial kits for SNP genotyping include, e.g., Fluidigm DYNAMIC ARRAY® IFCs (Fluidigm), TAQMAN® SNP Genotyping Assay (Applied Biosystems), MASSARRAY® IPLEX GOLD (Sequenom), TYPE-IT FAST® SNP Probe PCR Kit (Quiagen), etc.

In some embodiments, the presence of a polymorphic site (e.g., SNP) in a patient is detected using a hybridization assay. In a hybridization assay, the presence of the genetic marker is determined based on the ability of the nucleic acid from the sample to hybridize to a complementary nucleic acid molecule, e.g., an oligonucleotide probe. A variety of hybridization assays are available. In some, hybridization of a probe to the sequence of interest is detected directly by visualizing a bound probe, e.g., a Northern or Southern assay. In these assays, DNA (Southern) or RNA (Northern) is isolated. The DNA or RNA is then cleaved with a series of restriction enzymes that cleave infrequently in the genome and not near any of the markers being assayed. The DNA or RNA is then separated, e.g., on an agarose gel, and transferred to a membrane. A labeled probe or probes, e.g., by incorporating a radionucleotide or binding agent (e.g., SYBR® Green), is allowed to contact the membrane under low-, medium- or high-stringency conditions. Unbound probe is removed and the presence of binding is detected by visualizing the labeled probe. In some embodiments, arrays, e.g., the MASSARRAY® system (SNP genotyping kit; Sequenom, San Diego, Calif., USA) may be used to genotype a subject.

Traditional genotyping methods may also be modified for use in genotyping. Such traditional methods include, e.g., DNA amplification techniques such as PCR and variants thereof, direct sequencing, SSO hybridization coupled with the LUMINEX XMAP® (bead-based multiplexed immunoassay system in a microplate format) technology, SSP typing, and SBT.

Sequence-Specific Oligonucleotide (SSO) typing uses PCR target amplification, hybridization of PCR products to a panel of immobilized sequence-specific oligonucleotides on the beads, detection of probe-bound amplified product by color formation followed by data analysis. Those skilled in the art would understand that the described Sequence-Specific Oligonucleotide (SSO) hybridization may be performed using various commercially available kits, such as those provided by One Lambda, Inc. (Canoga Park, Calif.) or Lifecodes HLA Typing Kits (Tepnel Life Sciences Corp.) coupled with LUMINEX® technology (Luminex, Corporation, TX). LABTYPE® SSO is a reverse SSO (rSSO) DNA typing solution that uses sequence-specific oligonucleotide (SSO) probes and color-coded microspheres to identify HLA alleles. The target DNA is amplified by polymerase chain reactions (PCR) and then hybridized with the bead probe array. The assay takes place in a single well of a 96-well PCR plate; thus, 96 samples can be processed at one time.

Sequence Specific Primers (SSP) typing is a PCR based technique which uses sequence specific primers for DNA based typing. The SSP method is based on the principle that only primers with completely matched sequences to the target sequences result in amplified products under controlled PCR conditions. Allele sequence-specific primer pairs are designed to selectively amplify target sequences which are specific to a single allele or group of alleles. PCR products can be visualized on agarose gel. Control primer pairs that matches non-allelic sequences present in all samples act as an internal PCR control to verify the efficiency of the PCR amplification. Those skilled in the art would understand that low, medium and high resolution genotyping with the described sequence-specific primer typing may be performed using various commercially available kits, such as the Olerup SSP™ kits (Olerup, PA) or (Invitrogen) or Allset and TMGOLD DQA1 Low resolution SSP (Invitrogen).

Sequence Based Typing (SBT) is based on PCR target amplification, followed by sequencing of the PCR products and data analysis.

In some cases, RNA, e.g., mature mRNA, pre-mRNA, can also be used to determine the presence of particular polymorphisms. For example, the quantity of EPO mRNA can be used as a surrogate for EPO promoter activity. Analysis of the sequence of mRNA transcribed from a given gene can be performed using any known method in the art including, but not limited to Northern blot analysis, nuclease protection assays (NPA), in situ hybridization, reverse transcription-polymerase chain reaction (RT-PCR), RT-PCR ELISA, TaqMan-based quantitative RT-PCR (probe-based quantitative RT-PCR) and SYBR green-based quantitative RT-PCR.

In some cases, the presence of a polymorphism in a patient can be determined by analyzing polypeptide products of the ophthalmic response markers as a surrogate for EPO promoter activity. Detection of polypeptide products can be performed using any known method in the art including, but not limited, to immunocytochemical staining, ELISA, flow cytometry, Western blot, spectrophotometry, HPLC, and mass spectrometry.

One method for detecting polypeptide products in a sample is by means of a probe that is a binding protein capable of interacting specifically with a marker protein (e.g., an antibody capable of binding EPO protein). Preferably, labeled antibodies, binding portions thereof, or other binding partners can be used. The antibodies can be monoclonal or polyclonal in origin, or may be biosynthetically produced. The binding partners may also be naturally occurring molecules or synthetically produced. The amount of complexed proteins is determined using standard protein detection methodologies described in the art. A detailed review of immunological assay design, theory and protocols can be found in numerous texts in the art, including Practical Immunology, Butt, W. R., ed., Marcel Dekker, New York, 1984. A variety of assays are available for detecting proteins with labeled antibodies. Direct labels include fluorescent or luminescent tags, metals, dyes, radionucleides, and the like, attached to the antibody. Indirect labels include various enzymes well known in the art, such as alkaline phosphatase, hydrogen peroxidase and the like. In a one-step assay, polypeptide products, if present, are immobilized and incubated with a labeled antibody. The labeled antibody binds to the immobilized target molecule. After washing to remove unbound molecules, the sample is assayed for the label.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and then processed quickly through washes and detection steps to generate a measurable signal, such as a colored spot.

In a two-step assay, immobilized EPO may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art. The antibodies may be labeled with a radioactive atom, an enzyme, a chromophoric or fluorescent moiety, or a colorimetric tag. The choice of tagging label also will depend on the detection limitations desired. Enzyme assays (ELISAs) typically allow detection of a colored product formed by interaction of the enzyme-tagged complex with an enzyme substrate. Some examples of radioactive atoms include $^{32}P$, $^{125}I$, $^{3}H$, and $^{14}P$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avidin or -streptavidin, and antibody-antigen.

In one aspect, the present disclosure contemplates the use of a sandwich technique for detecting polypeptide products in biological samples. The technique requires two antibodies capable of binding the protein of interest: e.g., one immobilized onto a solid support and one free in solution, but labeled with some easily detectable chemical compound. Examples of chemical labels that may be used for the second antibody include but are not limited to radioisotopes, fluorescent compounds, and enzymes or other molecules which generate colored or electrochemically active products when exposed to a reactant or enzyme substrate. When samples containing polypeptide products are placed in this system, the polypeptide products binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

Preferably, the presence of polypeptide products in a sample is detected by radioimmunoassays or enzyme-linked immunoassays, competitive binding enzyme-linked immunoassays, dot blot, Western blot, chromatography, preferably high performance liquid chromatography (HPLC), or other assays known in the art. Specific immunological binding of the antibody to the protein or polypeptide can be detected directly or indirectly.

In performing any of the methods described herein that require determining the presence of an ophthalmic response marker, such determination may be made by consulting a data repository that contains sufficient information on the patient's genetic composition to determine whether the patient has the marker of interest. Preferably, the data repository lists the genotype present (or absent) in the individual. The data repository could include the individual's patient records, a medical data card, a file (e. g., a flat ASCII file) accessible by a computer or other electronic or non-electronic media on which appropriate information or genetic data can be stored. As used herein, a medical data card is a portable storage device such as a magnetic data card, a smart card, which has an on-board processing unit and which is sold by vendors such as Siemens of Munich Germany, or a flash-memory card. If the data repository is a file accessible by a computer; such files may be located on various media, including: a server, a client, a hard disk, a CD, a DVD, a personal digital assistant such as a smart phone, a tape recorder, a zip disk, the computer's internal ROM (read-only-memory) or the internet or worldwide web. Other media for the storage of files accessible by a computer will be obvious to one skilled in the art.

Typically, once the presence of an ophthalmic response marker is determined, physicians or genetic counselors or patients or other researchers may be informed of the result. Specifically the result can be cast in a transmittable form of information that can be communicated or transmitted to other researchers or physicians or genetic counselors or patients. Such a form can vary and can be tangible or intangible. The result in the individual tested can be embodied in descriptive statements, diagrams, photographs, charts, images or any other visual forms. For example, images of gel electrophoresis of PCR products can be used in explaining the results. Diagrams showing where a variant occurs in an individual's allele are also useful in indicating the testing results. Statements regarding levels of EPO expression, levels of EPO protein/activity, or the presence of an ophthalmic response marker are also useful in indicating the testing results. These statements and visual forms can be recorded on a tangible media such as papers, computer readable media such as floppy disks, compact disks, etc., or on an intangible media, e.g., an electronic media in the form of email or website on internet or intranet. In addition, the result can also be recorded in a sound form and transmitted through any suitable media, e.g., analog or digital cable lines, fiber optic cables, etc., via telephone, facsimile, wireless mobile phone, internet phone and the like. All such forms (tangible and intangible) would constitute a "transmittable form of information". Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present disclosure also encompasses a method for producing a transmittable form of information containing levels of EPO expression, levels of EPO protein/activity, or the presence of an ophthalmic response marker or in an individual. This form of information is useful for predicting the responsiveness of a patient having an ophthalmic disorder to treatment with a VEGF and/or EPO antagonist, for selecting a course of treatment based upon that information, and for selectively treating a patient based upon that information.

Disclosed herein are methods of predicting the likelihood that a patient having an ophthalmic disease will respond to treatment with a VEGF and/or EPO antagonist, comprising detecting the presence or absence of at least one ophthalmic response marker in a biological sample from the patient. As noted above, the presence of one or more alleles containing an ophthalmic response marker is associated with an increased likelihood that anti-VEGF monotherapy will be efficacious. As noted above, a subject can have as few as zero and as many as four alleles containing an ophthalmic response marker (two each for the presence of a nucleic acid other than a thymine at locus rs1617640 and the presence of a guanine at locus rs2010963). Accordingly, the greater number of ophthalmic response markers, the greater the likelihood of efficacy of anti-VEGF monotherapy. Conversely, the fewer ophthalmic response makers present in a subject, the greater the likelihood that treatment with an EPO antagonist will be suggested. In particular, the presence of one or more thymines at locus rs1617640 is suggestive of therapy with EPO antagonists.

In some embodiments, the method further comprises the step of obtaining the biological sample from the patient, wherein the step of obtaining is performed prior to the step of assaying.

In some embodiments, the at least one ophthalmic response marker is detected by assaying the biological sample for a nucleic acid product of the at least one ophthalmic response marker, a polypeptide product of the at least one ophthalmic response marker, or an equivalent genetic marker of the at least one ophthalmic response marker. In some embodiments, the ophthalmic response marker is detected by assaying the biological sample for a genomic sequence of the at least one ophthalmic response marker. In some embodiments, the biological sample is selected from the group consisting of synovial fluid, blood, serum, feces, plasma, urine, tear, saliva, cerebrospinal fluid, a leukocyte sample and a tissue sample.

Disclosed herein are also various methods of predicting the likelihood that a patient having an ophthalmic disease selected from retinal vascular disease, macular edema, diabetic retinopathy, diabetic macular edema, proliferative diabetic retinopathy, and VEGF-mediated disorders will respond to treatment with a VEGF antagonist and/or EPO antagonist, comprising detecting the level of EPO expression (e.g., mRNA, cDNA, etc.), the level of EPO protein, and/or the level of EPO activity in a biological sample from the patient relative to a control; wherein a decreased level of EPO expression, decreased level of EPO protein, and/or a decreased level of EPO activity relative to the control is indicative of an increased likelihood that the patient will respond to treatment with the VEGF antagonist (e.g., monotherapy with the VEGF antagonist). In such an embodiment, the control is a reference level of EPO expression, level of EPO protein, or level of EPO activity derived from a subject known to respond poorly to treatment with a VEGF antagonist.

Disclosed herein are also various methods of predicting the likelihood that a patient having an ophthalmic disease selected from retinal vascular disease, macular edema, diabetic retinopathy, diabetic macular edema, proliferative diabetic retinopathy, and VEGF-mediated disorders will respond to treatment with VEGF and/or EPO antagonist, comprising detecting an ophthalmic response marker, the level of EPO expression (e.g., mRNA, cDNA, etc.), the level of EPO protein, and/or the level of EPO activity in a biological sample from the patient relative to a control; wherein a similar level of EPO expression, similar level of EPO protein, or a similar level of EPO activity relative to the control is indicative of an increased likelihood that the patient will respond to treatment with the VEGF and/or EPO antagonist. In such an embodiment, the control is a reference level of EPO expression, level of EPO protein, or level of EPO activity derived from a subject known to respond well to treatment with VEGF and/or EPO antagonist.

In some embodiments, the presence of the at least one ophthalmic response marker, the level of EPO expression, or level of EPO protein/activity is detected by a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, SNPLEX® (SNP detecting system available from Applied Biosystems), capillary electrophoresis, Southern Blot, immunoassays, immunohistochemistry, ELISA, flow cytometry, Western blot, HPLC, and mass spectrometry.

In some embodiments, the ophthalmic disease is retinal vascular disease. In some embodiments, the ophthalmic disease is macular edema. In some embodiments, the ophthalmic disease is diabetic retinopathy. In some embodiments, the ophthalmic disease is diabetic macular edema. In some embodiments, the ophthalmic disease is proliferative diabetic retinopathy.

Methods of Treatment and Uses of VEGF and EPO Antagonists

The disclosed methods allow clinicians to provide a personalized therapy to patients having an ophthalmic disease (e.g., retinal vascular disease, macular edema, diabetic retinopathy, diabetic macular edema, proliferative diabetic retinopathy, and VEGF-mediated disorders) i.e., they allow determination of whether to selectively treat the patient with an either a VEGF antagonist, EPO antagonist, or combination of both a VEGF and EPO antagonist. In this way, a clinician can maximize the benefit and minimize the risk of VEGF and/or EPO antagonism in the entire population of patients afflicted with an ophthalmic disease (e.g., retinal vascular disease, macular edema, diabetic retinopathy, diabetic macular edema, proliferative diabetic retinopathy, and VEGF-mediated disorders). It will be understood that VEGF and EPO antagonists are useful for the treatment, prevention, or amelioration of ophthalmic disease (e.g., retinal vascular disease, macular edema, diabetic retinopathy, diabetic macular edema, proliferative diabetic retinopathy, and VEGF-mediated disorders) as disclosed herein.

The VEGF and/or EPO antagonists may be used as a pharmaceutical composition when combined with a pharmaceutically acceptable carrier. Such a composition may contain, in addition to a VEGF and/or EPO antagonist, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the VEGF and/or EPO antagonists, or to minimize side effects caused by the VEGF and/or EPO antagonists.

In practicing some of the methods of treatment or uses of the present disclosure, a therapeutically effective amount of a VEGF and/or EPO antagonist, is administered to a patient, (e.g., a human). While it is understood that the disclosed methods provide for selective treatment of patients depending on the presence of an ophthalmic response marker, this does not preclude that, if the patient is ultimately treated with a VEGF and/or EPO antagonist, such VEGF and/or EPO antagonist therapy is necessarily the sole therapy. Indeed, if a patient is selected for treatment with a VEGF and/or EPO antagonist, then the VEGF and/or EPO antagonist may be administered in accordance with the method of the disclosure either alone or in combination with other therapeutics for treating ophthalmic disease in patients. When coadministered with one or more additional therapeutics, a VEGF and/or EPO antagonist may be administered either simultaneously with the other therapeutic, or sequentially. If administered sequentially, the attending physician will decide on the appropriate sequence of administering the VEGF and/or EPO antagonist in combination with other therapeutics, as well as the appropriate dosages for co-delivery.

It is preferred that administration be intravitreal. Other methods of administration include, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Kits

The invention also encompasses kits for detecting an ophthalmic response marker in a patient. Such kits can be used to predict if a patient having an ophthalmic disease selected from retinal vascular disease, macular edema, diabetic retinopathy, diabetic macular edema, proliferative diabetic retinopathy, and VEGF-mediated disorders is likely to respond (or have a higher response) to treatment with a VEGF and/or EPO antagonist. For example, the kit can comprise a probe (e.g., an oligonucleotide, antibody, labeled compound or other agent) capable of detecting an ophthalmic response marker in a biological sample. The kit may also comprise instructions for providing a prediction of the likelihood that the patient will respond to treatment with the VEGF and/or EPO antagonist.

Probes may specifically hybridize to genomic sequences, nucleic acid products, or polypeptide products. Exemplary probes are oligonucleotides or conjugated oligonucleotides that specifically hybridizes to the response alleles of, e.g., rs1617640 (e.g., from DNA, cDNA, mRNA, etc.); primer-extension oligonucleotides, allele-specific primers, a combination of allele-specific primers, allele-specific probes, and primer extension primers, etc. Optionally, the kit can contain a probe that targets an internal control allele, which can be any allele presented in the general population. Detection of an internal control allele is designed to assure the performance of the kit. The disclosed kits can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for use.

Such kits may also comprise a VEGF and/or EPO antagonist or a pharmaceutical composition comprising the VEGF and/or EPO antagonist. In this way, such kits are useful in the selective treatment of patients having an ophthalmic disorder using a VEGF and/or EPO antagonist. Additionally, such kits may comprise means for administering the antagonist (e.g., a syringe and vial, a prefilled syringe, a prefilled pen) and instructions for use. These kits may contain additional therapeutic agents (described supra) for treating an ophthalmic disease, e.g., for delivery in combination with the enclosed VEGF and/or EPO antagonists.

The phrase "means for administering" is used to indicate any available implement for systemically administering a drug to a patient, including, but not limited to, a pre-filled syringe, a vial and syringe, an injection pen, an autoinjector, etc. With such items, a patient may self-administer the drug (i.e., administer the drug on their own behalf) or a physician may administer the drug.

General

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

Example

The objective of the following examples was:

To examine the effect of the EPO promoter polymorphism (rs1617640) on the response to LUCENTIS (ranibizumab) in patients with AMD and DME.

To examine the effect of the VEGF polymorphism (rs2010963) on the response to LUCENTIS (ranibizumab) in patients with AMD and DME.

To examine the additive effect of the two polymorphisms on the response to LUCENTIS (ranibizumab) in patients with AMD and DME.

Method Description

Samples and DNA Extraction

Two DME (CRFB002D2301 and CRFB002D2303) and three AMD clinical studies (CRFB002A2302, CBPD952A2309, and CBPD952A2308) were included in this pharmacogenetic assessment. One 10 mL blood sample was collected in a tube containing ethylene diamine tetra acetic acid (EDTA) for deoxyribonucleic acid (DNA) extraction. After the blood was drawn, the sample was inverted 8 to 10 times to prevent clotting. Genomic DNA was extracted from whole blood using the PUREGENE™ DNA Isolation Kit (D-50K) (Gentra, Minneapolis, Minn.).

Genotyping

A total of 316 DME and 458 wet-AMD patients were genotyped for the EPO promoter polymorphism (rs1617640) and the VEGF polymorphism (rs2010963), respectively. TaqMan Assays-by-Design and Assays-on-Demand was used on an ABI 7900 sequencer (Applied Biosystems, Foster City, Calif.). Genotyping used 5 ng of genomic DNA according to the manufacturer's instructions (Applied Biosystems, Foster City, Calif.). Genotyping call for each assay was >95%.

Clinical Variables

Mean value of best corrected visual acuity (BCVA) at baseline for the study eye.

Mean change in BCVA from baseline to 12 months for the study eye.

Number of Lucentis® injection.

Data Analysis

The intention to treat (ITT) population with last observation carried forward (LOCF) was used in the analysis. All patients with evaluable genotype data were included in the analysis. The two DME clinical trials, CRFB002D2301 and CRFB002D2303, were combined in the analysis to increase sample size. Similarly, the three AMD clinical studies, CRFB002A2302, CBPD952A2309 and CBPD952A2308, were also combined in the analysis.

A linear regression model was used to test for presence of an association between genetic factors and the clinical variables. Age, gender, race, study center, and baseline value were included in the model as covariates. Additive genetic model was evaluated. All statistical tests were two-tailed. P-values were not adjusted for multiple testing. SAS 9.2 was used.

Results

Demographic characteristics and baseline BCVA by EPO genotype A total of 301 DME and 453 wet-AMD patients had evaluable genotype data for the EPO promoter polymorphism (rs1617640), respectively. The genotype data did not deviate from Hardy-Weinberg equilibrium with p<0.05 in a chi-square test, so no evidence of genotyping failure or population admixture was seen. All patients with evaluable genotype data were included in the analysis. The demographic characteristics are summarized in Table 1 and Table 2. There was no significant difference of demographic characteristics between the EPO genotypes except the race in DME patients. Approximately 91% of DME patients with TT were Caucasians while only 39% of DME patients with GG were Caucasians.

TABLE 2

Demographics and baseline BCVA of AMD patients by EPO genotype

| | EPO genotype (rs1617640) | | | |
|---|---|---|---|---|
| Variable | GG (n = 163) | GT (n = 212) | TT (n = 78) | P-value |
| Age, yrs | 75.94 (8.13) | 76.98 (8.04) | 77.00 (7.49) | 0.409* |
| Race, % Caucasian | 96.32% | 97.64% | 97.44% | 0.861** |
| Gender, % female | 57.67% | 62.26% | 61.54% | 0.657** |
| Baseline BCVA | 55.47 (12.52) | 54.69 (13.58) | 56.96 (13.12) | 0.398*** |

Values are mean (SD).
BPD952A2309, BPD952A2308, and RFB002A2302 are combined.
*Non-parametric ANOVA
**Fisher's exact test
***ANCOVA adjusted for age, gender, and race.

There was a large percentage of Asians in one of the DME studies (Table 3). The result may suggest that the EPO genotype frequency is significantly different between Asian and Caucasian. As shown in Table 3, the TT frequency is significantly higher in Asian than in Caucasian (69.42% versus 34.12%). In addition, the EPO genotype frequency of Caucasian is very similar between DME and AMD. However, it remains unknown if the observed genotype frequency is suggestive of an association with the diseases because of lack of matched controls in the present study.

TABLE 3

EPO genotype frequency by race and disease

| | | EPO genotype (rs1617640) frequency | | | |
|---|---|---|---|---|---|
| Disease | Race | GG | GT | TT | P-value* |
| DME | Caucasian | 30 (17.65) | 82 (48.24) | 58 (34.12) | 2.20E−10 |
| | Asian | 2 (1.65) | 35 (28.93) | 84 (69.42) | |
| AMD | Caucasian | 76 (17.27) | 207 (47.05) | 157 (35.68) | 0.861 |
| | Asian | 0 (0.00) | 2 (66.67) | 1 (33.33) | |

Values are number of patients (%).
*Fisher's exact test

TABLE 1

Demographics and baseline BCVA of DME patients by EPO genotype

| | EPO genotype (rs1617640) | | | |
|---|---|---|---|---|
| Variable | GG (n = 147) | GT (n = 121) | TT (n = 33) | P-value |
| Age, yrs | 62.13 (8.60) | 62.31 (9.63) | 61.82 (9.09) | 0.918* |
| Race, % Caucasian | 39.46% | 67.77% | 90.91% | 2.3E−9** |
| Gender, % female | 47.62% | 38.84% | 45.45% | 0.336** |
| Baseline BCVA | 61.61 (10.93) | 61.18 (11.07) | 63.58 (10.33) | 0.255*** |

Values are mean (SD).
RFB002D2301 and RFB002D2303 are combined.
*Non-parametric ANOVA
**Fisher's exact test
***ANCOVA adjusted for age, gender, and race.

In addition, the effect of the EPO genotype on baseline visual acuity was tested. As shown in Table 1 and Table 2, there was no significant difference of baseline BCVA between the EPO genotypes.

Effect of the EPO promoter polymorphism on response to LUCENTIS® (ranibizumab) in DME patients Two DME clinical trials, CRFB002D2301 and CRFB002D2303, were combined in the testing for presence of an association between the EPO promoter polymorphism and response to LUCENTIS® (ranibizumab). There was a large percentage of Asians in the CRFB002D2303 study. But there was no significant difference of response to LUCENTIS® (ranibizumab) between Caucasian and Asian in the two studies combined. An ANCOVA model was performed to assess the effect of the EPO genotype on the primary clinical endpoint BCVA. The three treatment arms were analyzed separately. The results are presented in Table 4, FIG. 1, FIG. 2, and FIG. 3. The differences of response to LUCENTIS® (ranibizumab) were not significant between the genotype groups, except the LUCENTIS® (ranibizumab) monotherapy at month 3 and 5 (p<0.05). DME patients with the risk allele (T) tended to have less improvement of BCVA than those without the risk allele.

As showed in FIG. 1, FIG. 2, and FIG. 3, there was a high variability of response to Lucentis over 12 months of treatment in the overall clinical study. Therefore, an analysis for an average improvement of BCVA over 12 months was implemented to determine the overall efficacy of Lucentis in DME patients. An interesting trend of association between the EPO genotype and average improvement of BCVA was observed in patients treated with Lucentis alone (p<0.1). This result supports the findings at month 3 and 5.

TABLE 4

Effect of EPO genotype on BCVA response to LUCENTIS (ranibizumab) in patients with DME

| Clinical | Visit | Treatment | | GG | | GT | | TT | P-value* |
|---|---|---|---|---|---|---|---|---|---|
| Best corrected visual acuity (BCVA) | Baseline | Lucentis | n = 7 | 69.71 (7.18) | n = 40 | 61.43 (13.02) n = 55 | 62.13 (9.98) | 0.524 |
| | | Lucentis + Laser | n = 14 | 64.36 (9.55) | n = 41 | 60.56 (10.56) n = 49 | 60.06 (11.58) | 0.278 |
| | | Laser | n = 12 | 59.08 (11.31) | n = 40 | 61.58 (9.60) n = 43 | 62.70 (11.38) | 0.155 |
| | Month 1 | Lucentis | n = 7 | 5.57 (1.72) | n = 40 | 2.28 (5.86) n = 55 | 2.53 (4.41) | 0.154 |
| | | Lucentis + Laser | n = 14 | 1.93 (5.50) | n = 41 | 3.02 (5.00) n = 49 | 2.90 (5.28) | 0.374 |
| | | Laser | n = 12 | 2.92 (3.18) | n = 40 | 0.60 (6.91) n = 43 | −0.07 (5.08) | 0.982 |
| | Month 2 | Lucentis | n = 7 | 6.29 (5.22) | n = 40 | 4.80 (6.13) n = 55 | 3.62 (5.57) | 0.293 |
| | | Lucentis + Laser | n = 14 | 1.71 (4.81) | n = 40 | 5.85 (4.32) n = 49 | 3.76 (5.84) | 0.879 |
| | | Laser | n = 12 | 1.50 (8.53) | n = 40 | 0.75 (9.20) n = 43 | 0.72 (6.05) | 0.101 |
| | Month 3 | Lucentis | n = 7 | 9.43 (3.74) | n = 39 | 5.33 (7.14) n = 55 | 4.84 (5.64) | 0.018 |
| | | Lucentis + Laser | n = 14 | 4.21 (7.09) | n = 40 | 6.23 (5.23) n = 49 | 5.06 (5.99) | 0.692 |
| | | Laser | n = 10 | 1.60 (7.20) | n = 39 | 0.87 (8.01) n = 44 | 0.52 (5.77) | 0.381 |
| | Month 4 | Lucentis | n = 7 | 6.43 (5.29) | n = 37 | 4.76 (8.38) n = 55 | 5.33 (5.24) | 0.384 |
| | | Lucentis + Laser | n = 14 | 5.14 (4.88) | n = 39 | 6.10 (5.83) n = 49 | 3.73 (8.50) | 0.843 |
| | | Laser | n = 12 | 4.08 (6.35) | n = 38 | 0.13 (8.17) n = 44 | 2.45 (5.35) | 0.433 |
| | Month 5 | Lucentis | n = 7 | 9.43 (3.41) | n = 37 | 5.05 (6.44) n = 55 | 5.71 (6.62) | 0.047 |
| | | Lucentis + Laser | n = 14 | 5.36 (7.65) | n = 39 | 7.10 (6.02) n = 49 | 3.31 (9.16) | 0.410 |
| | | Laser | n = 12 | 1.92 (6.22) | n = 36 | 0.08 (8.83) n = 44 | 1.20 (5.54) | 0.469 |
| | Month 6 | Lucentis | n = 7 | 8.71 (6.10) | n = 38 | 6.42 (5.93) n = 51 | 6.45 (6.55) | 0.368 |
| | | Lucentis + Laser | n = 13 | 7.23 (7.34) | n = 39 | 7.54 (5.85) n = 48 | 3.92 (6.83) | 0.675 |
| | | Laser | n = 12 | 1.50 (7.61) | n = 33 | 2.33 (6.80) n = 43 | 1.30 (6.10) | 0.070 |
| | Month 7 | Lucentis | n = 7 | 11.57 (5.09) | n = 38 | 6.79 (7.75) n = 51 | 7.06 (5.63) | 0.051 |
| | | Lucentis + Laser | n = 12 | 7.25 (7.91) | n = 37 | 7.54 (6.54) n = 48 | 3.83 (7.07) | 0.299 |
| | | Laser | n = 11 | 1.09 (8.34) | n = 34 | 2.65 (8.47) n = 44 | 2.16 (6.08) | 0.133 |
| | Month 8 | Lucentis | n = 7 | 9.71 (7.61) | n = 37 | 5.73 (8.54) n = 51 | 6.69 (6.14) | 0.342 |
| | | Lucentis + Laser | n = 13 | 6.54 (7.50) | n = 39 | 9.08 (5.80) n = 46 | 3.61 (9.54) | 0.491 |
| | | Laser | n = 10 | 1.80 (10.77) | n = 34 | 2.09 (8.01) n = 42 | 1.40 (6.26) | 0.440 |
| | Month 9 | Lucentis | n = 7 | 7.71 (6.55) | n = 39 | 6.74 (7.08) n = 47 | 6.70 (5.64) | 0.131 |
| | | Lucentis + Laser | n = 12 | 5.17 (6.28) | n = 37 | 8.95 (5.70) n = 44 | 5.30 (8.71) | 0.593 |
| | | Laser | n = 11 | 0.55 (9.87) | n = 34 | 2.88 (8.17) n = 41 | 2.05 (7.17) | 0.268 |
| | Month 10 | Lucentis | n = 5 | 10.00 (8.37) | n = 33 | 6.91 (7.74) n = 50 | 7.36 (6.62) | 0.188 |
| | | Lucentis + Laser | n = 13 | 7.15 (6.56) | n = 40 | 8.53 (6.85) n = 43 | 5.19 (8.42) | 0.543 |
| | | Laser | n = 10 | 1.60 (8.24) | n = 34 | 2.15 (8.54) n = 39 | 1.10 (7.92) | 0.135 |
| | Month 11 | Lucentis | n = 7 | 7.86 (6.07) | n = 38 | 7.08 (8.17) n = 48 | 7.21 (6.75) | 0.463 |
| | | Lucentis + Laser | n = 13 | 7.46 (6.51) | n = 38 | 9.66 (6.05) n = 43 | 5.51 (10.42) | 0.379 |
| | | Laser | n = 10 | 1.50 (11.05) | n = 34 | 2.76 (8.53) n = 43 | 2.19 (5.46) | 0.447 |
| | Month 12 | Lucentis | n = 7 | 8.14 (5.46) | n = 39 | 6.64 (7.35) n = 52 | 7.60 (6.63) | 0.687 |
| | | Lucentis + Laser | n = 14 | 6.71 (6.56) | n = 39 | 8.46 (6.48) n = 48 | 4.58 (11.99) | 0.863 |
| | | Laser | n = 12 | 0.25 (9.74) | n = 41 | 1.56 (9.75) n = 43 | 2.26 (5.55) | 0.347 |
| | Month 12 (average change) | Lucentis | n = 7 | 8.30 (4.16) | n = 39 | 5.51 (5.93) n = 52 | 5.76 (4.67) | 0.099 |
| | | Lucentis + Laser | n = 14 | 5.27 (5.58) | n = 39 | 7.35 (4.56) n = 48 | 4.08 (6.61) | 0.651 |
| | | Laser | n = 12 | 1.68 (6.65) | n = 41 | 0.70 (8.16) n = 43 | 1.52 (4.48) | 0.156 |

Values are mean (SD).
ITT and LOCF population.
RFB002D2301 and RFB002D2303 are combined.
*ANCOVA adjusted for baseline value, study center, age, gender and race. Additive genetic model.

Effect of the EPO promoter polymorphism on response to LUCENTIS (ranibizumab) in AMD patients We expanded the EPO promoter polymorphism study to AMD patients to compare the genetic effect on response to LUCENTIS® (ranibizumab) between the two different diseases. Initially, the analysis for AMD patients was expected to have a negative outcome because there was no evidence of association between the EPO promoter polymorphism and AMD thus far.

Three AMD clinical trials, CRFB002A2302, CBPD952A2309 and CBPD952A2308, were combined in the testing for presence of an association between the EPO promoter polymorphism and response to LUCENTIS® (ranibizumab). An ANCOVA model was performed to assess the effect of EPO genotype on the primary clinical endpoint BCVA. The results are presented in Table 5, FIG. 4, FIG. 5, and FIG. 6.

Surprisingly, the effect of EPO genotype on BCVA improvement looked more obvious in AMD patients than in DME patients. The differences of response to LUCENTIS® (ranibizumab) monotherapy were significant between the genotype groups at month 7, 8, 9, 11, and 12 ($p<0.05$) (Table 5). A trend of association was also noted at month 5, 6 and 10 ($p<0.1$) (Table 5).

As showed in FIG. 4, the patients with GG genotype (n=44) started to perform better on BCVA than the patients with GT or TT genotypes in response to LUCENTIS® (ranibizumab) monotherapy from month 2. The patient with GT genotype (n=117) started to perform better than the patients with TT genotype (n=91) from month 6. The difference of BCVA improvement between the EPO genotypes was also much larger in AMD patients than the difference observed in the DME patients.

TABLE 5

Effect of EPO genotype on BCVA response to Lucentis in patients with AMD

| Clinical endpoint | Visit | Treatment | GG | | GT | | TT | | P-value* |
|---|---|---|---|---|---|---|---|---|---|
| | | | | | EPO genotype (rs1617640) | | | | |
| Best corrected visual acuity (BCVA) | Baseline | Lucentis | n = 44 | 55.18 (13.83) | n = 117 | 54.07 (14.45) | n = 91 | 56.23 (12.47) | 0.392 |
| | | Lucentis + Visudyne | n = 34 | 59.26 (11.95) | n = 95 | 55.45 (12.45) | n = 72 | 54.50 (12.62) | 0.378 |
| | Month 1 | Lucentis | n = 44 | 5.32 (6.52) | n = 117 | 3.86 (8.68) | n = 91 | 4.87 (8.78) | 0.999 |
| | | Lucentis + Visudyne | n = 34 | 0.62 (7.41) | n = 95 | 3.48 (10.72) | n = 72 | 4.03 (9.39) | 0.522 |
| | Month 2 | Lucentis | n = 44 | 7.11 (6.34) | n = 117 | 5.85 (9.70) | n = 90 | 5.46 (10.26) | 0.313 |
| | | Lucentis + Visudyne | n = 34 | 4.59 (11.31) | n = 95 | 5.37 (13.27) | n = 68 | 6.69 (11.64) | 0.819 |
| | Month 3 | Lucentis | n = 43 | 7.95 (9.67) | n = 117 | 6.50 (10.50) | n = 89 | 6.33 (11.31) | 0.428 |
| | | Lucentis + Visudyne | n = 34 | 4.59 (11.23) | n = 95 | 5.56 (13.35) | n = 64 | 6.84 (12.05) | 0.460 |
| | Month 4 | Lucentis | n = 44 | 8.36 (10.94) | n = 114 | 6.11 (11.80) | n = 87 | 7.16 (11.36) | 0.282 |
| | | Lucentis + Visudyne | n = 31 | 5.16 (11.55) | n = 89 | 5.91 (13.31) | n = 63 | 7.68 (12.19) | 0.810 |
| | Month 5 | Lucentis | n = 44 | 9.52 (10.53) | n = 115 | 6.36 (11.69) | n = 88 | 6.24 (12.22) | 0.055 |
| | | Lucentis + Visudyne | n = 27 | 4.52 (12.45) | n = 89 | 5.54 (14.31) | n = 61 | 5.49 (11.83) | 0.344 |
| | Month 6 | Lucentis | n = 44 | 9.11 (11.35) | n = 113 | 7.05 (12.23) | n = 88 | 6.26 (12.75) | 0.091 |
| | | Lucentis + Visudyne | n = 32 | 3.28 (10.60) | n = 86 | 5.70 (13.93) | n = 64 | 6.30 (13.37) | 0.635 |
| | Month 7 | Lucentis | n = 42 | 9.67 (16.52) | n = 113 | 7.01 (11.83) | n = 91 | 5.76 (12.88) | 0.011 |
| | | Lucentis + Visudyne | n = 29 | 4.38 (13.55) | n = 86 | 6.01 (14.92) | n = 62 | 4.61 (12.51) | 0.465 |
| | Month 8 | Lucentis | n = 43 | 8.63 (13.34) | n = 114 | 7.25 (11.88) | n = 87 | 4.00 (12.77) | 0.012 |
| | | Lucentis + Visudyne | n = 28 | 3.68 (12.52) | n = 84 | 6.89 (14.55) | n = 65 | 5.12 (12.70) | 0.754 |
| | Month 9 | Lucentis | n = 44 | 8.23 (12.75) | n = 111 | 7.11 (12.71) | n = 86 | 4.13 (13.34) | 0.020 |
| | | Lucentis + Visudyne | n = 28 | 4.75 (12.36) | n = 81 | 7.85 (13.42) | n = 61 | 5.51 (13.55) | 0.728 |
| | Month 10 | Lucentis | n = 43 | 9.16 (12.21) | n = 111 | 7.15 (12.78) | n = 84 | 4.60 (14.28) | 0.051 |
| | | Lucentis + Visudyne | n = 29 | 4.21 (11.93) | n = 83 | 5.13 (15.60) | n = 59 | 5.88 (13.97) | 0.889 |
| | Month 11 | Lucentis | n = 41 | 8.61 (11.92) | n = 104 | 7.02 (12.98) | n = 87 | 3.93 (13.65) | 0.010 |
| | | Lucentis + Visudyne | n = 27 | 3.15 (13.80) | n = 85 | 5.98 (15.63) | n = 62 | 4.63 (12.87) | 0.462 |
| | Month 12 | Lucentis | n = 43 | 9.12 (12.62) | n = 115 | 6.68 (14.07) | n = 91 | 3.78 (13.80) | 0.024 |
| | | Lucentis + Visudyne | n = 24 | 3.38 (12.82) | n = 87 | 5.46 (15.82) | n = 62 | 3.82 (14.28) | 0.552 |

Values are mean (SD).
ITT and LOCF population. BPD952A2309, BPD952A2308, and RFB002A2302 are combined.
*ANCOVA adjusted for baseline value, study center, age, gender and race. Additive genetic model.

Demographic Characteristics and Baseline BCVA by VEGF Genotype

We further expanded this pharmacogenetic analysis to the VEGF polymorphism (rs2010963) because VEGF is the target of LUCENTIS® (ranibizumab) and rs2010963 was associated with DR and AMD (Errera et al. (2007) Diabetes Care. 30(2):275-9; Janik-Papis K et al. (2009) Exp Mol Pathol. 87(3):234-8). Interestingly, a recent study demonstrated that the C allele of rs2010963 is associated with higher VEGF gene expression in the human retina A total of 306 DME and 456 wet-AMD patients had evaluable genotype data for the VEGF polymorphism, respectively. The genotype data did not deviate from Hardy-Weinberg equilibrium with p<0.05 in a chi-square test, so no evidence of genotyping failure or population admixture was seen. All patients with evaluable genotype data were included in the analysis.

The demographic characteristics are summarized in Table 6 and Table 7. Similar to the EPO genotype data, there was no significant difference of demographic characteristics between the VEGF genotypes except the race in DME patients. Approximately 65% of DME patients with GG were Caucasians while 38% of DME patients with CC were Caucasians. As mentioned above, the result may suggest that the VEGF genotype frequency is different between Asian and Caucasian. In addition, there was no significant difference of baseline BCVA between the VEGF genotypes (Table 6 and Table 7).

TABLE 6

Demographics and baseline BCVA of DME patients by VEGF genotype

| | VEGF genotype (rs2010963) | | | |
| --- | --- | --- | --- | --- |
| Variable | GG (n = 110) | CG (n = 143) | CC (n = 53) | P-value |
| Age, yrs | 63.31 (7.82) | 61.39 (9.52) | 61.70 (10.13) | 0.373* |
| Race, % Caucasian | 65.45% | 58.04% | 37.74% | 0.013** |
| Gender, % female | 43.64% | 41.26% | 50.94% | 0.484** |

TABLE 6-continued

Demographics and baseline BCVA of DME patients by VEGF genotype

| | VEGF genotype (rs2010963) | | | |
| --- | --- | --- | --- | --- |
| Variable | GG (n = 110) | CG (n = 143) | CC (n = 53) | P-value |
| Baseline BCVA | 60.46 (11.02) | 62.73 (10.66) | 61.89 (11.36) | 0.064*** |

Values are mean (SD).
RFB002D2301 and RFB002D2303 are combined.
*Non-parametric ANOVA
**Fisher's exact test
***ANCOVA adjusted for age, gender, and race.

TABLE 7

Demographics and baseline BCVA of AMD patients by VEGF genotype

| | VEGF genotype (rs2010963) | | | |
| --- | --- | --- | --- | --- |
| Variable | GG (n = 201) | CG (n = 210) | CC (n = 45) | P-value |
| Age, yrs | 76.74 (7.77) | 76.74 (8.34) | 74.93 (7.00) | 0.162* |
| Race, % Caucasian | 98.51% | 96.19% | 95.56% | 0.186** |
| Gender, % female | 60.70% | 58.10% | 71.11% | 0.274** |
| Baseline BCVA | 55.32 (13.21) | 55.09 (12.85) | 56.31 (14.62) | 0.636*** |

Values are mean (SD).
BPD952A2309, BPD952A2308, and RFB002A2302 are combined.
*Non-parametric ANOVA
**Fisher's exact test
***ANCOVA adjusted for age, gender, and race.

As shown in Table 8, the GG genotype frequency is significantly higher in Asian than in Caucasian (41.14% versus 28.10%). In addition, a similar frequency of the VEGF genotype between DME and AMD was observed in Caucasian.

TABLE 8

VEGF genotype frequency by race and disease

| | | VEGF genotype (rs2010963) frequency | | | |
| --- | --- | --- | --- | --- | --- |
| Disease | Race | GG | CG | CC | P-value* |
| DME | Caucasian | 72 (41.14) | 83 (47.43) | 20 (11.43) | 0.005 |
| | Asian | 34 (28.10) | 57 (47.11) | 30 (24.79) | |
| AMD | Caucasian | 198 (44.70) | 202 (45.60) | 43 (9.71) | 0.327 |
| | Asian | 0 (0.00) | 3 (100.00) | 0 (0.00) | |

Values are number of patients (%).
*Fisher's exact test

Effect of the VEGF Polymorphism on Response to LUCENTIS® (Ranibizumab) in DME Patients The two DME clinical trials were combined and an ANCOVA model was performed to assess the effect of the VEGF polymorphism on the primary clinical endpoint BCVA. The results are presented in Table 9, FIG. 6, FIG. 7, and FIG. 8. No significant differences of response to LUCENTIS® (ranibizumab) between the genotype groups were observed at any time points. There was a trend of association between VEGF genotype and BCVA improvement at month 10 and 11 for the patients who received LUCENTIS® (ranibizumab) monotherapy (p<0.1) (Table 9). DME patients with CC genotype tended to have less improvement of BCVA than those with CG or GG genotypes.

TABLE 9

Effect of VEGF genotype on BCVA response to LUCENTIS ® (ranibizumab) in patients with DME

| Clinical endpoint | Visit | Treatment | | GG | | CG | | CC | P-value* |
|---|---|---|---|---|---|---|---|---|---|
| Best corrected visual acuity (BCVA) | Baseline | Lucentis | n = 39 | 60.72 (11.59) | n = 50 | 64.14 (11.08) | n = 15 | 62.27 (10.71) | 0.407 |
| | | Lucentis + Laser | n = 36 | 61.08 (9.71) | n = 47 | 59.38 (11.49) | n = 23 | 63.43 (11.41) | 0.324 |
| | | Laser | n = 35 | 59.54 (11.85) | n = 46 | 64.63 (8.52) | n = 15 | 59.13 (12.15) | 0.433 |
| | Month 1 | Lucentis | n = 39 | 2.97 (5.12) | n = 50 | 2.30 (4.92) | n = 15 | 3.00 (4.49) | 0.370 |
| | | Lucentis + Laser | n = 36 | 2.36 (5.59) | n = 47 | 3.40 (5.78) | n = 23 | 2.61 (2.73) | 0.800 |
| | | Laser | n = 35 | 0.29 (5.41) | n = 46 | 0.91 (5.86) | n = 15 | 0.27 (6.49) | 0.734 |
| | Month 2 | Lucentis | n = 39 | 4.28 (5.04) | n = 49 | 5.06 (5.65) | n = 15 | 1.40 (7.21) | 0.935 |
| | | Lucentis + Laser | n = 36 | 4.06 (5.33) | n = 46 | 4.76 (6.01) | n = 23 | 4.00 (3.59) | 0.454 |
| | | Laser | n = 35 | 1.09 (8.34) | n = 46 | 0.15 (8.12) | n = 15 | 1.93 (4.67) | 0.488 |
| | Month 3 | Lucentis | n = 38 | 6.53 (5.28) | n = 50 | 4.70 (6.91) | n = 15 | 4.00 (5.82) | 0.821 |
| | | Lucentis + Laser | n = 36 | 4.58 (6.50) | n = 46 | 6.59 (5.96) | n = 23 | 4.17 (3.77) | 0.921 |
| | | Laser | n = 33 | 0.70 (5.07) | n = 46 | 0.57 (7.96) | n = 15 | 1.53 (6.91) | 0.493 |
| | Month 4 | Lucentis | n = 39 | 6.05 (7.18) | n = 48 | 5.23 (6.12) | n = 14 | 3.07 (5.61) | 0.877 |
| | | Lucentis + Laser | n = 36 | 5.00 (7.30) | n = 46 | 6.11 (6.38) | n = 22 | 2.32 (8.36) | 0.685 |
| | | Laser | n = 35 | 2.60 (5.41) | n = 46 | 0.52 (7.67) | n = 14 | 3.29 (6.59) | 0.969 |
| | Month 5 | Lucentis | n = 38 | 6.11 (5.47) | n = 48 | 6.15 (6.78) | n = 15 | 3.73 (7.24) | 0.987 |
| | | Lucentis + Laser | n = 35 | 4.77 (8.41) | n = 46 | 5.78 (7.13) | n = 23 | 4.35 (9.30) | 0.638 |
| | | Laser | n = 33 | 1.21 (5.69) | n = 46 | 0.26 (8.10) | n = 14 | 1.86 (6.19) | 0.947 |
| | Month 6 | Lucentis | n = 34 | 6.76 (4.49) | n = 50 | 6.64 (6.75) | n = 14 | 6.07 (7.88) | 0.322 |
| | | Lucentis + Laser | n = 35 | 5.63 (7.52) | n = 45 | 6.38 (7.10) | n = 22 | 5.18 (4.56) | 0.893 |
| | | Laser | n = 32 | 1.13 (6.61) | n = 43 | 1.79 (6.76) | n = 14 | 2.79 (5.54) | 0.334 |
| | Month 7 | Lucentis | n = 34 | 8.18 (5.46) | n = 49 | 7.27 (6.76) | n = 15 | 5.53 (7.96) | 0.911 |
| | | Lucentis + Laser | n = 33 | 5.45 (8.61) | n = 44 | 6.70 (6.33) | n = 22 | 4.73 (6.92) | 0.969 |
| | | Laser | n = 32 | 0.81 (7.97) | n = 44 | 2.52 (6.95) | n = 14 | 4.36 (6.17) | 0.301 |
| | Month 8 | Lucentis | n = 34 | 7.79 (5.69) | n = 49 | 5.94 (8.05) | n = 13 | 5.54 (7.59) | 0.840 |
| | | Lucentis + Laser | n = 35 | 6.66 (8.14) | n = 45 | 5.76 (9.74) | n = 20 | 7.05 (5.00) | 0.916 |
| | | Laser | n = 31 | 1.26 (7.61) | n = 43 | 1.70 (7.97) | n = 13 | 2.85 (5.41) | 0.616 |
| | Month 9 | Lucentis | n = 32 | 7.66 (5.26) | n = 49 | 6.71 (6.76) | n = 14 | 5.14 (6.54) | 0.388 |
| | | Lucentis + Laser | n = 34 | 7.12 (7.12) | n = 42 | 6.10 (9.04) | n = 19 | 8.00 (4.65) | 0.388 |
| | | Laser | n = 31 | 1.10 (7.43) | n = 43 | 2.63 (7.98) | n = 13 | 3.62 (8.61) | 0.210 |
| | Month 10 | Lucentis | n = 33 | 8.64 (6.85) | n = 45 | 7.27 (7.13) | n = 12 | 3.58 (6.35) | 0.057 |
| | | Lucentis + Laser | n = 35 | 6.74 (6.71) | n = 43 | 6.72 (9.28) | n = 20 | 7.65 (5.27) | 0.819 |
| | | Laser | n = 30 | 0.80 (6.96) | n = 41 | 1.37 (9.37) | n = 13 | 4.38 (5.71) | 0.274 |
| | Month 11 | Lucentis | n = 34 | 8.09 (7.40) | n = 47 | 7.32 (6.95) | n = 14 | 4.64 (7.32) | 0.083 |
| | | Lucentis + Laser | n = 34 | 7.53 (6.76) | n = 43 | 7.58 (11.09) | n = 19 | 7.32 (3.65) | 0.444 |
| | | Laser | n = 32 | 1.91 (6.93) | n = 43 | 1.91 (8.08) | n = 13 | 5.15 (6.05) | 0.436 |
| | Month 12 | Lucentis | n = 37 | 7.49 (6.71) | n = 49 | 7.45 (7.08) | n = 14 | 6.07 (5.85) | 0.709 |
| | | Lucentis + Laser | n = 37 | 7.05 (7.84) | n = 44 | 7.34 (9.14) | n = 22 | 4.05 (12.90) | 0.833 |
| | | Laser | n = 36 | 1.28 (7.58) | n = 46 | 1.00 (8.85) | n = 15 | 5.07 (5.69) | 0.284 |
| | Month 12 (average change) | Lucentis | n = 37 | 6.39 (4.34) | n = 49 | 5.99 (5.54) | n = 14 | 3.95 (5.47) | 0.845 |
| | | Lucentis + Laser | n = 37 | 5.52 (6.05) | n = 44 | 6.22 (5.94) | n = 22 | 4.51 (5.96) | 0.999 |
| | | Laser | n = 36 | 0.63 (6.10) | n = 46 | 1.03 (7.17) | n = 15 | 3.07 (4.83) | 0.468 |

Values are mean (SD).
ITT and LOCF population.
RFB002D2301 and RFB002D2303 are combined.
*ANCOVA adjusted for baseline value, study center, age, gender and race. Additive genetic model.

Effect of the VEGF Polymorphism on Response to LUCENTIS® (Ranibizumab) in AMD Patients The three AMD clinical trials were combined and the effect of the VEGF polymorphism on the primary clinical endpoint BCVA was tested by an ANCOVA model. The results are presented in Table 10, FIG. 9 and FIG. 10. The differences of response to LUCENTIS® (ranibizumab) monotherapy were significant between the genotype groups at month 3, 5, 8, 9, 10, and 11 ($p<0.05$). A trend was also noted at month 6 ($p<0.1$) (Table 10).

As showed in FIG. 9, the patients with CC genotype (n=27) only improved 1.48 letters when treated with Lucentis alone over 12 months. By contrast, the patients with CG (n=103) and GG (n=123) genotypes improved 6.25 and 6.77 letters, respectively.

risk alleles in the EPO and VEGF genes. The additive effect of the risk alleles on the primary clinical endpoint BCVA was tested by an ANCOVA model. This analysis was only performed for the AMD patients but not for DME patients due to extremely small number of patients in the group with 4 risk alleles. The results are presented in Table 11, FIG. 11 and FIG. 12.

The differences of response to LUCENTIS® (ranibizumab) monotherapy were significant between the risk groups at month 8, 9, and 11 ($p<0.05$). A trend was also noted at month 5, 6, and 10 ($p<0.1$) (Table 11). There was no significant difference of response to LUCENTIS (ranibizumab) monotherapy between the carriers of 0 (n=18), 1 (n=84) and 2 (n=92) risk alleles (FIG. 11). These patients improved approximately 7.5 letters over 12 month. By

TABLE 10

Effect of VEGF genotype on BCVA response to LUCENTIS (ranibizumab) in patients with AMD

| Clinical endpoint | Visit | Treatment | VEGF genotype (rs2010963) | | | P-value* |
|---|---|---|---|---|---|---|
| | | | GG | CG | CC | |
| Best corrected visual acuity (BCVA) | Baseline | Lucentis | n = 123   54.42 (13.70) | n = 103   54.99 (13.41) | n = 27   57.96 (14.38) | 0.433 |
| | | Lucentis + Visudyne | n = 78   56.74 (12.33) | n = 107   55.18 (12.35) | n = 18   53.83 (15.03) | 0.161 |
| | Month 1 | Lucentis | n = 123   4.25 (8.59) | n = 103   5.39 (7.89) | n = 27   1.70 (8.40) | 0.644 |
| | | Lucentis + Visudyne | n = 78   2.71 (9.72) | n = 107   3.62 (10.22) | n = 18   3.22 (7.55) | 0.736 |
| | Month 2 | Lucentis | n = 123   6.24 (9.57) | n = 102   6.52 (8.73) | n = 27   2.26 (10.44) | 0.170 |
| | | Lucentis + Visudyne | n = 76   4.58 (12.26) | n = 106   6.41 (12.72) | n = 17   6.94 (10.48) | 0.370 |
| | Month 3 | Lucentis | n = 122   7.34 (10.81) | n = 101   7.25 (9.39) | n = 27   1.22 (12.46) | 0.049 |
| | | Lucentis + Visudyne | n = 76   5.82 (12.01) | n = 103   5.87 (13.25) | n = 16   7.00 (11.15) | 0.965 |
| | Month 4 | Lucentis | n = 122   6.89 (12.53) | n = 101   7.65 (10.11) | n = 23   3.83 (11.08) | 0.618 |
| | | Lucentis + Visudyne | n = 71   5.30 (12.65) | n = 97   6.91 (12.76) | n = 17   9.18 (11.80) | 0.281 |
| | Month 5 | Lucentis | n = 122   8.01 (12.40) | n = 100   7.06 (9.87) | n = 26   1.23 (13.74) | 0.022 |
| | | Lucentis + Visudyne | n = 70   4.13 (13.61) | n = 94   5.86 (13.30) | n = 14   8.71 (8.71) | 0.251 |
| | Month 6 | Lucentis | n = 120   8.03 (12.52) | n = 103   7.54 (11.16) | n = 23   0.39 (14.23) | 0.052 |
| | | Lucentis + Visudyne | n = 71   3.70 (14.09) | n = 96   6.48 (12.83) | n = 17   8.47 (10.09) | 0.128 |
| | Month 7 | Lucentis | n = 119   7.73 (13.85) | n = 102   7.25 (12.11) | n = 26   2.04 (13.57) | 0.210 |
| | | Lucentis + Visudyne | n = 70   3.97 (14.61) | n = 92   5.82 (13.50) | n = 17   8.18 (11.74) | 0.294 |
| | Month 8 | Lucentis | n = 117   7.79 (13.24) | n = 101   5.93 (11.71) | n = 27   0.93 (12.69) | 0.027 |
| | | Lucentis + Visudyne | n = 67   5.73 (13.75) | n = 95   5.91 (14.05) | n = 17   6.47 (10.44) | 0.888 |
| | Month 9 | Lucentis | n = 116   8.40 (13.05) | n = 100   5.37 (11.85) | n = 26   −0.77 (15.38) | 0.002 |
| | | Lucentis + Visudyne | n = 66   6.14 (13.86) | n = 92   6.41 (13.45) | n = 14   10.93 (9.09) | 0.302 |
| | Month 10 | Lucentis | n = 114   8.39 (13.47) | n = 99   6.06 (12.23) | n = 26   0.69 (15.19) | 0.011 |
| | | Lucentis + Visudyne | n = 68   3.76 (15.59) | n = 91   5.95 (13.92) | n = 14   9.50 (10.65) | 0.222 |
| | Month 11 | Lucentis | n = 110   7.85 (13.17) | n = 97   5.85 (12.46) | n = 26   −0.04 (14.11) | 0.014 |
| | | Lucentis + Visudyne | n = 66   3.97 (16.36) | n = 95   5.68 (13.50) | n = 15   7.73 (10.07) | 0.342 |
| | Month 12 | Lucentis | n = 122   6.77 (14.37) | n = 101   6.25 (12.89) | n = 27   1.48 (14.62) | 0.195 |
| | | Lucentis + Visudyne | n = 66   2.94 (17.06) | n = 95   5.25 (13.63) | n = 14   8.93 (9.30) | 0.152 |

Values are mean (SD).
ITT and LOCF population.
BPD952A2309, BPD952A2308, and RFB002A2302 are combined.
*ANCOVA adjusted for baseline value, study center, age, gender and race. Additive genetic model.

Additive Effect of the EPO and VEGF Polymorphisms on Response to LUCENTIS® (Ranibizumab) in AMD Patients Response to treatment is complex and influenced by multiple factors. To test the possibility of an additive genetic effect on the response to LUCENTIS® (ranibizumab), the genotype data were stratified according to the number of the contrast, the carriers of 3 risk alleles (n=45) showed a moderate improvement (3.29 letters) while the carriers of 4 risk alleles (n=12) demonstrated a significant decline on BCVA (−4.75 letters) over 12 month. The overall results suggest a significant additive genetic effect of the two genes on the response to LUCENTIS® (ranibizumab).

TABLE 11

Additive effect of EPO and VEGF on BCVA response to LUCENTIS (ranibizumab) in patients with AMD

| Visit | Treatment | BCVA chenge by risk alleles of EPO and VEGF | | | | | | | |
|---|---|---|---|---|---|---|---|---|---|
| | | 0 | | 1 | | 2 | | | |
| Baseline | Lucentis | n = 18 | 56.33 (11.26) | n = 84 | 53.46 (14.72) | n = 92 | 55.16 (13.98) | | |
| | Lucentis + Visudyne | n = 14 | 58.57 (14.42) | n = 54 | 56.28 (12.20) | n = 80 | 56.70 (11.65) | | |
| Month 1 | Lucentis | n = 18 | 5.89 (8.25) | n = 84 | 4.05 (7.93) | n = 92 | 4.51 (8.58) | | |
| | Lucentis + Visudyne | n = 14 | −2.14 (6.98) | n = 54 | 4.33 (10.35) | n = 80 | 2.20 (9.55) | | |
| Month 2 | Lucentis | n = 18 | 6.72 (7.23) | n = 84 | 6.29 (9.41) | n = 92 | 6.57 (9.12) | | |
| | Lucentis + Visudyne | n = 14 | −0.43 (11.59) | n = 54 | 7.37 (12.67) | n = 78 | 4.17 (12.13) | | |
| Month 3 | Lucentis | n = 17 | 8.29 (11.53) | n = 84 | 6.49 (10.87) | n = 92 | 8.26 (9.08) | | |
| | Lucentis + Visudyne | n = 14 | 2.86 (11.30) | n = 54 | 6.81 (12.67) | n = 78 | 4.87 (12.71) | | |
| Month 4 | Lucentis | n = 18 | 7.50 (14.55) | n = 83 | 6.17 (12.52) | n = 91 | 8.30 (9.15) | | |
| | Lucentis + Visudyne | n = 14 | 4.29 (10.73) | n = 47 | 5.94 (14.17) | n = 75 | 5.61 (11.78) | | |
| Month 5 | Lucentis | n = 18 | 9.89 (13.34) | n = 84 | 7.27 (12.17) | n = 89 | 8.00 (9.81) | | |
| | Lucentis + Visudyne | n = 12 | 1.92 (14.72) | n = 48 | 6.46 (13.82) | n = 73 | 3.96 (13.26) | | |
| Month 6 | Lucentis | n = 18 | 9.33 (12.79) | n = 83 | 7.46 (12.81) | n = 90 | 8.38 (10.79) | | |
| | Lucentis + Visudyne | n = 13 | 2.08 (12.80) | n = 48 | 4.50 (14.53) | n = 75 | 5.13 (11.93) | | |
| Month 7 | Lucentis | n = 17 | 6.47 (21.33) | n = 81 | 8.64 (12.71) | n = 90 | 7.74 (11.40) | | |
| | Lucentis + Visudyne | n = 12 | 0.83 (13.47) | n = 46 | 6.80 (16.33) | n = 75 | 4.37 (12.59) | | |
| Month 8 | Lucentis | n = 17 | 8.76 (16.72) | n = 82 | 7.96 (12.57) | n = 88 | 7.14 (11.17) | | |
| | Lucentis + Visudyne | n = 10 | 2.90 (11.83) | n = 46 | 8.04 (15.08) | n = 74 | 3.85 (13.01) | | |
| Month 9 | Lucentis | n = 18 | 9.89 (15.39) | n = 81 | 8.12 (12.47) | n = 85 | 6.67 (11.80) | | |
| | Lucentis + Visudyne | n = 12 | −0.17 (10.66) | n = 44 | 10.36 (13.87) | n = 70 | 4.67 (12.80) | | |
| Month 10 | Lucentis | n = 18 | 9.17 (15.99) | n = 80 | 8.40 (12.08) | n = 84 | 7.36 (12.42) | | |
| | Lucentis + Visudyne | n = 13 | 3.00 (12.08) | n = 45 | 5.51 (16.68) | n = 71 | 3.63 (13.81) | | |
| Month 11 | Lucentis | n = 17 | 8.65 (14.76) | n = 74 | 8.41 (12.42) | n = 84 | 6.57 (12.27) | | |
| | Lucentis + Visudyne | n = 11 | 1.09 (13.74) | n = 45 | 6.62 (17.45) | n = 73 | 3.58 (13.80) | | |
| Month 12 | Lucentis | n = 17 | 8.00 (16.63) | n = 84 | 7.10 (14.02) | n = 90 | 7.42 (12.39) | | |
| | Lucentis + Visudyne | n = 10 | −1.30 (14.37) | n = 45 | 6.00 (17.24) | n = 73 | 3.74 (14.16) | | |

| Visit | Treatment | BCVA chenge by risk alleles of EPO and VEGF | | | | |
|---|---|---|---|---|---|---|
| | | 3 | | 4 | | P-value* |
| Baseline | Lucentis | n = 45 | 55.44 (11.79) | n = 12 | 62.50 (12.17) | 0.079 |
| | Lucentis + Visudyne | n = 46 | 54.23 (12.66) | n = 7 | 45.57 (16.20) | 0.104 |
| Month 1 | Lucentis | n = 45 | 5.31 (8.29) | n = 12 | 1.08 10.20) | 0.442 |
| | Lucentis + Visudyne | n = 46 | 5.09 (9.72) | n = 7 | 4.00 (10.57) | 0.338 |
| Month 2 | Lucentis | n = 44 | 5.11 (9.28) | n = 12 | 0.08 13.79) | 0.316 |
| | Lucentis + Visudyne | n = 45 | 7.84 (12.06) | n = 6 | 8.50 13.35) | 0.693 |
| Month 3 | Lucentis | n = 43 | 5.42 (10.13) | n = 12 | −3.00 (15.37) | 0.468 |
| | Lucentis + Visudyne | n = 42 | 6.38 (12.56) | n = 5 | 13.20 (12.03) | 0.514 |
| Month 4 | Lucentis | n = 43 | 6.63 (11.91) | n = 9 | −0.33 (13.64) | 0.871 |
| | Lucentis + Visudyne | n = 41 | 7.73 (13.14) | n = 6 | 15.50 (8.55) | 0.787 |
| Month 5 | Lucentis | n = 44 | 5.45 (11.64) | n = 11 | −3.55 (15.54) | 0.076 |
| | Lucentis + Visudyne | n = 38 | 6.68 (12.10) | n = 6 | 12.33 (7.92) | 0.477 |
| Month 6 | Lucentis | n = 42 | 5.83 (11.32) | n = 11 | −4.64 (17.12) | 0.100 |
| | Lucentis + Visudyne | n = 40 | 7.28 (14.29) | n = 6 | 13.17 (8.47) | 0.524 |
| Month 7 | Lucentis | n = 45 | 5.11 (12.42) | n = 12 | −2.50 (13.85) | 0.128 |
| | Lucentis + Visudyne | n = 38 | 5.39 (13.43) | n = 6 | 12.33 (11.08) | 0.564 |
| Month 8 | Lucentis | n = 44 | 3.59 (12.37) | n = 12 | −4.42 (11.38) | 0.038 |
| | Lucentis + Visudyne | n = 41 | 6.78 (13.58) | n = 6 | 8.83 9.54) | 0.605 |
| Month 9 | Lucentis | n = 45 | 3.53 (12.84) | n = 11 | −6.36 (15.55) | 0.014 |
| | Lucentis + Visudyne | n = 39 | 6.28 (13.52) | n = 5 | 15.80 (7.19) | 0.836 |

TABLE 11-continued

Additive effect of EPO and VEGF on BCVA response to LUCENTIS (ranibizumab) in patients with AMD

|  |  |  |  |  |  |
|---|---|---|---|---|---|
| Month 10 | Lucentis | n = 43 | 3.81 (13.87) | n = 12 | −4.50 (15.92) | 0.074 |
|  | Lucentis + Visudyne | n = 37 | 7.35 (13.71) | n = 5 | 15.60 (7.92) | 0.804 |
| Month 11 | Lucentis | n = 44 | 3.50 (13.56) | n = 12 | −4.67 (14.93) | 0.027 |
|  | Lucentis + Visudyne | n = 39 | 6.15 (12.42) | n = 6 | 11.50 (5.79) | 0.554 |
| Month 12 | Lucentis | n = 45 | 3.29 (13.63) | n = 12 | −4.75 (15.44) | 0.169 |
|  | Lucentis + Visudyne | n = 39 | 5.00 (14.05) | n = 6 | 11.33 (6.89) | 0.785 |

Values are mean (SD).
ITT and LOCF population.
BPD952A2309, BPD952A2308, and RFB002A2302 are combined.
*ANCOVA model adjusted for baseline value, study center, age, gender and race. Additive genetic model.

What is claimed is:

1. A method of treating age-related macular degeneration (AMD) in a patient in need thereof, comprising 1) assaying a biological sample from the patient for a single allele having a guanine at the locus rs1617640, or two alleles having a guanine at the locus rs1617640, and 2) administering a therapeutically effective amount of ranibizumab to the patient, wherein the patient has a single allele having a guanine at the locus rs1617640, or two alleles having a guanine at the locus rs1617640.

2. The method of claim 1, wherein the patient administered with the therapeutically effective amount of ranibizumab exhibits an improvement of best corrected visual acuity (BCVA) at baseline.

3. The method of claim 1, wherein the patient has a single allele having a guanine at the locus rs1617640.

4. The method of claim 1, wherein the patient has two alleles having a guanine at the locus rs1617640.

5. The method of claim 1, wherein the patient is further treated with a therapeutically effective amount of an EPO antagonist.

6. The method of claim 5, wherein the EPO antagonist comprises VH and VL sequences selected from the group consisting of SEQ ID NOs: 13 and 14, SEQ ID NOs: 33 and 34, SEQ ID NOs: 53 and 54, and SEQ ID NOs: 73 and 74, respectively.

* * * * *

SEQUENCE LISTING

```
<160> NUMBER OF SEQ ID NOS: 91

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 2

Gly Ile Asp Pro Ile Ser Gly Phe Ala Asp Tyr Ala Gln Lys Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 3

Glu Leu Tyr Tyr Pro Gly Thr Trp Met Ala Val Met Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 4

Ser Gly Asp Asn Ile Pro Glu Tyr Tyr Val His
1               5                   10

<210> SEQ ID NO 5
```

<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 5

Arg Asp Asn Glu Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 6

Gln Val Phe Asp Glu Ser Ser Trp His Trp Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Gly Gly Thr Phe Arg Ser Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 8

Asp Pro Ile Ser Gly Phe
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 9

Glu Leu Tyr Tyr Pro Gly Thr Trp Met Ala Val Met Ala Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 10

Asp Asn Ile Pro Glu Tyr Tyr
1               5

<210> SEQ ID NO 11
<211> LENGTH: 3

```
<212> TYPE: PRT
<213> ORGANISM: Artificial Sequence
<220> FEATURE:
<223> OTHER INFORMATION: Synthetic polypeptide

<400> SEQUENCE: 11

Arg Asp Asn
1

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Phe Asp Glu Ser Ser Trp His Trp
1               5

<210> SEQ ID NO 13
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Ile Ser Trp Val Arg Gln Ala Pro Gly Gln Gly Leu Glu Trp Met
        35                  40                  45

Gly Gly Ile Asp Pro Ile Ser Gly Phe Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Tyr Tyr Pro Gly Thr Trp Met Ala Val Met Ala Tyr
            100                 105                 110

Trp Gly Arg Gly Thr Leu Val Thr Val Ser Ser
        115                 120

<210> SEQ ID NO 14
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 14

Ser Tyr Val Leu Thr Gln Pro Pro Ser Val Ser Val Ala Pro Gly Lys
1               5                   10                  15

Thr Ala Arg Ile Thr Cys Ser Gly Asp Asn Ile Pro Glu Tyr Tyr Val
            20                  25                  30

His Trp Tyr Gln Gln Lys Pro Gly Gln Ala Pro Val Leu Val Ile Tyr
        35                  40                  45

Arg Asp Asn Glu Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Phe Asp Glu Ser Ser Trp His
                 85                  90                  95

Trp Val Phe Gly Gly Gly Thr Lys Leu Thr Val Leu
            100                 105

<210> SEQ ID NO 15
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 15

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Arg Ser Tyr
                20                  25                  30

Ala Ile Ser Trp Val Arg Gln Ala Pro Gly Gln Gly Leu Glu Trp Met
            35                  40                  45

Gly Gly Ile Asp Pro Ile Ser Gly Phe Ala Asp Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Leu Tyr Tyr Pro Gly Thr Trp Met Ala Val Met Ala Tyr
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys
225

<210> SEQ ID NO 16
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 16

Ser Tyr Val Leu Thr Gln Pro Pro Ser Val Ser Val Ala Pro Gly Lys
 1               5                  10                  15

Thr Ala Arg Ile Thr Cys Ser Gly Asp Asn Ile Pro Glu Tyr Tyr Val
                20                  25                  30
```

His Trp Tyr Gln Gln Lys Pro Gly Gln Ala Pro Val Leu Val Ile Tyr
            35                  40                  45

Arg Asp Asn Glu Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Phe Asp Glu Ser Ser Trp His
                 85                  90                  95

Trp Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 17
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 17
caggtgcagc tggtgcagtc aggcgccgaa gtgaagaaac ccggctctag cgtgaaggtg      60
tcctgtaaag ctagtggcgg cacctttaga tcctacgcta ttagctgggt gcgacaggct     120
ccaggccagg gcctcgaatg gatgggcggc atcgacccta ttagcggctt cgccgactac    180
gctcagaaat tcagggcag agtgactatc accgccacg agtctactag caccgcctac     240
atggaactgt ctagcctgag atcagaggac accgccgtgt actactgcgc tagagagctg   300 tactacccccg gcacctggat ggccgtgatg gccattggg gcagaggcac cctggtgaca    360
gtgtcttct                                                             369

<210> SEQ ID NO 18
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 18
agctacgtgc tgacccagcc ccctagcgtg tcagtggccc ctggcaagac cgctagaatc       60
acctgtagcg gcgataacat ccccgagtac tacgtgcact ggtatcagca gaagcccggc     120
caggcccccg tgctggtgat ctatagagat aacgagcggc ctagcggcat ccccgagcgg    180
ttttccggct ctaatagcgg caacaccgct accctgacta tttcaagagt ggaagccggc     240

```
gacgaggccg actactactg tcaggtgttc gacgagtctt catggcactg ggtgttcggc    300
ggaggcacca agctgaccgt gctg                                            324
```

<210> SEQ ID NO 19
<211> LENGTH: 678
<212> TYPE: DNA
<213> ORGANISM: Artificial Sequence
<220> FEATURE:
<223> OTHER INFORMATION: Synthetic polynucleotide

<400> SEQUENCE: 19

```
caggtgcagc tggtgcagtc aggcgccgaa gtgaagaaac ccggctctag cgtgaaggtg     60
tcctgtaaag ctagtggcgg cacctttaga tcctacgcta ttagctgggt gcgacaggct    120
ccaggccagg gcctcgaatg gatgggcggc atcgacccta ttagcggctt cgccgactac    180
gctcagaaat tcagggcag agtgactatc accgccgacg agtctactag caccgcctac    240
atggaactgt ctagcctgag atcagaggac accgccgtgt actactgcgc tagagagctg    300
tactaccccg gcacctggat ggccgtgatg gcctattggg gcagaggcac cctggtgaca    360
gtgtcttctg ctagcactaa gggccctcc gtgttccctc tggccccttc cagcaagtct    420
acctctggcg gcaccgctgc tctgggctgc ctggtgaagg actacttccc tgagcctgtg    480
acagtgtcct ggaactctgg cgccctgacc tccggcgtgc acaccttccc tgccgtgctg    540
cagtcctccg gcctgtactc cctgtcctcc gtggtgacag tgccttcctc cagcctgggc    600
acccagacct atatctgcaa cgtgaaccac aagccttcca caccaaggt ggacaagcgg    660 gtggagccta agtcatgc                                                  678
```

<210> SEQ ID NO 20
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 20

```
agctacgtgc tgacccagcc ccctagcgtg tcagtggccc ctggcaagac cgctagaatc     60
acctgtagcg gcgataacat ccccgagtac tacgtgcact ggtatcagca gaagcccggc    120
caggcccccg tgctggtgat ctatagagat aacgagcggc ctagcggcat ccccgagcgg    180
ttttccggct ctaatagcgg caacaccgct accctgacta tttcaagagt ggaagccggc    240
gacgaggccg actactactg tcaggtgttc gacgagtctt catggcactg ggtgttcggc    300
ggaggcacca agctgaccgt gctgggccag cctaaggctg cccccagcgt gaccctgttc    360 cccccagca gcgaggagct gcaggccaac aaggccaccc tggtgtgcct gatcagcgac    420
ttctacccag gcgccgtgac cgtggcctgg aaggccgaca gcagcccgt gaaggccggc    480 gtggagacca ccaccccag caagcagagc aacaacaagt acgccgccag cagctacctg    540
agcctgaccc ccgagcagtg gaagagccac aggtcctaca gctgccaggt gacccacgag    600
ggcagcaccg tggaaaagac cgtggcccca accgagtgca gc                       642
```

<210> SEQ ID NO 21
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 21

Ser Tyr Trp Ile Gly
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 22

Trp Ile Asp Pro Tyr Arg Ser Glu Ile Arg Tyr Ser Pro Ser Phe Gln
1               5                   10                  15

Gly

<210> SEQ ID NO 23
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 23

Val Ser Ser Glu Pro Phe Asp Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 24

Ser Gly Asp Lys Leu Gly Asp His Tyr Ala Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 25

Asp Asp Ser Lys Arg Pro Ser
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 26

Ala Thr Trp Thr Phe Glu Gly Asp Tyr Val
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic polypeptide

```
<400> SEQUENCE: 27

Gly Tyr Ser Phe Thr Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 28

Asp Pro Tyr Arg Ser Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 29

Val Ser Ser Glu Pro Phe Asp Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 30

Asp Lys Leu Gly Asp His Tyr
1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 31

Asp Asp Ser
1

<210> SEQ ID NO 32
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 32

Trp Thr Phe Glu Gly Asp Tyr
1               5

<210> SEQ ID NO 33
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 33
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Trp Ile Asp Pro Tyr Arg Ser Glu Ile Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Ser Glu Pro Phe Asp Ser Trp Gly Gln Gly Thr Leu
            100                 105                 110

Val Thr Val Ser Ser
            115

<210> SEQ ID NO 34
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 34

Ser Tyr Val Leu Thr Gln Pro Pro Ser Val Ser Val Ala Pro Gly Lys
1               5                   10                  15

Thr Ala Arg Ile Thr Cys Ser Gly Asp Lys Leu Gly Asp His Tyr Ala
                20                  25                  30

Tyr Trp Tyr Gln Gln Lys Pro Gly Gln Ala Pro Val Leu Val Ile Tyr
            35                  40                  45

Asp Asp Ser Lys Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Ala Thr Trp Thr Phe Gly Asp Tyr
                85                  90                  95

Val Phe Gly Gly Gly Thr Lys Leu Thr Val Leu
            100                 105

<210> SEQ ID NO 35
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Trp Ile Asp Pro Tyr Arg Ser Glu Ile Arg Tyr Ser Pro Ser Phe
50                  55                  60

Gln Gly Gln Val Thr Ile Ser Ala Asp Lys Ser Ile Ser Thr Ala Tyr

```
              65                  70                  75                  80
Leu Gln Trp Ser Ser Leu Lys Ala Ser Asp Thr Ala Met Tyr Tyr Cys
                85                  90                  95

Ala Arg Val Ser Ser Glu Pro Phe Asp Ser Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys
    210                 215                 220

<210> SEQ ID NO 36
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 36

Ser Tyr Val Leu Thr Gln Pro Pro Ser Val Ser Val Ala Pro Gly Lys
1               5                   10                  15

Thr Ala Arg Ile Thr Cys Ser Gly Asp Lys Leu Gly Asp His Tyr Ala
            20                  25                  30

Tyr Trp Tyr Gln Gln Lys Pro Gly Gln Ala Pro Val Leu Val Ile Tyr
        35                  40                  45

Asp Asp Ser Lys Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Ala Thr Trp Thr Phe Glu Gly Asp Tyr
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
```

<210> SEQ ID NO 37
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 37

| gaggtgcagc tggtgcagtc aggcgccgaa gtgaagaagc cggcgagtc actgaagatt | 60 |
| agctgtaaag gctcaggcta tagcttcact agctactgga tcggctgggt gcgacagatg | 120 |
| cccggcaagg gcctggaatg gatgggctgg atcgacccct atagatcaga gattaggtat | 180 |
| agccctagct ttcagggcca ggtgacaatt agcgccgata agtctattag caccgcctac | 240 |
| ctgcagtggt ctagcctgaa ggctagtgac accgctatgt actactgcgc tagagtgtct | 300 |
| agcgagccct tcgatagctg gggccagggc accctggtga cagtgtcttc a | 351 |

<210> SEQ ID NO 38
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 38

| agctacgtgc tgacccagcc ccctagcgtg tcagtggccc ctggcaagac cgctagaatc | 60 |
| acctgtagcg gcgataagct gggcgatcac tacgcctact ggtatcagca gaagcccggc | 120 |
| caggccccg tgctggtgat ctacgacgac tctaagcggc ctagcggcat ccccgagcgg | 180 |
| tttagcggct ctaatagcgg caacaccgct accctgacta tttcaagagt ggaagccggc | 240 |
| gacgaggccg actactactg cgctacctgg accttcgagg gcgactacgt gttcggcgga | 300 |
| ggcactaagc tgaccgtgct g | 321 |

<210> SEQ ID NO 39
<211> LENGTH: 660
<212> TYPE: DNA
<213> ORGANISM: Artificial Sequence
<220> FEATURE:
<223> OTHER INFORMATION: Synthetic polynucleotide

<400> SEQUENCE: 39

| gaggtgcagc tggtgcagtc aggcgccgaa gtgaagaagc cggcgagtc actgaagatt | 60 |
| agctgtaaag gctcaggcta tagcttcact agctactgga tcggctgggt gcgacagatg | 120 |
| cccggcaagg gcctggaatg gatgggctgg atcgacccct atagatcaga gattaggtat | 180 |
| agccctagct ttcagggcca ggtgacaatt agcgccgata agtctattag caccgcctac | 240 |
| ctgcagtggt ctagcctgaa ggctagtgac accgctatgt actactgcgc tagagtgtct | 300 |
| agcgagccct tcgatagctg gggccagggc accctggtga cagtgtcttc agctagcact | 360 |
| aagggcccct ccgtgttccc tctggcccct tccagcaagt ctacctctgg cggcaccgct | 420 |
| gctctgggct gcctggtgaa ggactacttc cctgagcctg tgacagtgtc ctggaactct | 480 |
| ggcgccctga cctccggcgt gcacaccttc cctgccgtgc tgcagtcctc cggcctgtac | 540 |
| tccctgtcct ccgtggtgac agtgccttcc tccagcctgg gcacccagac ctatatctgc | 600 |
| aacgtgaacc acaagccttc caacaccaag gtggacaagc gggtggagcc taagtcatgc | 660 |

<210> SEQ ID NO 40
<211> LENGTH: 639
<212> TYPE: DNA
<213> ORGANISM: Artificial Sequence
<220> FEATURE:
<223> OTHER INFORMATION: Synthetic polynucleotide

<400> SEQUENCE: 40

```
agctacgtgc tgacccagcc ccctagcgtg tcagtggccc ctggcaagac cgctagaatc      60
acctgtagcg gcgataagct gggcgatcac tacgcctact ggtatcagca gaagcccggc     120
caggcccccg tgctggtgat ctacgacgac tctaagcggc ctagcggcat ccccgagcgg     180
tttagcggct ctaatagcgg caacaccgct accctgacta tttcaagagt ggaagccggc     240
gacgaggccg actactactg cgctacctgg accttcgagg gcgactacgt gttcggcgga     300
ggcactaagc tgaccgtgct gggccagcct aaggctgccc ccagcgtgac cctgttcccc     360
cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca ccccccagca gcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggccccaacc gagtgcagc                            639
```

<210> SEQ ID NO 41
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 41

Ser Asn Thr Ala Ala Trp Asn
1               5

<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

Val Ile Tyr Tyr Arg Ser Lys Trp Tyr Asn Asp Tyr Ala Val Ser Val
1               5                   10                  15

Lys Ser

<210> SEQ ID NO 43
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 43

Ser Val Pro Gly Gly Asp Pro Gly Leu Glu His Ala Phe Ala Tyr
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 44

Ser Gly Asp Asn Leu Gly Thr Tyr Tyr Val Glu
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 45

Asp Asp Ser Asp Arg Pro Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 46

Ala Ser Phe Ala Ser Trp Ser Asp Ser Val
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 47

Gly Asp Ser Val Ser Ser Asn Thr Ala
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 48

Tyr Tyr Arg Ser Lys Trp Tyr
1               5

<210> SEQ ID NO 49
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 49

Ser Val Pro Gly Gly Asp Pro Gly Leu Glu His Ala Phe Ala Tyr
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 50

Asp Asn Leu Gly Thr Tyr Tyr
1               5

<210> SEQ ID NO 51
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 51

Asp Asp Ser
1

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 52

Phe Ala Ser Trp Ser Asp Ser
1               5

<210> SEQ ID NO 53
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 53

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Thr Ala Ala Trp Asn Trp Ile Arg Gln Ser Pro Ser Arg Gly Leu Glu
        35                  40                  45

Trp Leu Gly Val Ile Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Val Pro Gly Gly Asp Pro Gly Leu Glu His
            100                 105                 110

Ala Phe Ala Tyr Trp Gly Arg Gly Thr Leu Val Thr Val Ser Ser
        115                 120                 125

<210> SEQ ID NO 54
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 54

Ser Tyr Val Leu Thr Gln Pro Pro Ser Val Ser Val Ala Pro Gly Lys
1               5                   10                  15

Thr Ala Arg Ile Thr Cys Ser Gly Asp Asn Leu Gly Thr Tyr Tyr Val

```
                     20                  25                  30
Glu Trp Tyr Gln Gln Lys Pro Gly Gln Ala Pro Val Leu Val Ile Tyr
             35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Ala Ser Phe Ala Ser Trp Ser Asp Ser
                 85                  90                  95

Val Phe Gly Gly Gly Thr Lys Leu Thr Val Leu
            100                 105
```

<210> SEQ ID NO 55
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 55

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Thr Ala Ala Trp Asn Trp Ile Arg Gln Ser Pro Ser Arg Gly Leu Glu
         35                  40                  45

Trp Leu Gly Val Ile Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Ser Val Pro Gly Gly Asp Pro Gly Leu Glu His
            100                 105                 110

Ala Phe Ala Tyr Trp Gly Arg Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys
225                 230
```

<210> SEQ ID NO 56
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 56

Ser Tyr Val Leu Thr Gln Pro Pro Ser Val Ser Val Ala Pro Gly Lys
1               5                   10                  15

Thr Ala Arg Ile Thr Cys Ser Gly Asp Asn Leu Gly Thr Tyr Tyr Val
                20                  25                  30

Glu Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Ala Ser Phe Ala Ser Trp Ser Asp Ser
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
        210

<210> SEQ ID NO 57
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 57
caggtgcagc tgcagcagtc aggccctggc ctggtgaaac ctagtcagac cctgagcctg      60
acctgcgcta ttagcggcga tagcgtgtca tctaacaccg ccgcctggaa ctggattaga     120
cagtcaccta gtagaggcct ggaatggctg ggcgtgatct actataggtc taagtggtac     180
aacgactacg ccgtgtcagt gaagtctagg atcactatta accccgacac ctctaagaat     240
cagttcagcc tgcagctgaa tagcgtgacc cccgaggaca ccgccgtgta ctactgcgct     300
agatcagtgc ctggcggcga ccccggcctg gaacacgcct ttgcctactg gggcagaggc     360
accctggtga cagtgtcttc t                                               381

<210> SEQ ID NO 58
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 58

```
agctacgtgc tgacccagcc ccctagcgtg tcagtggccc ctggcaagac cgctagaatc    60
acctgtagcg gcgataacct gggcacctac tacgtggaat ggtatcagca gaagcccggc   120
caggcccccg tgctggtgat ctacgacgat agcgatagac ctagcggcat ccccgagcgg   180
tttagcggct ctaatagcgg caacaccgct accctgacta ttagtagagt ggaagccggc   240
gacgaggccg actactactg cgctagtttc gctagttgga gcgattcagt gttcggcgga   300
ggcactaagc tgaccgtgct g                                             321
```

<210> SEQ ID NO 59
<211> LENGTH: 690
<212> TYPE: DNA
<213> ORGANISM: Artificial Sequence
<220> FEATURE:
<223> OTHER INFORMATION: Synthetic polynucleotide

<400> SEQUENCE: 59

```
caggtgcagc tgcagcagtc aggccctggc ctggtgaaac ctagtcagac cctgagcctg    60
acctgcgcta ttagcggcga tagcgtgtca tctaacaccg ccgcctggaa ctggattaga   120
cagtcaccta gtagaggcct ggaatggctg ggcgtgatct actataggtc taagtggtac   180
aacgactacg ccgtgtcagt gaagtctagg atcactatta accccgacac ctctaagaat   240
cagttcagcc tgcagctgaa tagcgtgacc cccgaggaca ccgccgtgta ctactgcgct   300
agatcagtgc ctggcggcga ccccggcctg aacacgcct ttgcctactg gggcagaggc    360
accctggtga cagtgtcttc tgctagcact aagggcccct ccgtgttccc tctggcccct   420
tccagcaagt ctacctctgg cggcaccgct gctctgggct gctggtgaa ggactacttc    480 cctgagcctg tgacagtgtc ctggaactct ggcgccctga cctccggcgt gcacaccttc   540
cctgccgtgc tgcagtcctc cggcctgtac tccctgtcct ccgtggtgac agtgccttcc   600
tccagcctgg gcacccagac ctatatctgc aacgtgaacc acaagccttc caacaccaag   660
gtggacaagc gggtggagcc taagtcatgc                                     690
```

<210> SEQ ID NO 60
<211> LENGTH: 639
<212> TYPE: DNA
<213> ORGANISM: Artificial Sequence
<220> FEATURE:
<223> OTHER INFORMATION: Synthetic polynucleotide

<400> SEQUENCE: 60

```
agctacgtgc tgacccagcc ccctagcgtg tcagtggccc ctggcaagac cgctagaatc    60
acctgtagcg gcgataacct gggcacctac tacgtggaat ggtatcagca gaagcccggc   120
caggcccccg tgctggtgat ctacgacgat agcgatagac ctagcggcat ccccgagcgg   180
tttagcggct ctaatagcgg caacaccgct accctgacta ttagtagagt ggaagccggc   240
gacgaggccg actactactg cgctagtttc gctagttgga gcgattcagt gttcggcgga   300
ggcactaagc tgaccgtgct gggccagcct aaggctgccc ccagcgtgac cctgttcccc   360
cccagcagcg aggagctgca ggccaacaag gccaccctgg tgtgcctgat cagcgacttc   420
tacccaggcg ccgtgaccgt ggcctggaag gccgacagca gccccgtgaa ggccggcgtg   480
gagaccacca cccccagcaa gcagagcaac aacaagtacg ccgccagcag ctacctgagc   540
ctgacccccg agcagtggaa gagccacagg tcctacagct gccaggtgac ccacgagggc   600
agcaccgtgg aaaagaccgt ggccccaacc gagtgcagc                          639
```

```
<210> SEQ ID NO 61
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 61

Ser Tyr Tyr Met Ser
1               5

<210> SEQ ID NO 62
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 62

Trp Ile Asn Pro Leu Lys Gly Asn Thr Asn Tyr Ala Gln Lys Phe Gln
1               5                   10                  15

Gly

<210> SEQ ID NO 63
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 63

Glu Gly Met Tyr Phe Asp Ile
1               5

<210> SEQ ID NO 64
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 64

Ser Gly Asp Ser Ile Gly Asp Lys Tyr Val Tyr
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 65

Asp Thr Asn Lys Arg Pro Ser
1               5

<210> SEQ ID NO 66
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 66

Gln Ser Trp Asp Leu Asp Phe Asn Thr Tyr Val
1               5                   10
```

```
<210> SEQ ID NO 67
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 67

Gly Tyr Thr Phe Thr Ser Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 68

Asn Pro Leu Lys Gly Asn
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 69

Glu Gly Met Tyr Phe Asp Ile
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 70

Asp Ser Ile Gly Asp Lys Tyr
1               5

<210> SEQ ID NO 71
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 71

Asp Thr Asn
1

<210> SEQ ID NO 72
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 72

Trp Asp Leu Asp Phe Asn Thr Tyr
1               5
```

```
<210> SEQ ID NO 73
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 73
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Ser Trp Val Arg Gln Ala Pro Gly Gln Gly Leu Glu Trp Met
            35                  40                  45

Gly Trp Ile Asn Pro Leu Lys Gly Asn Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Gly Met Tyr Phe Asp Ile Trp Gly Gln Gly Thr Leu Val
            100                 105                 110

Thr Val Ser Ser
        115

```
<210> SEQ ID NO 74
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 74
```

Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Gly Asp Lys Tyr Val
                20                  25                  30

Tyr Trp Tyr Gln Gln Lys Pro Gly Gln Ala Pro Val Leu Val Ile Tyr
            35                  40                  45

Asp Thr Asn Lys Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp Leu Asp Phe Asn Thr
                85                  90                  95

Tyr Val Phe Gly Gly Gly Thr Lys Leu Thr Val Leu
            100                 105

```
<210> SEQ ID NO 75
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 75
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Ser Trp Val Arg Gln Ala Pro Gly Gln Gly Leu Glu Trp Met
            35                  40                  45

Gly Trp Ile Asn Pro Leu Lys Gly Asn Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Glu Gly Met Tyr Phe Asp Ile Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys
210                 215

<210> SEQ ID NO 76
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 76

Ser Tyr Glu Leu Thr Gln Pro Leu Ser Val Ser Val Ala Leu Gly Gln
 1               5                  10                  15

Thr Ala Arg Ile Thr Cys Ser Gly Asp Ser Ile Gly Asp Lys Tyr Val
             20                  25                  30

Tyr Trp Tyr Gln Gln Lys Pro Gly Gln Ala Pro Val Leu Val Ile Tyr
            35                  40                  45

Asp Thr Asn Lys Arg Pro Ser Gly Ile Pro Glu Arg Phe Ser Gly Ser
 50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Ser Trp Asp Leu Asp Phe Asn Thr
                 85                  90                  95

Tyr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 77
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 77
caggtgcagc tggtgcagtc aggcgccgaa gtgaagaaac ccggcgctag tgtgaaggtg      60
tcctgtaaag ctagtggcta caccttcact agctactaca tgagctgggt gcgacaggcc    120
cctggacagg gcctggaatg gatgggctgg attaaccccc tgaagggcaa cactaactac    180
gcccagaaat tccagggccg agtgactatg actagggaca ctagcattag caccgcctac    240
atggaactgt ctaggctgag atcagaggac accgccgtgt actactgcgc tagagaaggc    300
atgtacttcg acatctgggg ccagggcacc ctggtgacag tgtcttct                 348

<210> SEQ ID NO 78
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 78
agctacgagc tgactcagcc cctgagcgtg tcagtggccc tgggacagac cgctagaatc     60
acctgtagcg gcgactctat cggcgacaaa tacgtgtact ggtatcagca gaagcccggc    120 caggccccg tgctggtgat ctacgacact aacaagcggc ctagcggcat ccccgagcgg     180
tttagcggct ctaatagcgg caacaccgct accctgacta ttagtagggc tcaggccggc    240
gacgaggccg actactactg tcagtcatgg gacctggact caacaccta cgtgttcggc     300 ggaggcacta agctgaccgt gctg                                           324

<210> SEQ ID NO 79
<211> LENGTH: 657
<212> TYPE: DNA
<213> ORGANISM: Artificial Sequence
<220> FEATURE:
<223> OTHER INFORMATION: Synthetic polynucleotide

<400> SEQUENCE: 79
caggtgcagc tggtgcagtc aggcgccgaa gtgaagaaac ccggcgctag tgtgaaggtg     60
tcctgtaaag ctagtggcta caccttcact agctactaca tgagctgggt gcgacaggcc   120
cctggacagg gcctggaatg gatgggctgg attaaccccc tgaagggcaa cactaactac   180
gcccagaaat tccagggccg agtgactatg actagggaca ctagcattag caccgcctac   240
atggaactgt ctaggctgag atcagaggac accgccgtgt actactgcgc tagagaaggc   300
atgtacttcg acatctgggg ccagggcacc ctggtgacag tgtcttctgc tagcactaag   360
ggcccctccg tgttccctct ggccccttcc agcaagtcta cctctggcgg caccgctgct   420
ctgggctgcc tggtgaagga ctacttccct gagcctgtga cagtgtcctg gaactctggc   480

```
gccctgacct ccggcgtgca caccttccct gccgtgctgc agtcctccgg cctgtactcc    540
ctgtcctccg tggtgacagt gccttcctcc agctgggca cccagaccta tatctgcaac    600
gtgaaccaca agccttccaa caccaaggtg acaagcggg tggagcctaa gtcatgc       657
```

<210> SEQ ID NO 80
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 80

```
agctacgagc tgactcagcc cctgagcgtg tcagtggccc tgggacagac cgctagaatc     60
acctgtagcg gcgactctat cggcgacaaa tacgtgtact ggtatcagca gaagcccggc    120 caggccccg tgctggtgat ctacgacact aacaagcggc ctagcggcat ccccgagcgg    180
tttagcggct ctaatagcgg caacaccgct accctgacta ttagtagggc tcaggccggc    240
gacgaggccg actactactg tcagtcatgg gacctggact caacaccta cgtgttcggc    300 ggaggcacta agctgaccgt gctgggccag cctaaggctg cccccagcgt gaccctgttc    360 cccccagca gcgaggagct gcaggccaac aaggccaccc tggtgtgcct gatcagcgac    420
ttctacccag cgccgtgac cgtggcctgg aaggccgaca gcagcccgt gaaggccggc    480 gtggagacca ccaccccag caagcagagc aacaacaagt acgccgccag cagctacctg    540
agcctgaccc ccgagcagtg gaagagccac aggtcctaca gctgccaggt gacccacgag    600
ggcagcaccg tggaaaagac cgtggcccca accgagtgca gc                      642
```

<210> SEQ ID NO 81
<211> LENGTH: 166
<212> TYPE: PRT
<213> ORGANISM: Homo sapiens

<400> SEQUENCE: 81

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 82
<211> LENGTH: 165
<212> TYPE: PRT
<213> ORGANISM: Macaca fascicularis

<400> SEQUENCE: 82

```
Ala Pro Pro Arg Leu Ile Cys Asp Ser Arg Val Leu Glu Arg Tyr Leu
1               5                   10                  15

Leu Glu Ala Lys Glu Ala Glu Asn Val Thr Met Gly Cys Ser Glu Ser
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Val
65                  70                  75                  80

Leu Ala Asn Ser Ser Gln Pro Phe Glu Pro Leu Gln Leu His Met Asp
                85                  90                  95

Lys Ala Ile Ser Gly Leu Arg Ser Ile Thr Thr Leu Leu Arg Ala Leu
            100                 105                 110

Gly Ala Gln Glu Ala Ile Ser Leu Pro Asp Ala Ala Ser Ala Ala Pro
        115                 120                 125

Leu Arg Thr Ile Thr Ala Asp Thr Phe Cys Lys Leu Phe Arg Val Tyr
    130                 135                 140

Ser Asn Phe Leu Arg Gly Lys Leu Lys Leu Tyr Thr Gly Glu Ala Cys
145                 150                 155                 160

Arg Arg Gly Asp Arg
                165
```

<210> SEQ ID NO 83
<211> LENGTH: 166
<212> TYPE: PRT
<213> ORGANISM: Mus musculus

<400> SEQUENCE: 83

```
Ala Pro Pro Arg Leu Ile Cys Asp Ser Arg Val Leu Glu Arg Tyr Ile
1               5                   10                  15

Leu Glu Ala Lys Glu Ala Glu Asn Val Thr Met Gly Cys Ala Glu Gly
            20                  25                  30

Pro Arg Leu Ser Glu Asn Ile Thr Val Pro Asp Thr Lys Val Asn Phe
        35                  40                  45

Tyr Ala Trp Lys Arg Met Glu Val Glu Glu Gln Ala Ile Glu Val Trp
    50                  55                  60

Gln Gly Leu Ser Leu Leu Ser Glu Ala Ile Leu Gln Ala Gln Ala Leu
65                  70                  75                  80

Leu Ala Asn Ser Ser Gln Pro Pro Glu Thr Leu Gln Leu His Ile Asp
                85                  90                  95

Lys Ala Ile Ser Gly Leu Arg Ser Leu Thr Ser Leu Leu Arg Val Leu
            100                 105                 110

Gly Ala Gln Lys Glu Leu Met Ser Pro Pro Asp Thr Thr Pro Pro Ala
        115                 120                 125

Pro Leu Arg Thr Leu Thr Val Asp Thr Phe Cys Lys Leu Phe Arg Val
    130                 135                 140

Tyr Ala Asn Phe Leu Arg Gly Lys Leu Lys Leu Tyr Thr Gly Glu Val
145                 150                 155                 160
```

Cys Arg Arg Gly Asp Arg
                165

<210> SEQ ID NO 84
<211> LENGTH: 166
<212> TYPE: PRT
<213> ORGANISM: Rattus norvegicus

<400> SEQUENCE: 84

Ala Pro Pro Arg Leu Ile Cys Asp Ser Arg Val Leu Glu Arg Tyr Ile
1               5                   10                  15

Leu Glu Ala Lys Glu Ala Glu Asn Val Thr Met Gly Cys Ala Glu Gly
            20                  25                  30

Pro Arg Leu Ser Glu Asn Ile Thr Val Pro Asp Thr Lys Val Asn Phe
        35                  40                  45

Tyr Ala Trp Lys Arg Met Lys Val Glu Glu Gln Ala Val Glu Val Trp
    50                  55                  60

Gln Gly Leu Ser Leu Leu Ser Glu Ala Ile Leu Gln Ala Gln Ala Leu
65                  70                  75                  80

Gln Ala Asn Ser Ser Gln Pro Pro Glu Ser Leu Gln Leu His Ile Asp
                85                  90                  95

Lys Ala Ile Ser Gly Leu Arg Ser Leu Thr Ser Leu Leu Arg Val Leu
            100                 105                 110

Gly Ala Gln Lys Glu Leu Met Ser Pro Pro Asp Ala Thr Gln Ala Ala
        115                 120                 125

Pro Leu Arg Thr Leu Thr Ala Asp Thr Phe Cys Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Arg Gly Asp Arg
                165

<210> SEQ ID NO 85
<211> LENGTH: 199
<212> TYPE: PRT
<213> ORGANISM: Oryctolagus cuniculus

<400> SEQUENCE: 85

Lys Leu Ala Thr Met Gly Val Arg Gly Arg Leu Ala Leu Leu Pro Leu
1               5                   10                  15

Ala Leu Leu Cys Leu Leu Val Leu Ala Leu Gly Leu Pro Val Leu Gly
            20                  25                  30

Ala Pro Ala Arg Leu Ile Cys Asp Ser Arg Val Leu Glu Arg Tyr Ile
        35                  40                  45

Leu Glu Ala Lys Glu Ala Glu Asn Val Thr Met Gly Cys Ala Glu Gly
    50                  55                  60

Cys Ser Leu Gly Glu Asn Ile Thr Val Pro Asp Thr Lys Val Asn Phe
65                  70                  75                  80

His His Trp Lys Lys Ser Glu Ala Gly Arg His Ala Val Glu Val Trp
                85                  90                  95

Gln Gly Leu Ala Leu Leu Ser Glu Ala Met Leu Arg Ser Gln Ala Leu
            100                 105                 110

Leu Ala Asn Ser Ser Gln Leu Pro Glu Thr Leu Gln Val His Val Asp
        115                 120                 125

Lys Ala Val Ser Gly Leu Arg Ser Leu Thr Ser Leu Leu Arg Ala Leu
    130                 135                 140

Gly Val Gln Lys Glu Ala Val Ser Pro Pro Glu Ala Ala Ser Ser Ala
145                 150                 155                 160

Ala Pro Leu Arg Thr Val Ala Ala Asp Thr Leu Cys Lys Leu Phe Arg
                165                 170                 175

Ile Tyr Ser Asn Phe Leu Arg Gly Lys Leu Lys Leu Tyr Thr Gly Glu
            180                 185                 190

Ala Cys Arg Arg Gly Asp Arg
        195

<210> SEQ ID NO 86
<211> LENGTH: 23
<212> TYPE: PRT
<213> ORGANISM: Homo sapiens

<400> SEQUENCE: 86

Arg Leu Ile Cys Asp Ser Arg Val Leu Glu Arg Tyr Leu Leu Glu Ala
1               5                   10                  15

Lys Glu Ala Glu Asn Ile Thr
            20

<210> SEQ ID NO 87
<211> LENGTH: 28
<212> TYPE: PRT
<213> ORGANISM: Homo sapiens

<400> SEQUENCE: 87

Val Gly Gln Gln Ala Val Glu Val Trp Gln Gly Leu Ala Leu Leu Ser
1               5                   10                  15

Glu Ala Val Leu Arg Gly Gln Ala Leu Leu Val Asn
            20                  25

<210> SEQ ID NO 88
<211> LENGTH: 25
<212> TYPE: PRT
<213> ORGANISM: Homo sapiens

<400> SEQUENCE: 88

Phe Arg Lys Leu Phe Arg Val Tyr Ser Asn Phe Leu Arg Gly Lys Leu
1               5                   10                  15

Lys Leu Tyr Thr Gly Glu Ala Cys Arg
            20                  25

<210> SEQ ID NO 89
<211> LENGTH: 28
<212> TYPE: PRT
<213> ORGANISM: Homo sapiens

<400> SEQUENCE: 89

Thr Gly Cys Ala Glu His Cys Ser Leu Asn Glu Asn Ile Thr Val Pro
1               5                   10                  15

Asp Thr Lys Val Asn Phe Ala Trp Lys Arg Met Glu
            20                  25

<210> SEQ ID NO 90
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Gly Gly Asp His Asn Ser Gly Trp Gly Leu Asp Ile Trp Gly Gln
            100                 105                 110

Gly Thr Leu Val Thr Val Ser Ser
            115                 120

<210> SEQ ID NO 91
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 91

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
            85                  90                  95

Asn Gly Ala Asn Phe Gly Gln Gly Thr Lys Leu Thr Val Leu Gly
            100                 105                 110
```